United States Patent
Chen et al.

(10) Patent No.: US 11,512,304 B2
(45) Date of Patent: Nov. 29, 2022

(54) ENGINEERED DECARBOXYLASE POLYPEPTIDES AND THEIR USES IN PREPARING TYRAMINE AND DOPAMINE

(71) Applicant: Enzymaster (Ningbo) Bio-Engineering Co., Ltd, Ningbo (CN)

(72) Inventors: Haibin Chen, Ningbo (CN); Yong Koy Bong, Ningbo (CN); Qing Xu, Ningbo (CN); Dongxiao Hu, Ningbo (CN); Chengxiao Zhang, Ningbo (CN); Baoqin Cai, Ningbo (CN)

(73) Assignee: ENZYMASTER (NINGBO) BIO-ENGINEERING CO., LTD., Ningbo (CN)

( * ) Notice: Subject to any disclaimer, the term of this patent is extended or adjusted under 35 U.S.C. 154(b) by 100 days.

(21) Appl. No.: 17/045,088

(22) PCT Filed: Apr. 1, 2019

(86) PCT No.: PCT/CN2019/080901
§ 371 (c)(1),
(2) Date: Oct. 2, 2020

(87) PCT Pub. No.: WO2019/192438
PCT Pub. Date: Oct. 10, 2019

(65) Prior Publication Data
US 2021/0147822 A1 May 20, 2021

(30) Foreign Application Priority Data

Apr. 5, 2018 (CN) .......................... 201810302720.1

(51) Int. Cl.
*C12N 9/88* (2006.01)
*C12N 11/00* (2006.01)
*C12P 13/00* (2006.01)

(52) U.S. Cl.
CPC ................ *C12N 9/88* (2013.01); *C12N 11/00* (2013.01); *C12P 13/001* (2013.01); *C12Y 401/01025* (2013.01); *C12Y 401/01028* (2013.01)

(58) Field of Classification Search
CPC ......... C12N 9/88; C12N 11/00; C12P 13/001; C12Y 401/01025; C12Y 401/01028
See application file for complete search history.

(56) References Cited

FOREIGN PATENT DOCUMENTS

| CN | 103421734 A | 12/2013 |
|---|---|---|
| EP | 1621626 A1 | 2/2006 |
| WO | WO 2000/047236 A1 | 8/2000 |
| WO | WO 2012/135389 A2 | 10/2012 |

OTHER PUBLICATIONS

Chaillou, S., Gen Bank accession No. SMH68558, Apr. 2017.*
Witkowski et al., Biochemistry 38:11643-11650, 1999.*
Tang et al., Phil Trans R Soc B 368:Mar. 18, 2012, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
N. Shuhei et al., "Evaluation of Brachypodium distachyon L-Tyrosine Decarboxylase Using L-Tyrosine Over-Producing *Saccharomyces cervisiae*", PLoS ONE, vol. 10, No. 5, pp. 1-12 (May 21, 2015).

* cited by examiner

*Primary Examiner* — Delia M Ramirez
(74) *Attorney, Agent, or Firm* — Smith Patent, LLC; Chalin A. Smith

(57) ABSTRACT

Provided herein are engineered decarboxylase polypeptides that are useful for catalyzing the decarboxylation of amino acids such as L-tyrosine to produce tyramine or catalyzing the decarboxylation of L-DOPA to produce dopamine. Also provided are the preparation process of engineered decarboxylase polypeptides as well as reaction process under industrial-relevant conditions. The disclosure also provides polynucleotide sequences encoding engineered decarboxylase polypeptides, recombinant host cells capable of expressing engineered decarboxylase polypeptides, and methods of producing tyramine or dopamine using the engineered decarboxylase polypeptides. Compared to the wild type decarboxylase, the engineered polypeptide provided by this disclosure has better activity and/or stability. The use of the engineered polypeptides for the preparation of tyramine or dopamine reduces the production cost and has a good industrial application prospect.

15 Claims, No Drawings
Specification includes a Sequence Listing.

ENGINEERED DECARBOXYLASE POLYPEPTIDES AND THEIR USES IN PREPARING TYRAMINE AND DOPAMINE

PRIORITY

This application corresponds to the U.S. National phase of International Application No. PCT/CN2019/080901, filed Apr. 1, 2019, which, in turn, claims priority to Chinese Patent Application No. 2018-10302720.1 filed Apr. 5, 2018, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Oct. 2, 2020, is named LNK_221US_SEQ_LIST_TXT.txt and is 416,591 bytes in size.

TECHNICAL FIELD OF THE PRESENT INVENTION

The present invention relates to the field of biotechnology, in particular to engineered decarboxylase polypeptides, their preparation method, and the reaction process using engineered decarboxylase polypeptides to produce tyramine and dopamine.

BACKGROUND OF THE PRESENT INVENTION

Tyramine is also known as 4-(2-aminoethyl)-phenol. It can be found in some of the parasitic trees and putrid animal tissues. Dopamine is a neurotransmitter that helps cells transmit pulsed chemicals. As two important biological amines, tyramine and dopamine are of great physiological and pharmaceutical value. Inside the human body, tyramine plays an effective role in promoting norepinephrine secretion, contracting peripheral nerves and causing hypertension. Dopamine has the effects on enhancing myocardial contractility, increasing blood output, and accelerating heart rate. In pharmaceutical and chemical industry, tyramine is a synthetic precursor of many drugs such as dopamine and the hypolipidemic bezafibrate, while dopamine is a precursor of drugs such as L-DOPA and rifampin. In addition, tyramine is widely used in the preparation of biomedical materials such as hyaluronic acid-tyramine hydrogels, polyvinyl alcohol-tyramine hydrogels, biotin-tyramine conjugates, and antibody purification media.

The present technology of tyramine synthesis at industrial scale is mainly based on chemical synthesis methods such as Benzeneacetonitrile method, Anisaldehyde method, p-hydroxybenzaldehyde method and phenol method. The synthesis of dopamine is mainly carried out by the vanillin method. These methods have many shortcomings, for example, very demanding on equipment or facilities, environmental pollution, resulting in difficulties for industrial production. In recent years, with the increasing awareness of environmental protection, the enzymatic biotransformation method has received more attention as green technology. The enzymatic reaction has the advantages of having high stereoselectivity, mild reaction conditions and high catalytic efficiency, showing good industrial application prospects. Therefore, the enzymatic reaction has become an important research field in the synthesis of tyramine and dopamine.

Currently, a feasible enzymatic reaction of generating tyramine or dopamine is applying decarboxylase on L-tyrosine or L-DOPA. Studies on tyrosine decarboxylase found that the expression of tyrosine decarboxylase in wild type bacteria was low, and the activity or stability of wild type tyrosine decarboxylase could not meet the needs of industrial production. The method of producing dopamine by employing decarboxylase on L-DOPA at industrial scale has not been reported.

SUMMARY OF THE PRESENT INVENTION

In order to solve the problems existing in the current chemical process of producing tyramine, the present invention provides an economical and efficient solution using enzymatic method which features high product concentration, mild reaction conditions and environmental friendliness. It is easy to operate and easy to be scaled up in industrial setting, so it has a good industrial application prospect.

In the first aspect, the present invention provides a novel engineered decarboxylase polypeptide. These engineered decarboxylase polypeptides are derived from a wild type decarboxylase with poor performance through a creative process of directed evolution, comprising a certain number of amino-acid-residue substitutions, insertions or deletions. This wild type decarboxylase is from *Streptococcus thermophilus*, its amino acid sequence is shown as SEQ ID No: 2. As measured by the inventors, the decarboxylase of SEQ ID No 2 has decarboxylase activity, which can catalyze tyrosine decarboxylation to generate tyramine (Scheme 1) and catalyze the L-DOPA decarboxylation to generate dopamine (Scheme 2). However, the decarboxylase of SEQ ID No 2 is not stable enough. There is a significant loss of the activity of SEQ ID No 2—even it is kept under low temperature conditions (−20° C. to 4° C.), which brings difficulties in storing and further processing (for example, to make an immobilized enzyme) after being expressed by microorganisms like *E. coli*. As measured by the inventors, the decarboxylase of SEQ ID No 2 (which was prepared by the method described in Example 2) showed the following stability: after being kept at −20° C. for 48 hours, the activity of SEQ ID No 2 in Scheme 1 or Scheme 2 was decreased by 30%; after being kept at 4° C. for 48 hours, its activity was reduced by about 50%; after being kept at 30° C. for 48 hours, its activity was dropped by about 70%.

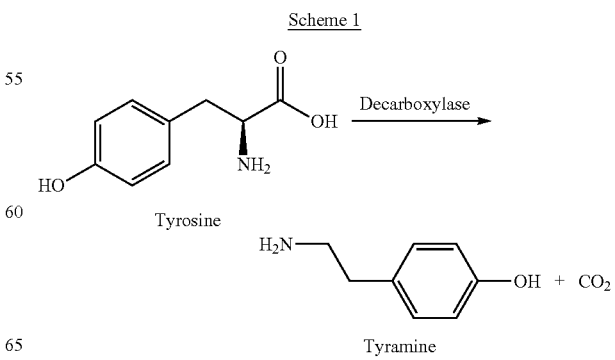

Scheme 1

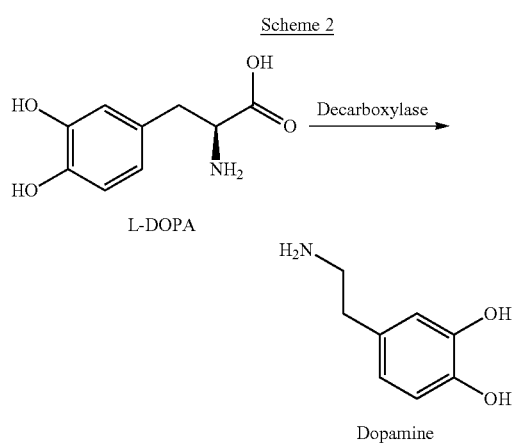

Scheme 2

In order to have more stable decarboxylase to enable industrial application of scheme 1 and scheme 2, the inventors have developed a series of stable engineered decarboxylase polypeptides with better activity. The engineered decarboxylase polypeptides were created through a creative process of directed evolution, comprising a certain number of amino-acid-residue substitutions, insertions or deletions.

The improved engineered decarboxylase polypeptides provided in the present invention have higher stability and/or activity compared with the wild type decarboxylase of SEQ ID NO: 2. On one hand, it can catalyze the decarboxylation of L-tyrosine to generate tyramine in more efficient way, and it also better catalyzes the decarboxylation of L-DOPA to produce dopamine. In some embodiments, engineered decarboxylase polypeptides of the present disclosure are capable of converting L-tyrosine to tyramine and carbon dioxide with an activity at least equal to or greater than that of SEQ ID No: 2; in some embodiments, engineered decarboxylase polypeptides of the present disclosure are capable of converting L-DOPA to dopamine and carbon dioxide with an activity at least equal to or greater than that of SEQ ID No: 2.

These engineered decarboxylase polypeptides may comprise an amino acid sequence that differs from the sequence of SEQ ID NO: 2 in one or more residue positions selected from: X12, X26, X30, X44, X51, X52, X56, X58, X63, X72, X123, X133, X147, X181, X210, X271, X294, X317, X376, X380, X388, X454, X465, X467, X517, X530, X535, X536, X538, X576. The engineered decarboxylase polypeptides comprise an amino acid sequence comprising at least one of the following features (these features are substitutions of amino acid residues to the reference sequence of SEQ ID NO: 2): D12Y, D12T, Q26T, Q26F, D30E, Q44R, Q44K, Q44I, Q44L, K51P, K51T, P52T, P52V, P52S, A56S, A56T, A56P, Q58R, Q58V, Q58H, E63D, K72R, A123S, M133V, Y147F, A181E, N210L, I271P, I271S, V294A, V317E, A376S, F380L, I388T, K454R, K465R, K465V, K465L, K465G, V467L, N517D, N530D, V535W, T536G, S538V, E576K; Or, in addition to the abovementioned differences, engineered decarboxylase polypeptides comprise insertions or deletions of 1, 2, 3, 4, 5, 6, 7, 8, 9, 10, 11, 12, 13, 14, 15, 16, 18, 20, 21, 22, 23, 24, 25 or more amino acid residues.

More specifically, in some embodiments, the engineered decarboxylase polypeptides which were improved over SEQ ID NO: 2 comprise a sequence corresponding to SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104. In some embodiments, the—engineered decarboxylase polypeptides comprise an amino acid sequence that is at least 80%, 85%, 86%, 87%, 88%, 89%, 90%, 91%, 92%, 93%, 94%, 95%, 96%, 97%, 98%, 99% or more identical to the reference sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104.

The identity between two amino acid sequences or two nucleotide sequences can be obtained by commonly used algorithms in the art and can be calculated according to default parameters by using NCBI Blastp and Blastn software, or by using the Clustal W algorithm (Nucleic Acid Research, 22 (22): 4673-4680, 1994).

In another aspect, this invention provides polynucleotide sequences encoding engineered decarboxylase polypeptides. In some embodiments, a polynucleotide can be part of an expression vector having one or more control sequences for the expression of an engineered decarboxylase polypeptide. In some embodiments, polynucleotides can comprise sequences corresponding to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103.

As known to people skilled in the art, due to the degeneracy of the nucleotide codons, the polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104 are not limited to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103. The polynucleotide sequences of the decarboxylase polypeptides of the present invention may also be any other polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104.

In another aspect, this disclosure provides polynucleotides comprising sequences encoding engineered decarboxylase polypeptides, expression vectors and host cells capable of expressing engineered decarboxylase polypeptides. In some embodiments, the host cell can be bacterial host cell, such as E. coli. The host cell can be used to express and isolate the engineered decarboxylase described herein, or alternatively be directly used in the reaction for conversion of substrates to products.

In some embodiments, the engineered decarboxylase in the form of whole cell, crude extract, isolated enzyme, or purified enzyme can be used alone or in an immobilized form, such as immobilization on a resin.

The present disclosure also provides the process of preparing an amino compound of formula (I) using the engineered decarboxylase polypeptides disclosed herein to convert an amino acid of formula (II):

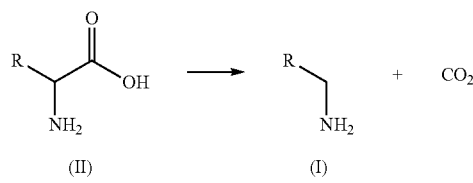

wherein R is an optionally substituted or unsubstituted $C_1$-$C_8$ hydrocarbyl, or an optionally substituted or unsubstituted aryl or heteroaryl; the process comprising that, amino acid substrates of formula (II) were contacted with the decarboxylase polypeptides under suitable reaction conditions, wherein the decarboxylase polypeptides are the engineered decarboxylase polypeptides as described herein. In some embodiments, the engineered decarboxylase polypeptides have at least 80%, 85%, 86%, 87%, 88%, 89%, 90%, 91%, 92%, 93%, 94%, 95%, 96%, 97%, 98%, 99% or more of sequence identity to SEQ ID NO: 2 and can convert a compound of formula (II) to the compound of formula (I) at higher conversion compared to SEQ ID NO: 2.

In some embodiments, the engineered decarboxylase polypeptides can be used in the process of preparing Tyramine:

Tyramine

In these embodiments, the process comprises that, under suitable reaction conditions, the compound of formula A1:

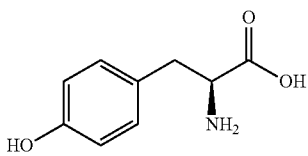

were contacted with the engineered decarboxylase polypeptides disclosed herein.

In some embodiments, the engineered decarboxylase polypeptides can be used in the process of preparing Dopamine:

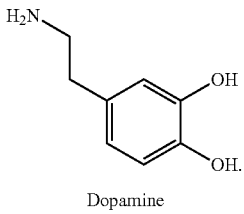 [SMILES: NCCc1ccc(O)c(O)c1]

Dopamine

In these embodiments, the process comprises that, under suitable reaction conditions, the compound of formula A2:

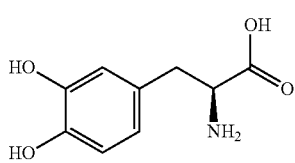

were contacted with the engineered Decarboxylase Polypeptides disclosed herein.

Specific embodiments of engineered decarboxylase polypeptides for use in this process are further provided in the examples. An engineered decarboxylase polypeptide that can be used in the above process can comprise one or more sequences selected from the amino acid sequences corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104.

Any of the processes for the preparation of a compound of formula (I), Tyramine or Dopamine using an engineered polypeptide as disclosed herein can be performed under a range of suitable reaction conditions, including but not limited to pH, temperature, buffer, solvent system, substrate loading, polypeptide loading, pressure, and reaction time range. For example, in some embodiments, preparing a compound of formula (I), Tyramine or Dopamine can be performed, wherein suitable reaction conditions include: (a) about 5 g/L to about 400 g/L loading of a substrate compound (e.g., compound (II), A1 or A2); (b) about 0.5 g/L to about 10 g/L loading of engineered polypeptide, or about 1 g/L to about 100 g/L loading of wet cells expressing the engineered polypeptide; (c) 0% (v/v) to about 60% (v/v) of organic solvent, including but not limited to, dimethyl sulfoxide (DMSO), dimethylformamide (DMF), isopropyl acetate, Methanol, ethanol, propanol or isopropanol (IPA); (d) PLP cofactor concentration from about 0.01 mM to 5 mM; (e) a pH of about 3.0 to about 8.0; and (f) a temperature of about 10° C. to about 60° C.

DETAILED DESCRIPTION OF THE PRESENT INVENTION

1. Definitions

Unless expressly defined otherwise, technical and scientific terms used in this disclosure have the meanings that are commonly understood by people skilled in the art.

"Protein", "polypeptide" and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.). This definition includes D-amino acids and L-amino acids, as well as mixtures of D-amino acids and L-amino acids.

"Engineered decarboxylase", "engineered decarboxylase polypeptide", "improved decarboxylase polypeptide" and "engineered polypeptide" are used interchangeably herein.

"Cells" or "wet cells" refers to host cells which expresses a polypeptide or engineered polypeptide, including the wet cells obtained in the preparation procedures shown in Example 2 and Example 9.

"Polynucleotide" and "nucleic acid" are used interchangeably herein.

"Cofactor" as used herein refers to a non-protein compound that operates in conjunction with an enzyme in a catalytic reaction. As used herein, "cofactor" is intended to encompass the vitamin B6 family compounds pyridoxal-5'-phosphate (PLP), pyridoxine (pyridoxol, or PN), pyridoxal (PL), pyridoxamine (PM), pyridoxine phosphate (PNP) and pyridoxamine phosphate (PMP), which are sometimes also referred to as coenzymes.

"Pyridoxal phosphate", "PLP", "pyridoxal-5'-phosphate", "PYP" and "P5P" are used interchangeably herein to refer to compounds that act as coenzyme in decarboxylase reactions.

"Coding sequence" refers to that portion of a nucleic acid (e.g., a gene) that encodes an amino acid sequence of a protein.

"Naturally occurring" or "wild type" refers to the form found in nature. For example, a naturally occurring or wild type polypeptide or polynucleotide sequence is a sequence that is present in an organism that can be isolated from sources in nature and which has not been intentionally modified by manual procedures.

"Recombinant" or "engineered" or "non-naturally occurring" when used with reference to, for example, a cell, nucleic acid or polypeptide, refers to a material or material corresponding to the native form of the material, that has been modified in a manner that would not otherwise exist in nature, or is identical thereto but produced or derived from synthetic material and/or by manipulation using recombinant techniques.

"Sequence identity" and "homology" are used interchangeably herein to refer to comparisons between polynucleotide sequences or polypeptide sequences ("sequence identity" is generally expressed as a percentage), and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage can be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those skilled in the art will appreciate that there are many established algorithms available to align two sequences. The optimal alignment of sequences for comparison can be conducted, for example, by the local sequence alignment algorithm of Smith and Waterman, 1981, Adv. Appl. Math. 2: 482, by the global alignment algorithm of Needleman and Wunsch, 1970, J. Mol. Biol. 48: 443, by the search for similarity method of Pearson and Lipman, 1988, Proc. Natl. Acad. Sci. USA 85: 2444, by computerized implementations of these algorithms (GAP, BESTFIT, FASTA, and TFASTA in the GCG Wisconsin Package) or by visual inspection (see generally, Current Protocols in Molecular Biology, FM Ausubel et al. eds., Current Protocols, a Joint Venture between Greene Publishing Associates, Inc. and John Wiley & Sons, Inc., (1995 Supplement) (Ausubel)). Examples of algorithms that are suitable for determining the percent sequence identity and percent sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analysis is publicly available through the National Center for Biotechnology Information website. The algorithm involves first identifying high scoring sequence pairs (HSPs) by identifying short words of length W in the query sequence, which either match or satisfy some positive-valued threshold scores T when aligned with a word of the same length in the database sequence. T is referred to as, the neighborhood word score threshold (Altschul et al., Supra). These initial neighborhood word hits serve as seeds for initiating searches to find longer HSPs that contain them. The word hits are then extended in both directions along each sequence for as far as the cumulative alignment score can be increased. For nucleotide sequences, the cumulative scores are calculated using the parameters M (reward score for matched pair of residues; always >0) and N (penalty score for mismatched residues; always <0). For amino acid sequences, a scoring matrix is used to calculate the cumulative score. The extension of the word hits in each direction are halted when: the cumulative alignment score falls off by the quality X from its maximum achieved value; the cumulative score goes 0 or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, the expected value (E) of 10, M=5, N=−4, and a comparison of both strands as a default value. For amino acid sequences, the BLASTP program uses as defaults the wordlength (W) of 3, the expected value (E) of 10 and the BLOSUM62 scoring matrix (see Henikoff and Henikoff, 1989, Proc Natl Acad Sci USA 89: 10915). Exemplary determination of sequence alignments and % sequence identity can employ the BESTFIT or GAP programs in the GCG Wisconsin Software package (Accelrys, Madison Wis.), using the default parameters provided.

"Reference sequence" refers to a defined sequence that is used as a basis for sequence comparison. The reference sequence may be a subset of a larger sequence, for example, a full-length gene or a fragment of a polypeptide sequence. In general, a reference sequence is at least 20 nucleotides or amino acid residues in length, at least 25 residues in length, at least 50 residues in length, or the full length of the nucleic acid or polypeptide. Because two polynucleotides or polypeptides may each (1) comprise a sequence (i.e., a portion of the complete sequence) that is similar between two sequences, and (2) may further comprise sequences that is divergent between the two sequences, sequence comparisons between two (or more) polynucleotides or polypeptides are typically performed by comparing the sequences of the two polynucleotides or polypeptides over a "comparison window" to identify and compare local regions of sequence similarity. In some embodiments, a "reference sequence" is not intended to be limited to a wild type sequence, and may comprise engineered or altered sequences. For example, "a reference sequence with leucine at the residue corresponding to X44 based on SEQ ID NO: 2" refers to a reference sequence wherein the corresponding residue at position X44 in SEQ ID NO: 2 which is glutamine, has been altered to leucine.

A "comparison window" refers to a conceptual segment of at least about 20 contiguous nucleotide positions or amino acid residues, wherein the sequence may be compared to a reference sequence of at least 20 contiguous nucleotides or amino acids and wherein the portions of the sequence in the comparison window may comprise additions or deletions (i.e., gaps) of 20% or less as compared to a reference sequence (which does not comprise additions or deletions) for optimal alignment of the two sequences. The comparison window can be longer than 20 contiguous residues, and optionally include 30, 40, 50, 100 or more residues.

In the context of the numbering for a given amino acid or polynucleotide sequence, "corresponding to," "reference to" or "relative to" refers to the numbering of the residues of a specified reference when the given amino acid or polynucleotide sequence is compared to the reference sequence. In other words, the residue number or residue position of a given sequence is designated with respect to the reference sequence, rather than by the actual numerical position of the residue within the given amino acid or polynucleotide sequence. For example, a given amino acid sequence such as an engineered decarboxylase can be aligned to a reference sequence by introducing gaps to optimize residue matches between the two sequences. In these cases, although there are gaps, the numbering of the residue in a given amino acid or polynucleotide sequence is made with respect to the reference sequence to which they have been aligned.

"Amino acid difference" or "residue difference" refers to the difference in amino acid residues at a position of a polypeptide sequence relative to the amino acid residue at a corresponding position in the reference sequence. The positions of amino acid differences are generally referred to herein as "Xn", where n refers to the corresponding position in the reference sequence on which the residue differences are based. For example, "a residue difference at position X44 as compared to SEQ ID NO: 2" refers to the difference in amino acid residues at the polypeptide position corresponding to position 44 of SEQ ID NO: 2. Thus, if the reference polypeptide of SEQ ID NO: 2 has a glutamine at position 44, then "a residue difference at position X44 as compared to SEQ ID NO: 2" refers to an amino acid substitution of any residue other than glutamine at the position of the polypeptide corresponding to position 44 of SEQ ID NO: 2. In most of the examples herein, the specific amino acid residue difference at the position is indicated as "XnY", wherein "Xn" specified to the corresponding position as described above, and "Y" is the single letter identifier of the amino acid found in the engineered polypeptide (i.e., a different residue than in the reference polypeptide). In some examples (e.g., in Table 1), the present disclosure also provides specific amino acid differences denoted by the conventional notation "AnB", where A is a single letter identifier of a residue in the reference sequence, "n" is the number of residue position in the reference sequence, and B is the single letter identifier for the residue substitution in the sequence of the engineered polypeptide. In some examples, an engineered polypeptide of this disclosure may comprise one or more amino acid residue differences relative to a reference sequence, which is indicated by a list of specific positions at which residue differences are present relative to a reference sequence. In some embodiments, more than one amino acid residue can be used in a specific residue position of an engineered polypeptide, the various amino acid residues that can be used are separated by a "/" (e.g., X44R/X44I).

"Deletion" refers to the modification of a polypeptide by removing one or more amino acids from a reference polypeptide. Deletions can include the removal of one or more amino acids, two or more amino acids, five or more amino acids, ten or more amino acids, fifteen or more amino acids, or twenty or more amino acids, up to 10% of the total number of amino acids of the enzyme, or up to 20% of the total number of amino acids making up the reference enzyme while retaining the enzymatic activity of the engineered decarboxylase and/or retaining the improved properties of the engineered decarboxylase. Deletion may involve the internal portion and/or the terminal portion of the polypeptide. In various embodiments, deletions may include a contiguous segment or may be discontinuous.

"Insertion" refers to the modification of a polypeptide by adding one or more amino acids from a reference polypeptide. In some embodiments, the improved engineered decarboxylase comprises insertions of one or more amino acids to a naturally occurring decarboxylase polypeptide as well as insertions of one or more amino acids to other engineered decarboxylase polypeptides. It can be inserted in the internal portions of the polypeptide or inserted to the carboxyl or amino terminus. As used herein, insertions include fusion proteins known in the art. The insertion can be a contiguous segment of amino acids or separated by one or more amino acids in naturally occurring or engineered polypeptides.

"Fragment" as used herein refers to a polypeptide having an amino terminal and/or carboxyl terminal deletion, but where the remaining amino acid sequence is identical to the corresponding position in the sequence. Fragments may be at least 10 amino acids long, at least 20 amino acids long, at least 50 amino acids long or longer, and up to 70%, 80%, 90%, 95%, 98% and 99% of the full-length decarboxylase polypeptide.

An "isolated polypeptide" refers to a polypeptide that is substantially separated from other substances with which it is naturally associated, such as proteins, lipids, and polynucleotides. The term comprises polypeptides that have been removed or purified from their naturally occurring environment or expression system (e.g., in host cells or in vitro synthesis). Engineered decarboxylase polypeptides may be present in the cell, in the cell culture medium, or prepared in various forms, such as lysates or isolated preparations. As such, in some embodiments, the engineered decarboxylase polypeptide may be an isolated polypeptide.

"Improved enzyme properties" refers to an enzyme property that is better or more desirable for a specific purpose as compared to a reference decarboxylase such as a wild type decarboxylase or another improved engineered decarboxylase. Improved enzyme properties are exhibited by engineered decarboxylase polypeptides in this disclosure. Enzyme properties that are expected to be improved include, but are not limited to, enzyme activity (which can be expressed as a percentage of substrate conversion), thermal stability, solvent stability, pH activity characteristics, cofactor requirements, tolerance to inhibitors (e.g., substrate or product inhibition), stereospecificity and stereoselectivity (including enantioselectivity or diastereoselectivity).

"Conversion" refers to the enzymatic transformation of a substrate to the corresponding product. "Percent conversion" or "conversion" refers to the percentage of substrate that is converted to product within a period of time under the specified conditions. Thus, "enzymatic activity" or "activity" of a decarboxylase polypeptide can be expressed as the "percent conversion" of the substrate to the product.

"Thermostable" means that a decarboxylase polypeptide that retains similar activity (for example more than 50% to 100%) after being exposed to an elevated temperature (e.g., 30-60° C.) for a period of time (0.5-48 h).

"Solvent-stable" refers to a decarboxylase polypeptide that maintains similar activity (for example more than 50% to 80%) after exposure to different concentration (5%-99%) of varying solvent or solvent mixtures (ethanol, isopropanol, dimethylsulfoxide (DMSO), tetrahydrofuran, 2-Methyltetrahydrofuran, acetone, toluene, butyl acetate, methyl tert-butyl ether, etc.) for a period of time (e.g., 0.5-24 hours).

"Suitable reaction conditions" refer to those conditions (e.g., enzyme loading, substrate loading, cofactor loading, temperature, pH, buffer, co-solvent, etc.) in the biocatalytic reaction system, under which the decarboxylase polypeptide of the present disclosure can convert a substrate to a desired product compound. Exemplary "suitable reaction conditions" are provided in the present disclosure and illustrated by examples.

"Hydrocarbyl" refers to a straight or branched aliphatic hydrocarbon chain. The number of subscripts following the symbol "C" specifies the number of carbon atoms that a particular chain may contain. For example, "$C_1$-$C_8$" refers to a straight or branched chain hydrocarbyl group having 1 to 8 carbon atoms. Hydrocarbyl groups may optionally be substituted with one or more substituent groups. "Aryl" means a monovalent aromatic hydrocarbon group of 6 to about 20 carbon atoms. "Heteroaryl" and "heteroaromatic" refer to an aryl group in which one or more of the carbon atoms of the parent aromatic ring system is/are replaced by a heteroatom (O, N, or S). "Substituted", when used to modify a specified group, means that one or more hydrogen atoms of the specified group are each replaced, independently of one another, by identical or different substituents. "Substituted hydrocarbyl, aryl, or heteroaryl" refers to a hydrocarbyl, aryl, or heteroaryl group in which one or more hydrogen atoms are replaced by other substituents. "Optional" or "optionally" means that the described event or circumstance may or may not occur; for example, "optionally substituted aryl" refers to an aryl group that may or may not be substituted. This description includes both substituted aryl groups and unsubstituted aryl groups.

As used herein, "compound" refers to any compound encompassed by the structural formulas and/or chemical names indicated with the compounds disclosed herein. Compounds may be identified by their chemical structure and/or chemical name. When the chemical structure and chemical name conflict, the chemical structure determines the identity of the compound. Unless specifically stated or indicated otherwise, the chemical structures described herein encompass all possible isomeric forms of the described compounds.

2. Engineered Decarboxylase Polypeptides

The present invention provides amino acid sequences of engineered decarboxylase that are useful for catalyzing the conversion of L-Tyrosine to Tyramine as well as the conversion of L-DOPA to Dopamine under industrial-relevant conditions. The present disclosure also provides polynucleotides encoding engineered decarboxylase polypeptides. Compared to the wild type decarboxylase, the engineered decarboxylase polypeptide provided by the invention has better activity and stability, the use of the engineered polypeptides of the present invention for the preparation of Tyramine and Dopamine results in higher unit activity, lower cost, and has good industrial application prospects.

Table 1 below illustrates the engineered decarboxylase polypeptides developed by the present invention. Each row gives the nucleotide sequence number and amino acid sequence number of a particular engineered decarboxylase polypeptide, as well as the residue differences compared to SEQ ID No: 2. The catalytic performance of each of the exemplified engineered decarboxylase polypeptides (the overall performance in the reaction, combining activity and stability) is indicated by "+", with the specific definitions given in Table 2 or Table 3.

TABLE 1

| polynucleotide SEQ ID No | Amino acid SEQ ID No | Amino acid residue difference relative to SEQ ID No: 2 | Catalytic performance |
|---|---|---|---|
| 1 | 2 | — | # |
| 3 | 4 | N517D; | + |
| 5 | 6 | N210L; | + |
| 7 | 8 | A181E; | + |
| 9 | 10 | V317E; | + |
| 11 | 12 | E576K; | + |

TABLE 1-continued

| polynucleotide SEQ ID No | Amino acid SEQ ID No | Amino acid residue difference relative to SEQ ID No: 2 | Catalytic performance |
|---|---|---|---|
| 13 | 14 | V467L; | + |
| 15 | 16 | F380L; | + |
| 17 | 18 | N530D; | + |
| 19 | 20 | K51P; | + |
| 21 | 22 | K51T; | + |
| 23 | 24 | P52T; | + |
| 25 | 26 | P52V; | + |
| 27 | 28 | V535W; | + |
| 29 | 30 | M133V; K465R; | + |
| 31 | 32 | T536G; | + |
| 33 | 34 | S538V; | + |
| 35 | 36 | I271P; | + |
| 37 | 38 | A123S; I271S; | + |
| 39 | 40 | V294A; A376S; | + |
| 41 | 42 | I388T; | + |
| 43 | 44 | K51P; K465V; | ++ |
| 45 | 46 | K51P; V467L; | ++ |
| 47 | 48 | K51P; N210L; N530D; | ++ |
| 49 | 50 | K51P; V294A; V535W; | ++ |
| 51 | 52 | K51P; N530D; | ++ |
| 53 | 54 | K51P; V294A; | ++ |
| 55 | 56 | K51P; N210L; V294A; V535W; | ++ |
| 57 | 58 | K51P; I388T; | ++ |
| 59 | 60 | D30E; K51P; P52S; K72R; | ++ |
| 61 | 62 | D30E; K51P; K72R; | ++ |
| 63 | 64 | D30E; K51P; P52S; | ++ |
| 65 | 66 | Q44R; K51P; A56S; | ++ |
| 67 | 68 | Q44R; K51P; A56T; Q58R; K454R; | ++ |
| 69 | 70 | Q44R; K51P; K454R; | ++ |
| 71 | 72 | K51P; A56S; E63D; K454R; | ++ |
| 73 | 74 | Q44K; K51P; A56P; Q58R; | ++ |
| 75 | 76 | K51P; A56P; Q58R; E63D; | ++ |
| 77 | 78 | K51P; Q58R; K454R; | ++ |
| 79 | 80 | K51P; A56P; Q58R; E63D; K454R; | ++ |
| 81 | 82 | D12Y; K51P; | ++ |
| 83 | 84 | D12T; K51P; | ++ |
| 85 | 86 | Q26T; K51P; | ++ |
| 87 | 88 | Q26F; K51P; | ++ |
| 89 | 90 | Q44I; K51P; | ++ |
| 91 | 92 | Q44L; K51P; | ++ |
| 93 | 94 | K51P; Q58R; | ++ |
| 95 | 96 | K51P; Q58V; | ++ |
| 97 | 98 | K51P; Q58H; | ++ |
| 99 | 100 | K51P; Y147F; | ++ |
| 101 | 102 | K51P; K465L; | ++ |
| 103 | 104 | K51P; K465G; | ++ |

TABLE 2

| Representative symbol | Description of improved catalytic performance of engineered transaminase polypeptide (Measured by the conversion of L-DOPA or L-Tyrosine) | Reaction condition for conversion measurement |
|---|---|---|
| # | Conversion <30%, reaction time ≤6 hours | [30° C., 48 h] Pretreated enzyme solution 20% (v/v), L-DOPA 100 g/L (or L-Tyrosine 100 g/L), PLP 0.2 mM, pH 4.0~pH 6.0, 30° C. |

TABLE 2-continued

| Representative symbol | Description of improved catalytic performance of engineered transaminase polypeptide (Measured by the conversion of L-DOPA or L-Tyrosine) | Reaction condition for conversion measurement |
| --- | --- | --- |
| + | Conversion ≥60%, reaction time ≤6 hours | [30° C., 48 h] Pretreated enzyme solution 20% (v/v), L-DOPA 100 g/L (or L-Tyrosine 100 g/L), PLP 0.2 mM, pH 4.0~pH 6.0, 30° C. |
| ++ | Conversion ≥90%, reaction time ≤6 hours | [30° C., 48 h] Pretreated enzyme solution 20% (v/v), L-DOPA 100 g/L (or L-Tyrosine 100 g/L), PLP 0.2 mM, pH 4.0~pH 6.0, 30° C. |

The pretreatment of enzyme solution in table 2 means that the enzyme solution were kept at 30° C. for 48 hours (as described in example 3). Prior to pretreatment, the enzyme solution had equal amount of decarboxylase polypeptides corresponding to the amino acid sequence in Table 1; the protein concentration in enzyme solution were about 10 g/L ("Bradford method" was employed in measuring the protein concentration).

TABLE 3

| Representative symbol | Description of improved catalytic performance of engineered transaminase polypeptide (Measured by the conversion of L-DOPA or L-Tyrosine) | Reaction condition for conversion measurement |
| --- | --- | --- |
| # | Conversion <25%, reaction time ≤6 hours | Unpretreated enzyme solution 5% (v/v), L-DOPA 100 g/L (or L-Tyrosine 100 g/L), PLP 0.2 mM, pH 4.0~pH 6.0, 30° C. |
| + | Conversion ≥50%, reaction time ≤6 hours | Untreated enzyme solution 5% (v/v), L-DOPA 100 g/L (or L-Tyrosine 100 g/L), PLP 0.2 mM, pH 4.0~pH 6.0, 30° C. |
| ++ | Conversion ≥90%, reaction time ≤6 hours | Untreated enzyme solution 5% (v/v), L-DOPA 100 g/L (or L-Tyrosine 100 g/L), PLP 0.2 mM, pH 4.0~pH 6.0, 30° C. |

The enzyme solution in reaction conditions shown in Table 3 was not pretreated, and the loading of enzyme solution (5%) in reaction was lower than that in Table 2 (20%). For the reactions shown in Table 3, the unpretreated enzyme solution had equal amount of decarboxylase polypeptides corresponding to the amino acid sequence in Table 1; the protein concentration in enzyme solution were about 10 g/L ("Bradford method" was employed in measuring the protein concentration).

3. Polynucleotides, Control Sequences, Expression Vectors and Host Cells that can be Used to Produce Engineered Decarboxylase Polypeptides In another aspect, this disclosure provides polynucleotides encoding engineered polypeptides having decarboxylase activity described herein. The polynucleotides can be linked to one or more heterologous regulatory sequences that control gene expression to produce recombinant polynucleotides that are capable of expressing the engineered polypeptides. Expression constructs comprising a heterologous polynucleotide encoding an engineered decarboxylase may be introduced into a suitable host cell to express the corresponding engineered decarboxylase polypeptide.

As apparent to one skilled in the art, the availability of protein sequences and knowledge of codons corresponding to a variety of amino acids provide an illustration of all possible polynucleotides that encode the protein sequence of interest. The degeneracy of the genetic code, in which the same amino acid is encoded by selectable or synonymous codons, allows for the production of an extremely large number of polynucleotides, all of which encode the engineered decarboxylase polypeptides disclosed herein. Thus, upon determination of a particular amino acid sequence, one skilled in the art can generate any number of different polynucleotides by merely modifying one or more codons in a manner that does not alter the amino acid sequence of the protein. In this regard, this disclosure specifically contemplates each and every possible alteration of a polynucleotide that can be made by selecting a combination based on possible codon selections, for any of the polypeptides disclosed herein, comprising those amino acid sequences of exemplary engineered polypeptides listed in Table 1, and any of the polypeptides disclosed as even sequence identifiers of SEQ ID NO: 2 to 104 in the Sequence Listing incorporated by reference, all of which are believed to be particularly public.

In various embodiments, the codons are preferably selected to accommodate the host cell in which the recombinant protein is produced. For example, codons preferred for bacteria are used to express genes in bacteria; codons preferred for yeast are used to express genes in yeast; and codons preferred for mammals are used for gene expression in mammalian cells.

In some embodiments, the polynucleotides encode polypeptides comprising amino acid sequences that are at least about 80%, 85%, 86%, 87%, 88%, 89%, 90%, 91%, 92%, 93%, 94%, 95%, 96%, 97%, 98%, 99% or more identical to a reference sequence that is an even sequence identifier of SEQ ID NO: 2 to 104, wherein the polypeptides have decarboxylase activity and one or more of the improved properties described herein, for example, the ability to convert compound A1 or A2 to Tyramine or Dopamine respectively, with increased activity compared to the polypeptide of SEQ ID NO: 2.

In some embodiments, the polynucleotides encode engineered decarboxylase polypeptides, wherein the engineered decarboxylase polypeptides comprise amino acid sequences having a percentage of identity described above and having one or more amino acid residue differences as compared to SEQ ID NO: 2. In some embodiments, the present disclosure provides engineered polypeptides having decarboxylase activity, wherein the engineered polypeptides has at least 80% sequence identity to the reference sequence of SEQ ID NO: 2 and comprises a combination of residue difference that is selected from the following positions: X12, X26, X30, X44, X51, X52, X56, X58, X63, X72, X123, X133, X147, X181, X210, X271, X294, X317, X376, X380, X388, X454, X465, X467, X517, X530, X535, X536, X538, X576.

In some embodiments, the polynucleotide encoding the engineered decarboxylase polypeptide comprises sequences having odd sequence identifier of SEQ ID NO:3 to 103.

In some embodiments, the polynucleotides encode polypeptides as described herein; but at the nucleotide level, the polynucleotides have about 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to reference polynucleotides encoding engineered decarboxylase polypeptides as described herein. In some embodiments, the reference polynucleotides are selected from the sequences having the odd sequence identifiers of SEQ ID NO: 3 to 103.

The isolated polynucleotides encoding engineered decarboxylase polypeptides can be manipulated to enable the expression of the engineered polypeptides in a variety of ways, which comprises further modification of the sequences by codon optimization to improve expression, insertion into suitable expression elements with or without additional control sequences, and transformation into a host cell suitable for expression and production of the engineered polypeptides.

Depending on the expression vector, manipulation of the isolated polynucleotide prior to insertion of the isolated polynucleotide into the vector may be desirable or necessary. Techniques for modifying polynucleotides and nucleic acid sequences using recombinant DNA methods are well known in the art. Guidance is provided below: Sambrook et al., 2001, Molecular Cloning: A Laboratory Manual, Third Edition, Cold Spring Harbor Laboratory Press; and Current Protocols in Molecular Biology, Edited by Ausubel. F. et al., ISBN: 978-0-471-50338-5.

In another aspect, this disclosure also relates to recombinant expression vectors, depending on the type of host they are to be introduced into, including a polynucleotide encoding an engineered decarboxylase polypeptide or variant thereof, and one or more expression regulatory regions, such as promoters and terminators, origin of replication and the like. Alternatively, the nucleic acid sequence of the present disclosure can be expressed by inserting the nucleic acid sequence or the nucleic acid construct comprising the sequence into an appropriate expression vector. In generating the expression vector, the coding sequence is located in the vector such that the coding sequence is linked to a suitable control sequence for expression.

The recombinant expression vector can be any vector (e.g., a plasmid or virus) that can be conveniently used in recombinant DNA procedures and can result in the expression of a polynucleotide sequence. The choice of vector will generally depend on the compatibility of the vector with the host cell to be introduced into. The vector can be linear or closed circular plasmid. The expression vector may be an autonomously replicating vector, i.e., a vector that exists as an extrachromosomal entity whose replication is independent of chromosomal replication such as plasmids, extrachromosomal elements, minichromosomes, or artificial chromosomes. The vector may contain any elements for ensuring self-replication. Alternatively, the vector may be a vector that, when introduced into a host cell, integrates into the genome and replicates with the chromosome into which it is integrated. Moreover, a single vector or plasmid or two or more vectors or plasmids that together comprise the total DNA to be introduced into the genome of the host cell may be used.

Many expression vectors useful to the embodiments of the present disclosure are commercially available. An exemplary expression vector can be prepared by inserting a polynucleotide encoding an engineered decarboxylase polypeptide to plasmid pACYC-Duet-1 (Novagen).

In another aspect, this disclosure provides host cells comprising polynucleotides encoding engineered decarboxylase polypeptides of the present disclosure. The polynucleotide is linked to one or more control sequences for expression of decarboxylase polypeptides in a host cell. Host cells for expression of polypeptides encoded by the expression vectors of the present disclosure are well known in the art, including, but not limited to, bacterial cells such as *E. coli, Arthrobacter* KNK168, *Streptomyces*, and *Salmonella typhimurium* cells; fungal cells such as yeast cells (e.g., *Saccharomyces cerevisiae* or *Pichia pastoris*); insect cells such as *Drosophila* S2 and *Spodoptera* Sf9 cells; animal cells such as CHO, COS, BHK, 293 and Bowes melanoma cells; and plant cells. An exemplary host cell is *E. coli* BL21 (DE3). The above host cells may be wild type or may be engineered cells through genomic edition, such as knockout of the wild type decarboxylase gene carried in the host cell's genome. Suitable media and growth conditions for the above host cells are well known in the art.

Polynucleotides used to express engineered decarboxylases can be introduced into cells by a variety of methods known in the art. Techniques comprise, among others, electroporation, bio-particle bombardment, liposome-mediated transfection, calcium chloride transfection, and protoplast fusion. Different methods of introducing polynucleotides into cells are obvious to those skilled in the art.

4. Process of Producing an Engineered Decarboxylase Polypeptide

Engineered decarboxylase can be developed by subjecting a polynucleotide encoding a decarboxylase to mutagenesis and/or directed evolution. An illustration of direction evolution technique can be found in "Biocatalysis for the Pharmaceutical Industry: Discovery, Development, and Manufacturing" (2009 John Wiley & Sons Asia (Pte) Ltd. ISBN: 978-0-470-82314-9).

When the sequence of an engineered polypeptide is known, the encoding polynucleotide may be prepared by standard solid-phase methods according to known synthetic methods. In some embodiments, fragments of up to about 100 bases can be synthesized separately and then ligated (e.g., by enzymatic or chemical ligation methods or polymerase-mediated methods) to form any desired contiguous sequence. For example, the polynucleotides and oligonucleotides of the present disclosure can be prepared by chemical synthesis using, for example, the classic phosphoramidite methods described by Beaucage et al., 1981, Tet Lett 22: 1859-69, or Matthes et al. People, 1984, EMBO J. 3: 801-05, as typically practiced in automated synthesis methods. According to the phosphoramidite method, oligonucleotides are synthesized, purified, annealed, ligated, and cloned into a suitable vector, for example, in an automated DNA synthesizer. In addition, essentially any nucleic acid is available from any of a variety of commercial sources.

In some embodiments, the present disclosure also provides a process for preparing or producing an engineered decarboxylase polypeptide that is capable of converting compound A1 or A2 to Tyramine or Dopamine respectively, under suitable reaction conditions, wherein the process comprises culturing a host cell capable of expressing a polynucleotide encoding an engineered polypeptide under culture conditions suitable for the expression of the polypeptide, and these host cells can be directly applied to the process of converting the compound A1 or A2 to Tyramine or Dopamine respectively, in the form of wet cells. In some embodiments, the process of preparing a polypeptide further comprises isolating the polypeptide. Engineered polypeptides may be expressed in suitable cells and isolated (or recovered) from the host cell and/or culture medium using any one or more of the well-known techniques for protein purification, the techniques for protein purification include, among others, lysozyme treatment, ultrasonication, homogenization, filtration, salting out, ultracentrifugation and chromatography.

5. Methods of Using an Engineered Decarboxylase and Compounds Prepared Therewith In another aspect, the engineered decarboxylase polypeptides described herein can catalyze the decarboxylation of an amino acid to form an amino compound. The present disclosure also provides process of preparing a wide range of compounds (I) or structural analogs thereof using an engineered decarboxylase polypeptide disclosed herein. In some embodiments, engineered decarboxylase polypeptides can be used in a process of preparing a compound of structural formula (I):

(I)

wherein R is optionally substituted or unsubstituted $C_1$-$C_8$ alkyl, or optionally substituted or unsubstituted aryl or heteroaryl; the process herein comprises that, under suitable reaction conditions, the amino acid substrate of formula (II)

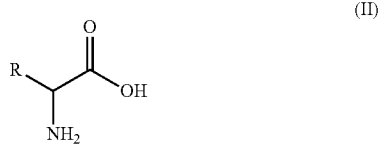

(II)

are contacted with decarboxylase polypeptide, wherein the decarboxylase polypeptide is an engineered decarboxylase polypeptide described herein. In some embodiments, the engineered decarboxylase polypeptide has at least 80%, 85%, 86%, 87%, 88%, 89%, 90%, 91%, 92%, 93%, 94%, 95%, 96%, 97%, 98%, 99% or more of sequence identity with the reference amino acid sequence selected from any one of the even numbered sequences of SEQ ID NO:2-104, and are capable of converting a compound of formula (II) to the compound of formula (I) with a higher conversion rate than SEQ ID NO:2.

As noted above, decarboxylase polypeptides useful in the process of the present disclosure may be characterized according to the ability of converting L-DOPA to Dopamine or the ability of converting L-Tyrosine to Tyramine. Thus, in any of the embodiments of the process disclosed herein, the process may be carried out, wherein the decarboxylase polypeptide is capable of converting L-DOPA to Dopamine with better catalytic performance than SEQ ID NO:2, and have at least 80%, 85%, 86%, 87%, 88%, 89%, 90%, 91%, 92%, 93%, 94%, 95%, 96%, 97%, 98%, 99% or more of sequence identity with the reference amino acid sequence selected from any one of the even numbered sequences of SEQ ID NO:2-104.

In some embodiments of the process, the compound of formula (I) is

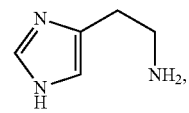

and the substrate of formula (II) is

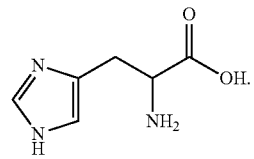 [SMILES: NC(Cc1c[nH]cn1)C(=O)O]

In some embodiments of the process, the compound of formula (I) is

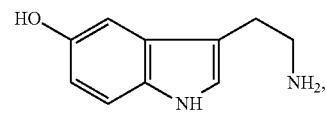

and the substrate of formula (II) is

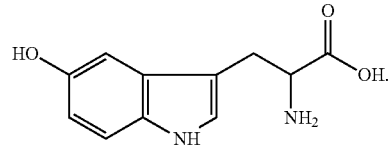 [SMILES: NC(Cc1c[nH]c2ccc(O)cc12)C(=O)O]

In some embodiments of the process, the compound of formula (I) is

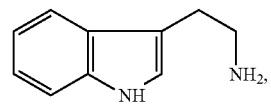 [SMILES: NCCc1c[nH]c2ccccc12]

and the substrate of formula (II) is

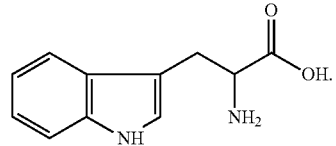 [SMILES: NC(Cc1c[nH]c2ccccc12)C(=O)O]

In some embodiments of the process, the compound of formula (I) is

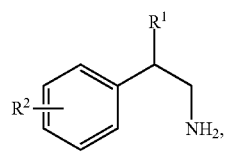

wherein R¹ is —H, —CH₂OH, —CH₂SH, —CH₂SCH₃ or an optionally substituted C₁-C₄ hydrocarbon group, R² is a C₁-C₄-hydrocarbyl, —H, a halogen (such as —F, —Cl, —Br and —I), —NO₂, —NO, —SO₂R' or —SOR', —S R', —N R'R', —O R', —CO₂R' or —COR', —C(O)NR', —SO₂ NH₂ or —SO NH₂, —CN, CF₃, wherein each R' is independently selected from —H or (C₁-C₄)hydrocarbyl;
and the substrate of formula (II) is

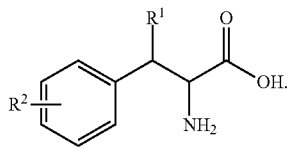

In some embodiments, R² is in the para position of the phenyl ring. In some embodiments, R² is in the meta position of the phenyl ring. In some embodiments, R² is in the ortho position of the phenyl ring. In some embodiments, R² is simultaneously in the para and meta positions of the phenyl ring. In some embodiments, R² is simultaneously in the para and ortho positions of the phenyl ring. In some embodiments, R² is simultaneously at the meta and ortho positions of the phenyl ring.

In some embodiments of the process, the compound of formula (I) is

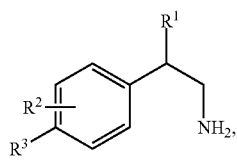

wherein R³ is R² as defined above, R² and R¹ are as defined above. The substrate of formula (II) is

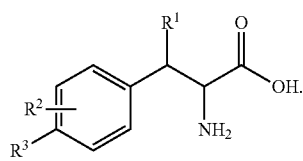

In some embodiments, R² is in the meta position of the phenyl ring. In some embodiments, R² is ortho to the phenyl ring. In some embodiments of the process, the compound of formula (I) is

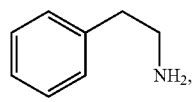

and the substrate of formula (II) is

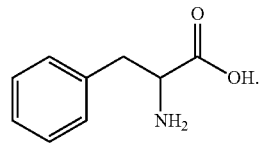 [SMILES: NC(Cc1ccccc1)C(=O)O]

In some embodiments, the engineered decarboxylase polypeptides can be used in a process of preparing Tyramine:

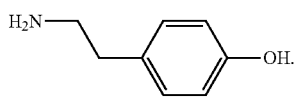

Tyramine

In these embodiments, the process herein comprises that, under suitable reaction conditions, the compound of formula A1

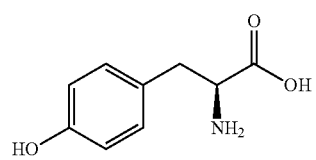

A1 is contacted with the engineered decarboxylase polypeptides disclosed herein.

In some embodiments, the engineered decarboxylase polypeptides can be used in a process of preparing Dopamine:

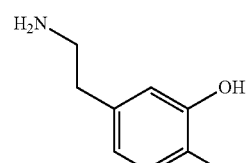

Dopamine

In these embodiments, the process herein comprises that, under suitable reaction conditions, the compound of formula A2

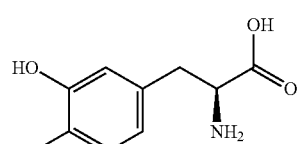

A2 is contacted with the engineered decarboxylase polypeptides disclosed herein.

Specific embodiments of engineered decarboxylase polypeptides for use in the process are further provided in the detailed description. Engineered decarboxylase polypeptides that can be used in the above processes comprise amino acid sequences selected from SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104.

As described herein and exemplified in the examples, the present disclosure contemplates a range of suitable reaction conditions that may be used in the process herein, including but not limited to pH, temperature, buffers, solvent systems, substrate loadings, polypeptide loading, and reaction time. Additional suitable reaction conditions for performing a method of enzymatically converting substrate compounds to a product compound using engineered decarboxylase polypeptides described herein can be readily optimized by routine experimentation, which including but not limited to that the engineered decarboxylase polypeptide is contacted with substrate compounds under experimental reaction conditions of varying concentration, pH, temperature, solvent conditions, and the product compound is detected, for example, using the methods described in the examples provided herein.

As described above, engineered polypeptides having decarboxylase activity for use in the process of the present disclosure generally comprises amino acid sequences that have at least 80%, 85%, 86%, 87%, 88%, 89%, 90%, 91%, 92%, 93%, 94%, 95%, 96%, 97%, 98% or 99% sequence identity to the reference amino acid sequence selected from any one of the even numbered sequences of SEQ ID NO: 2 to 104.

The substrate compounds in the reaction mixture can be varied, taking into consideration of, for example, the amount of the desired product compound, the effect of the substrate concentration on the enzyme activity, the stability of the enzyme under the reaction conditions, and the percent conversion of substrate to product. In some embodiments of the process, the suitable reaction conditions include at least about 0.5 to about 400 g/L, about 1 to about 400 g/L, about 5 to about 400 g/L, about 10 to about 400 g/L, or about 50 to about 400 g/L of loading of substrate (II), substrate A1 or A2. In some embodiments, suitable reaction conditions include at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L, at least about 200 g/L, at least about 250 g/L, at least about 300 g/L, at least about 350 g/L, at least about 400 g/L or more of loading of substrate (II), substrate A1 or substrate A2. The values for the substrate loading provided herein are based on the molecular weight of compound (II) or A1 or A2, however it is also contemplated that the equivalent molar amounts of various hydrates and salts of compound (II) or A1 or A2 may also be used in the process.

Suitable reaction conditions for the process generally also include the presence of a cofactor in the reaction mixture. Because the engineered decarboxylase typically use members of the vitamin B6 family, the reaction conditions may include one or more compounds selected from pyridoxal-5'-phosphate (also known as pyridoxal phosphate, PLP, P5P), pyridoxine (PN), Pyridoxal (PL), pyrilamine (PM), and their phosphorylated counterparts; pyridoxine phosphate (PNP), and pyridoxamine phosphate (PMP). In some embodiments, suitable reaction conditions may include a cofactor selected from the group consisting of PLP, PN, PL, PM, PNP, and PMP, at a concentration of about 0.01 g/L to about 10 g/L, about 0.02 g/L to about 5 g/L, about 0.05 g/L to about 2.5 g/L. In some embodiments, the cofactor is PLP.

Accordingly, in some embodiments, suitable reaction conditions may include cofactor PLP at a concentration of about 0.01 g/L to about 10 g/L, about 0.02 g/L to about 5 g/L or about 0.05 g/L to about 2.5 g. In some embodiments, the reaction conditions include about 10 g/L or less, about 5 g/L or less, about 1.0 g/L or less, about 0.1 g/L or less, about 0.05 g/L or less, or about 0.02 g/L or less of a PLP concentration.

In some embodiments of the reaction (e.g., where whole cells or lysates are used), the cofactor is present naturally in the cell extract and does not need to be supplemented. In some embodiments of the process (e.g., using partially purified, or purified decarboxylase), the process may further comprise the step of adding a cofactor to the enzymatic reaction mixture. In some embodiments, the cofactor is added at the beginning of the reaction and/or additional cofactor is added during the reaction.

In the embodiments of the reaction, the reaction conditions may include a suitable pH. As noted above, the desired pH or desired pH range can be maintained by using an acid or base, a suitable buffer, or a combination of buffer and added acid or base. The pH of the reaction mixture can be controlled before and/or during the reaction. In some embodiments, suitable reaction conditions include a solution pH of about 3.0 to about 8.0, a pH of about 4.0 to about 6.0. In some embodiments, the reaction conditions include a solution pH of about 3.0, 3.5, 4.0, 4.5, 5.0, 5.5, 6.0, 6.5, 7.0, 7.5 or 8.0.

In embodiments of the processes herein, suitable temperatures can be used for the reaction conditions, taking into consideration of, for example, the increase in reaction rate at higher temperatures, the activity of the enzyme for sufficient duration of the reaction. Accordingly, in some embodiments, suitable reaction conditions include a temperature of about 10° C. to about 60° C., about 25° C. to about 50° C., about 25° C. to about 40° C., or about 25° C. to about 30° C. In some embodiments, suitable reaction temperatures include a temperature of about 25° C., 30° C., 35° C., 40° C., 45° C., 50° C., 55° C., or 60° C. In some embodiments, the temperature during the enzymatic reaction can be maintained at a certain temperature throughout the reaction. In some embodiments, the temperature during the enzymatic reaction may be adjusted over a temperature profile during the course of the reaction.

The processes of using the engineered decarboxylase are generally carried out in a solvent. Suitable solvents include water, aqueous buffer solutions, organic solvents, and/or co-solvent systems, which generally include mixtures of aqueous solvents and organic solvents. The aqueous solutions (water or aqueous co-solvent systems) can be pH-buffered or unbuffered. In some embodiments, the processes of using an engineered decarboxylase polypeptide are generally carried out in an aqueous co-solvent system comprising an organic solvent (e.g., methanol, ethanol, propanol, isopropanol (IPA), dimethyl sulfoxide (DMSO), dimethylformamide (DMF), isopropyl acetate, ethyl acetate, butyl acetate, 1-octanol, heptane, octane, methyl tert-butyl ether (MTBE), Toluene, etc.), ionic liquids (for example, 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of the aqueous co-solvent system may be miscible with the aqueous component, providing a single liquid phase, or may be partially miscible or immiscible with the aqueous component, providing two liquid phases. The carbon dioxide generated during the decarboxylation reaction may cause foam formation, and an antifoaming agent may be appropriately added. Exemplary aqueous co-solvent system comprises water and one or more organic solvents. In general, the organic solvent component of the aqueous co-solvent system is selected such that it does not completely inactivate the decarboxylase. Suitable co-solvent system can be readily identified by measuring the enzymatic activity of a particular engineered decarboxylase with a defined substrate of interest in the candidate solvent system, utilizing enzymatic activity assays, such as those described herein. In some embodiments of the process, suitable reaction conditions include an aqueous co-solvent comprising ethanol at a concentration of about 1% to about 100% (v/v), about 1% to about 60% (v/v), about 2% to about 60% (v/v), about 5% to about 60% (v/v), from about 10% to about 60% (v/v), from about 10% to about 50% (v/v), or about 10% to about 40% (v/v). In some embodiments of the process, suitable reaction conditions include an aqueous co-solvent comprising ethanol at a concentration of at least about 1%, 5%, 10%, 15%, 20%, 25%, 30%, 35%, 40%, 45%, 50%, 55%, or 60% (v/v).

Suitable reaction conditions can include a combination of reaction parameters that provide for the biocatalytic conversion of the substrate compounds to its corresponding product compound. Accordingly, in some embodiments of the process, the combination of reaction parameters comprises: (a) substrate A1 or A2 loading of about 10 g/L to about 200 g/L; (b) engineered polypeptide concentration of about 0.5 g/L to 10 g/L; (c) pH of about 3.0 to 8.0; and (d) temperature of about 10° C. to 60° C.

Exemplary reaction conditions include the assay conditions provided in Table 2, Table 3, Example 7 and Example 8.

In carrying out the decarboxylation reaction described herein, the engineered decarboxylase polypeptide may be added to the reaction mixture in the partially purified or purified forms, whole cells transformed with the gene encoding the engineered decarboxylase polypeptide, and/or as cell extracts and/or lysates of such cells. Whole cells transformed with the gene encoding the engineered decarboxylase or cell extracts, lysates thereof, and isolated enzymes can be used in a wide variety of different forms, including solids (e.g., lyophilized, spray dried, or the like) or semi-solid (e.g., a crude paste such as wet cells). The cell extract or cell lysate may be partially purified by precipitation (e.g., ammonium sulfate, polyethyleneimine, heat treatment or the like), followed by desalting procedures (e.g., ultrafiltration, dialysis, and the like) prior to lyophilization. Any of the enzyme preparations can be stabilized by crosslinking using known crosslinking agents, such as glutaraldehyde, or immobilization to a solid phase material (such as a resin).

In some embodiments of the decarboxylation reactions described herein, the reaction is performed under suitable reaction conditions described herein, wherein the engineered decarboxylase polypeptide is immobilized to a solid support. Solid supports useful for immobilizing the engineered decarboxylase enzyme for carrying out the reaction include but are not limited to beads or resins such as polymethacrylates with epoxy functional groups, polymethacrylates with amino epoxy functional groups, polymethacrylates, styrene/DVB copolymer or polymethacrylates with octadecyl functional groups. Exemplary solid supports include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, wherein an engineered polypeptide is expressed in the form of a secreted polypeptide, a culture medium containing the secreted polypeptide can be used in the process herein.

In some embodiments, the solid reactants (e.g., enzymes, salts, etc.) can be provided to the reaction in a variety of different forms, including powders (e.g., lyophilized, spray dried, etc.), solutions, emulsions, suspensions and the like. The reactants can be readily lyophilized or spray-dried using methods and instrumentation known to one skilled in the art. For example, the protein solution can be frozen at −80° C. in small aliquots, and then added to the pre-chilled lyophilization chamber, followed by the application of a vacuum.

In some embodiments, the order of addition of reactants is not critical. The reactants may be added together to the solvent at the same time (e.g., monophasic solvent, a biphasic aqueous co-solvent system, etc.), or alternatively, some reactants may be added separately, and some may be added together at different time points. For example, the decarboxylase and substrate may be added first to the reaction solution; the organic phase can then be added and mixed. Alternatively, the substrates can be premixed in the organic phase prior to addition to the aqueous phase.

EXAMPLES

The following examples further illustrate the present invention, but the present invention is not limited thereto. In the following examples, experimental methods with conditions not specified, were conducted at the commonly used conditions or according to the suppliers' suggestion.

Example 1: Gene Cloning and Construction of Expression Vectors

The amino acid sequence of the wild type decarboxylase from *Streptococcus thermophilus* can be retrieved from NCBI, and the corresponding nucleic acids were then synthesized by a vendor using conventional techniques in the art and cloned into the expression vector pACYC-Duet-1. The recombinant expression plasmid was transformed into *E. coli* BL21 (DE3) competent cells under the conditions of 42° C. thermal shock for 90 seconds. The transformation solution was plated on LB agar plates containing chloramphenicol which was then incubated overnight at 37° C. to obtain recombinant transformants.

Example 2: Expression of a Decarboxylase Polypeptide and Preparation of Enzyme Solution of Decarboxylase Polypeptide A recombinant *E. coli* strain expressing decarboxylase polypeptide was inoculated into 50 mL of LB medium containing chloramphenicol (peptone 10 g/L, yeast extract powder 5 g/L, chlorinated sodium 10 g/L, pH 7.0±0.2, 25° C.) in a 250 mL Erlenmeyer flask. which was then cultured in a shaking incubator at 30° C., 250 rpm overnight. When the $OD_{600}$ of this overnight culture reached 2, it was subcultured at the inoculum of 5% (v/v) into a 1000 mL Erlenmeyer flask containing 250 mL of TB medium (tryptone 12 g/L, yeast extract powder 24 g/L, disodium hydrogen phosphate 9.4 g/L, dipotassium hydrogen phosphate 2.2 g/L, pH 7.2±0.2, 30° C.). It was shaken at 30° C., 250 rpm in a shaking incubator. When the $OD_{600}$ of subculture broth reached 0.6~0.8, IPTG was added to induce the expression of decarboxylase at a final concentration of 1 mM. After induction the expression was performed for 20 h, the culture broth was centrifuged (8000 rpm, 10 minutes); the supernatant was discarded after centrifugation, and the cell pellet was collected to obtain wet cells.

The wet cells were re-suspended in 30 mL of phosphate buffer (0.05M PBS, pH 7.0), sonicated in an ice bath to produce cell lysate. The cell lysate was centrifuged (8000 rpm, 10 minutes), and the clear supernatant was collected as an enzyme solution of decarboxylase polypeptide. The enzyme solution can be used directly in the reaction or subject to pretreatment.

According to the recombinant expression process using shaking flasks as mentioned above, a miniaturized expression process in 96-well plate was performed by proportionally reducing the scale and the culture broth was centrifuged to obtain wet cells. The wet cells can be lysed by a chemical method commonly known in this field, and enzyme solution can be obtained as clear supernatant after centrifuging the cell lysate.

Example 3: Pretreatment of Enzyme Solution

The enzyme solution obtained in Example 2 was kept in a water bath at 30° C. with stirring for 48 hours. After this treatment, it was centrifuged (8000 rpm, 10 minutes) and the clear supernatant was collected to obtain a pretreated enzyme solution of the decarboxylase polypeptide.

Example 4: Analytical Method

HPLC analysis of L-DOPA and dopamine: The analytical column was an Ultimate-LP-C18 reversed-phase silica gel column with a mobile phase of 20 mM ammonium acetate: acetonitrile=95:5, flow rate was 1.5 mL/min, and a detection wavelength of 280 nm. The retention time of dopamine was 1.97 min and the retention time of L-DOPA was 1.43 min.

HPLC analysis method of L-tyrosine and tyramine: The analytical column was a Moon-Ultimate-LP-C18 reversed phase silica gel column with a mobile phase of 0.1% aqueous acetic acid:acetonitrile=50:50, flow rate of 1.5 mL/min, The detection wavelength was 280 nm, the retention time of tyramine was 0.7 min, and the retention time of L-tyrosine was 1.6 min.

Example 5: Construction of a Decarboxylase Mutant Library

Quikchange kit (supplier: Agilent) was preferably used here. The sequence design of the mutagenesis primers was performed according to the instructions of the kit. The construction of a site-saturation mutagenesis library is as following. The PCR system consisted of 10 µl of 5× Buffer, 1 µl of 10 mM dNTP, 1 µl of plasmid DNA template (50 ng/µl), 0.75 µl (10 uM) each of the upstream and downstream primers, 0.5 µl of high fidelity enzyme and 36 µl of ddH$_2$O. The PCR primer has a NNK degenerated codon at the mutation position. PCR amplification steps: (1) 98° C. pre-denaturation 3 min; (2) 98° C. denaturation 10 s; (3) annealing and extension 3 min at 72° C.; steps of (2)~(3) repeated 25 times; (5) extension 10 min at 72° C.; (6) cooling to 4° C., 2 µl of DpnI was added to the PCR product and the plasmid template was eliminated by overnight digestion at 37° C. The digested PCR product was transformed into *E. coli* BL21 (DE3) competent cells and plated on LB agar plates containing chloramphenicol to obtain a site-saturation mutagenesis library.

Example 6: Screening of Mutant Enzyme Library

Mutant colonies were picked from the agar plates, inoculated into LB medium containing chloramphenicol in a 96-well shallow plate (200 µl LB medium per well), and cultured overnight (18 to 20 hours) at 180 rpm, 80% humidity, 30° C. When the OD$_{600}$ of the overnight culture reached 2-3, 20 µl of this culture were used to inoculate a TB medium containing chloramphenicol in a 96-well deep-well plate (400 µl TB medium per well) as expression culture, and it was shaken at 250 rpm in a shaking incubator under 30° C. and humidity of 80%. When the OD$_{600}$ of the expression culture reached 0.6-0.8, IPTG was added at the final concentration of 0.2 mM to induce expression, and the expression undertook at 250 rpm, humidity of 80%, and 30° C. overnight (18-20 hr). Once the overnight expression was done, the expression culture was centrifuged at 4000 rpm for 10 min to collect cell pellets (i.e. wet cells). 200 µL of lysis buffer (100 mM phosphate buffer, pH 7.5, containing 1 mg/mL lysozyme) was added to each well to break the cells, then the cell lysate was centrifuged and clear supernatant was collected to obtain the enzyme solution. Next, the enzyme solution was put in a shaking water bath at 30° C., 250 rpm for 48 hours to perform the pretreatment. After the pretreatment, the enzyme solution was centrifuged at 4000 rpm for 15 minutes, and 100 µL of supernatant was transferred to a 96-well plate pre-loaded with reaction solution (substrate 50 g/L, 0.5 M ammonium phosphate-phosphate buffer, 0.2 mM PLP, pH 5.0). The reaction plate was placed in a shaking incubator at 30° C. for 24 hours. Finally, samples from each well of reaction plate was analyzed by the method of Example 4.

Example 7: Process of Dopamine Production Catalyzed by Engineered Decarboxylase Polypeptide In a 0.5 M ammonium phosphate-phosphate buffer (pH 5.5), 5% (v/v) of the enzyme solution containing the SEQ ID No: 100 decarboxylase polypeptide were added to reach the final protein concentration of 0.5 g/L (measurement of protein concentration was according to the Bradford method which is well known in the art). L-DOPA was added at a final concentration of 100 g/L, and pyridoxal phosphate was added at a final concentration of 0.2 mM. The reaction proceeded at 30° C. with stirring speed of 400 rpm, and nitrogen was blown during the reaction to avoid oxidation of the product dopamine. After 6 hours of reaction, the conversion of L-DOPA to dopamine was ≥95%.

Example 8: Process of Tyramine Production Catalyzed by Engineered Decarboxylase Polypeptide In 0.5 M ammonium phosphate-phosphate buffer (pH 5.5), 5% (v/v) of the enzyme solution containing the SEQ ID No: 80 decarboxylase polypeptide were added to reach the final protein concentration of 0.5 g/L (measurement of protein concentration was according to the Bradford method which is well known in the art). L-tyrosine was added at a final concentration of 100 g/L, and pyridoxal phosphate was added at a final concentration of 0.2 mM. The reaction proceeded at 30° C. with stirring speed of 400 rpm. After 6 hours of reaction, the conversion of L-tyrosine to tyramine was ≥95%.

Example 9: Reaction Process for Producing Dopamine Catalyzed by Decarboxylase Polypeptide In a 0.5 M ammonium phosphate-phosphate buffer (pH 5.5), 20% (v/v) of the enzyme solution containing the decarboxylase polypeptide of SEQ ID No: 2 were added to reach the final protein concentration of 2 g/L (measurement of protein concentration was according to the Bradford method which is well known in the art). L-DOPA was added at a final concentration of 100 g/L, and pyridoxal phosphate was added at a final concentration of 0.2 mM. The reaction proceeded at 30° C. with stirring speed of 400 rpm, and nitrogen was blown in the solution during the reaction to avoid oxidation of the product dopamine. After 6 hours of reaction, the conversion of L-DOPA to dopamine was about 90%.

Example 10: Preparation of Dopamine Catalyzed by Pretreated Decarboxylase Polypeptide The freshly prepared enzyme solution containing SEQ ID No: 2 decarboxylase polypeptide (total protein concentration of 10 g/L) was pretreated at 30° C. for 48 hours, and then the above pretreated enzyme solution were added in 0.5 M ammonium phosphate-phosphate buffer (pH 5.5) at the final volume concentration of 20% (v/v). L-DOPA was added at a final concentration of 100 g/L of and pyridoxal phosphate was added at a final concentration of 0.2 mM. The reaction proceeded at 30° C. with stirring speed of 400 rpm, and nitrogen was blown in the solution during the reaction to avoid oxidation of the product dopamine. After 6 hours of reaction, the conversion of L-DOPA to dopamine was about 26%.

Example 11: Preparation of Dopamine Catalyzed by a Pretreated Engineered Decarboxylase Polypeptide The freshly prepared enzyme solution containing SEQ ID No: 100 polypeptide (total protein concentration of 10 g/L) was pretreated at 30° C. for 48 hours, and then the above pretreated enzyme solution were added in 0.5 M ammonium phosphate-phosphate buffer (pH 5.5) at the final volume concentration of 10% (v/v). L-DOPA was added at a final concentration of 100 g/L and pyridoxal phosphate was added at a final concentration of 0.2 mM. The reaction proceeded at 30° C. with stirring speed of 400 rpm, and nitrogen was blown during the reaction to avoid oxidation of the product dopamine. After 6 hours of reaction, the conversion of L-DOPA to dopamine was ≥95%.

Example 12: Fermentation Process for the Expression of Engineered Decarboxylase Polypeptide A single colony of *E. coli* BL21 (DE3) containing a plasmid bearing the gene of target engineered decarboxylase was inoculated into 50 mL LB broth containing 30 μg/mL chloramphenicol (5.0 g/L Yeast Extract, 10 g/L Tryptone, 10 g/L sodium chloride). Cells were incubated overnight (at least 16 hours) with shaking at 250 rpm in a 30° C. shaker. When the $OD_{600}$ of the culture reached 1.4 to 2.0, the cells were removed from the incubator and used immediately or stored at 4° C.

A 5 L fermentor containing 2.0 L of growth medium was sterilized in a 121° C. autoclave for 30 minutes. The fermenter was inoculated with the abovementioned overnight cultured *E. coli* (grown in shake flasks as described above to an initial $OD_{600}$ of 1.4 to 2.0). Temperature of fermentor was maintained at 30° C. with jacketed circulating water. The growth medium in fermentor was agitated at 200-800 rpm and air was supplied to the fermentation vessel at 2-8 L/min to maintain the dissolved oxygen level at 40% saturated or greater. The culture was maintained at pH 7.0 by addition of 25-28% v/v ammonium hydroxide. Cell growth was maintained by feeding a feed solution containing 500 g/L of dextrose glucose monohydrate, 12 g/L of ammonium chloride, and 5 g/L of magnesium sulfate heptahydrate. After the $OD_{600}$ of culture reached 25±5, the temperature of fermentor was maintained at 30° C., and the expression of decarboxylase polypeptides was induced by the addition of isopropyl-β-D-thiogalactoside (IPTG) to a final concentration of 1 mM. Fermentation process then continued for additional 18 hours. cells were harvested using a Thermo MuLtifuge X3R centrifuge at 8000 rpm for 10 minutes at 4° C.

It should be understood that after reading the above contents of the present invention, those skilled in the art may make various modifications or additional changes to the present invention. And these equivalent forms also fall within the scope of the appended claims of the present invention.

The invention claimed is:

1. An engineered decarboxylase polypeptide which is, under suitable reaction conditions, capable of (a) catalyzing the decarboxylation of L-tyrosine to produce tyramine, or (b) catalyzing the decarboxylation of L-DOPA to produce dopamine, wherein said polypeptide comprises an amino acid sequence selected from the group consisting of SEQ ID NO: 20, 44, 46, 48, 50, 52, 56, 58, 60, 62, 64, 66, 68, 70, 72, 74, 76, 78, 80, 82, 84, 86, 88, 90, 92, 94, 96, 98, 100, 102 and 104.

2. The engineered decarboxylase polypeptide of claim 1, wherein said suitable reaction conditions include a loading of about 5 g/L to 400 g/L of L-tyrosine or L-DOPA, at a pH of about 3.0-8.0, and at a temperature of about 10-60° C.

3. An engineered polypeptide having decarboxylase activity and comprising an amino acid sequence selected from the group consisting of SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, and 104.

4. A polypeptide immobilized on a solid material by a covalent chemical method or a physical adsorption method, wherein the polypeptide is the engineered decarboxylase polypeptide according to claim 1.

5. The engineered decarboxylase polypeptide of claim 1, wherein said polypeptide comprises the amino acid sequence set forth in SEQ ID NO: 20.

6. A process of preparing a compound of formula (I):

(I)

wherein R is an optionally substituted or unsubstituted $C_1$-$C_8$ hydrocarbyl; or an optionally substituted or unsubstituted aryl or heteroaryl, said process comprising the steps of contacting an amino acid substrate of formula (II)

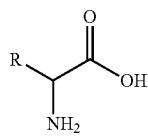

(II)

with the engineered polypeptide of claim 1, under suitable reaction conditions.

7. The process of claim 6, wherein the compound of formula (I) is:

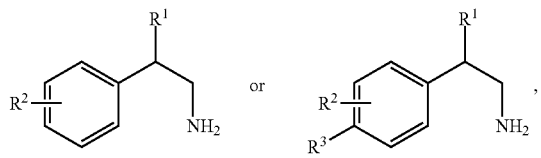

wherein:

$R^1$ is —H, —$CH_2OH$, $CH_2SH$, —$CH_2SCH_3$ or an optionally substituted or unsubstituted $C_1$-$C_4$ hydrocarbyl;

$R^2$ is a $C_1$-$C_4$ hydrocarbyl, —H, a halogen selected from the group consisting of —F, —Cl, —Br and —I, —$NO_2$, —NO, —$SO_2R'$, —SOR', —SR', —NR'R, —OR', —$CO_2R'$, —COR', —C(O)NR', —$SO_2NH_2$, —$SONH_2$, —CN, or —$CF_3$, wherein each R' is independently selected from —H or a $C_1$-$C_4$ hydrocarbyl; and $R^3$ is a $C_1$-$C_4$ hydrocarbyl, —H, a halogen selected from the group consisting of —F, —Cl, —Br and —I, —$NO_2$, —NO, —$SO_2R'$, —SOR', —SR', —NR'R, —OR', —$CO_2R'$, —COR', —C(O)NR', —$SO_2NH_2$, —$SONH_2$, —CN, or —$CF_3$, wherein each R' is independently selected from —H or a $C_1$-$C_4$ hydrocarbyl; and the amino acid substrate of formula (II) is:

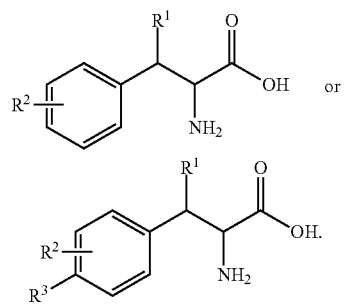

8. The process of claim 7, wherein $R^2$ is (a) in the para position of the phenyl ring, (b) in the meta position of the phenyl ring, (c) in the ortho position of the phenyl ring, (d) in both the para and meta positions of the phenyl ring, (e) in both the para and ortho positions of the phenyl ring, or (f) in both the meta and ortho positions of the phenyl ring.

9. The process of claim 6, wherein the compound of formula (I) is:

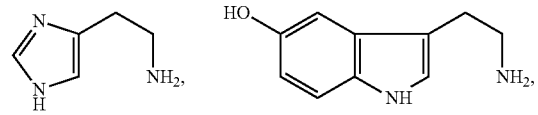

-continued

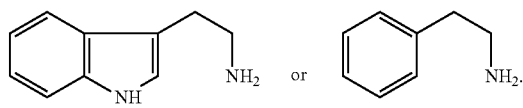

10. A process of preparing tyramine:

Tyramine the process comprising the step of contacting the compound of formula A1

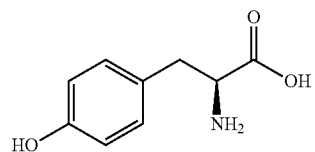

A1 with the engineered decarboxylase polypeptide of claim 1, under suitable reaction conditions.

11. A process of preparing dopamine:

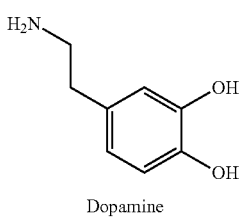 [SMILES: NCCc1ccc(O)c(O)c1]

Dopamine said process comprising the step of contacting the compound of formula A2

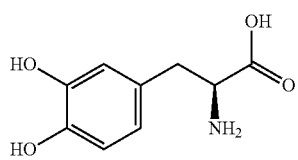

A2 with the engineered decarboxylase polypeptide of claim 1, under suitable reaction conditions.

12. The process of claim 6, wherein the reaction is carried out in a solvent selected from the group consisting of water, methanol, ethanol, propanol, isopropanol, isopropyl acetate, dimethylsulfoxide (DMSO) and dimethylformamide (DMF).

13. The process of claim 6, wherein the reaction conditions comprise a temperature of 10° C. to 60° C.

14. The process of claim 6, wherein the reaction conditions comprise a pH of 3.0 to 8.0.

15. The process of claim 6, wherein the substrate is present at a loading of 5 g/L to 400 g/L.

\* \* \* \* \*

SEQUENCE LISTING

```
<160> NUMBER OF SEQ ID NOS: 104

<210> SEQ ID NO 1
<211> LENGTH: 1863
<212> TYPE: DNA
<213> ORGANISM: Artificial sequence
<220> FEATURE:
<223> OTHER INFORMATION: Engineered sequence

<400> SEQUENCE: 1
atgagcaaca ccagtttcag cgcaaaagat accgatctga gtgcactgtt tatcggtgac         60
aaagcagaaa atggtcagct gtataaggac ctgctgggca aactggttga tgaacatctg        120
ggttggcgcc agaattatat gccgcaggat aaaccgatga tcagcgccga acagcagacc        180
agcccggaat tcgtggtac cgtgaataat atgaaggacg ttctggatga gctgagcagt        240
cgcctgcgta gtcagagcgt tccgtggcat aatgccggtc gttattgggg ccacatgaat        300
```

```
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta caccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg cctggatca ggttattccg    780 gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt    960 atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200 ggcggcattg ccattcagga tattcgcatg cgtgatgtta tcagctattt cgcaaccctat    1260 gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataattttt    1440 ctgagcggcc tggaattcaa ggtgggcgat aaaaccattg aagttcatcc gctgaccgat    1500
ccggatttta atatggttga ttcgtgttc caggagaagg gcaataataa tctggtggaa    1560
atgaacgagc tgaaccatga atttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 2
<211> LENGTH: 621
<212> TYPE: PRT
<213> ORGANISM: Streptococcus thermophilus

<400> SEQUENCE: 2

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp

```
            85                  90                  95
Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
            115                 120                 125

Ala Thr Ser Gln Met Glu Glu Val Gly Leu Glu Phe Ala Thr Leu
            130                 135             140

Met Gly Tyr Thr Asn Gly Trp Gly His Ile Val Ala Asp Gly Ser Leu
145                     150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
                180                 185                 190

Trp Glu Leu Ser Asn Met Ser Thr Lys Glu Ile Met Asp Leu Val Glu
                195                 200                 205

Ala Asn Gly Asp Lys Ile Asp Glu Ile Lys Ala Lys Ser Ala Arg Gly
            210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                    245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
                275                 280                 285

Leu Gly Val Val Gly Val Val Gly Ser Thr Glu Glu Gly Ala Val Asp
            290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                    325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
                355                 360                 365

Val Ser Glu His Thr Tyr Asn Ala Tyr Ala Ala Phe Pro Glu Ala Glu
            370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Lys Thr Leu Pro Leu Asn Val Thr Gly Tyr Gly
            450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510
```

Lys Gly Asn Asn Leu Val Glu Met Asn Glu Leu Asn His Glu Phe
      515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
                595                 600                 605

Met Gln Glu Lys Leu Glu Ala Ile Tyr Glu Asp Arg Lys
    610                 615                 620

<210> SEQ ID NO 3
<211> LENGTH: 1863
<212> TYPE: DNA
<213> ORGANISM: Artificial sequence
<220> FEATURE:
<223> OTHER INFORMATION: Engineered sequence

<400> SEQUENCE: 3
atgagcaaca ccagtttcag cgcaaaagat accgatctga gtgcactgtt tatcggtgac      60
aaagcagaaa tggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta caccaatggt tggggccata ttgttgcaga tggtagcctg     480
gcaaatctgg aaggcctgtg gatgcacgc aatattaaga gcctgccgtt tgccatgaaa     540
gccgttgatc cgaccattgt tgccggcaaa accgattggg aactgagtaa tatgagcacc     600
aaagaaatca tggaccctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt tccggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960 atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200 ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440

-continued

```
ctgagcggcc tggaattcaa ggtgggcgat aaaaccattg aagttcatcc gctgaccgat   1500
ccggatttta atatggttga ttacgtgttc caggagaagg gcaataatga tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 4
<211> LENGTH: 621
<212> TYPE: PRT
<213> ORGANISM: Artificial sequence
<220> FEATURE:
<223> OTHER INFORMATION: Engineered sequence

<400> SEQUENCE: 4

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
                20                  25                  30

Gly Lys Leu Val Asp Glu His Leu Gly Trp Arg Gln Asn Tyr Met Pro
            35                  40                  45

Gln Asp Lys Pro Met Ile Ser Ala Glu Gln Thr Ser Pro Glu Phe
        50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
```

Leu Gly Val Val Gly Val Val Gly Ser Thr Glu Glu Gly Ala Val Asp
    275                 280                 285
Gly Ile Asn Glu Ile Ala Glu Leu Arg Asn Lys Leu Val Lys Glu Gly
290                 295                 300
Ile Tyr Phe Tyr Phe His Ile Asp Ala Ala Tyr Gly Tyr Gly Arg
305                 310                 315                 320
Ala Ile Leu Leu Asp Glu Asp Asn Lys Leu Ile Pro Tyr Lys Asp Leu
        325                 330                 335
Gln Ser Lys Phe Ala Glu Tyr Asn Val Phe Thr Glu Glu Asn Leu
    340                 345                 350
Val Ser Glu His Thr Tyr Asn Ala Tyr Ala Ala Phe Pro Glu Ala Glu
355                 360                 365
Ser Val Thr Ile Asp Pro His Lys Met Gly Tyr Ile Pro Tyr Ser Ala
370                 375                 380
Gly Gly Ile Ala Ile Gln Asp Ile Arg Met Arg Asp Val Ile Ser Tyr
385                 390                 395                 400
Phe Ala Thr Tyr Val Phe Glu Lys Gly Ala Asp Ile Pro Ala Leu Leu
        405                 410                 415
Gly Ala Tyr Ile Leu Glu Gly Ser Lys Ala Gly Ala Thr Ala Ala Ser
    420                 425                 430
Val Trp Ala Ala His Lys Thr Leu Pro Leu Asn Val Thr Gly Tyr Gly
435                 440                 445
Lys Leu Val Gly Ala Ser Ile Glu Gly Ala Arg Arg Phe Tyr Asn Phe
450                 455                 460
Leu Ser Gly Leu Glu Phe Lys Val Gly Asp Lys Thr Ile Glu Val His
465                 470                 475                 480
Pro Leu Thr Asp Pro Asp Phe Asn Met Val Asp Tyr Val Phe Gln Glu
        485                 490                 495
Lys Gly Asn Asn Asp Leu Val Glu Met Asn Glu Leu Asn His Glu Phe
    500                 505                 510
Tyr Asn Gln Ala Ser Tyr Val Thr Gly Ser Ile Tyr Gly Asn Glu Tyr
515                 520                 525
Leu Thr Ser His Thr Asp Phe Ala Ile Pro Asp Tyr Gly Asn Ser Pro
530                 535                 540
Phe Lys Phe Val Asn Asn Leu Gly Val Thr Glu Glu Gly Trp Lys Glu
545                 550                 555                 560
Ala Gly Lys Val Thr Val Leu Arg Ala Ala Val Met Thr Pro Tyr Met
        565                 570                 575
Asn Lys Ala Glu Asn Phe Asp Tyr Phe Ala Pro Lys Ile Lys Gln Ala
    580                 585                 590
Met Gln Glu Lys Leu Glu Ala Ile Tyr Glu Asp Arg Lys
595                 600                 605

<210> SEQ ID NO 5
<211> LENGTH: 1863
<212> TYPE: DNA
<213> ORGANISM: Artificial sequence
<220> FEATURE:
<223> OTHER INFORMATION: Engineered sequence

<400> SEQUENCE: 5
atgagcaaca ccagtttcag cgcaaaagat accgatctga gtgcactgtt tatcggtgac      60
aaagcagaaa atggtcagct gtataaggac ctgctgggca aactggttga tgaacatctg     120

-continued

| | |
|---|---|
| ggttggcgcc agaattatat gccgcaggat aaaccgatga tcagcgccga acagcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg gaatggtaac | 360 |
| aacgtggcct atgaaagcag cccggcaacc agccagatgg aagaagaagt tggtctggaa | 420 |
| tttgccaccc tgatgggcta taccaatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc cgaccattgt tgccggcaaa accgattggg aactgagtaa tatgagcacc | 600 |
| aaagaaatca tggacctggt tgaagccctg ggtgacaaaa ttgatgagat caaggccaaa | 660 |
| agcgcccgcg gcgtaaaga tctggataaa ctgggtaaat ggctggttcc gcagaccaaa | 720 |
| cattatagtt ggctgaaagc cgcagatatt atcggcattg gcctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta acaagctggt gaaagaaggt | 960 |
| atctatttct acttccacat cgacgccgcc tatggtggc atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacatacct ataacgccta tgccgcattt | 1140 |
| ccggaagccg aaagtgttac cattgatccg cataaaatgg ctatatcccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaaccctgcc gctgaatgtt | 1380 |
| accggttatg gtaaactggt tggtgcaagc attgaaggcg cccgccgttt ttataatttt | 1440 |
| ctgagcggcc tggaattcaa ggtgggcgat aaaaccattg aagttcatcc gctgaccgat | 1500 |
| ccggatttta atatggttga ttacgtgttc caggagaagg gcaataataa tctggtggaa | 1560 |
| atgaacgagc tgaaccatga attttacaac caggcaagct acgttaccgg tagcatctat | 1620 |
| ggcaatgaat atctgaccag ccataccgat ttcgcaattc cggattatgg taatagcccg | 1680 |
| tttaagtttg tgaacaacct gggcgtgacc gaagaaggct ggaaagaagc aggtaaagtg | 1740 |
| accgttctgc gcgccgctgt gatgacacct tatatgaata aggcagagaa cttcgactac | 1800 |
| ttcgccccga aaattaagca ggccatgcag gaaaaactgg aagccatcta tgaagatcgt | 1860 |
| aag | 1863 |

<210> SEQ ID NO 6
<211> LENGTH: 621
<212> TYPE: PRT
<213> ORGANISM: Artificial sequence
<220> FEATURE:
<223> OTHER INFORMATION: Engineered sequence

<400> SEQUENCE: 6

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

```
Gln Asp Lys Pro Met Ile Ser Ala Glu Gln Gln Thr Ser Pro Glu Phe
 50                  55                  60
Arg Gly Thr Val Asn Asn Met Lys Asp Val Leu Asp Glu Leu Ser Ser
 65                  70                  75                  80
Arg Leu Arg Ser Gln Ser Val Pro Trp His Asn Ala Gly Arg Tyr Trp
                 85                  90                  95
Gly His Met Asn Ser Glu Thr Leu Met Pro Ala Ile Leu Ala Tyr Asn
                100                 105                 110
Tyr Ala Met Leu Trp Asn Gly Asn Val Ala Tyr Glu Ser Ser Pro
                115                 120                 125
Ala Thr Ser Gln Met Glu Glu Val Gly Leu Glu Phe Ala Thr Leu
 130                 135                 140
Met Gly Tyr Thr Asn Gly Trp Gly His Ile Val Ala Asp Gly Ser Leu
 145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
                180                 185                 190
Trp Glu Leu Ser Asn Met Ser Thr Lys Glu Ile Met Asp Leu Val Glu
                195                 200                 205
Ala Leu Gly Asp Lys Ile Asp Glu Ile Lys Ala Lys Ser Ala Arg Gly
 210                 215                 220
Gly Lys Asp Leu Asp Lys Leu Gly Lys Trp Leu Val Pro Gln Thr Lys
 225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
                260                 265                 270
Glu Leu Glu Lys Ile Ile Arg Glu Leu Ala Ser Thr Glu Thr Pro Ile
                275                 280                 285
Leu Gly Val Val Gly Val Gly Ser Thr Glu Glu Gly Ala Val Asp
 290                 295                 300
Gly Ile Asn Glu Ile Ala Glu Leu Arg Asn Lys Leu Val Lys Glu Gly
 305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
                340                 345                 350
Gln Ser Lys Phe Ala Glu Tyr Asn Val Phe Thr Glu Glu Asn Leu
                355                 360                 365
Val Ser Glu His Thr Tyr Asn Ala Tyr Ala Ala Phe Pro Glu Ala Glu
 370                 375                 380
Ser Val Thr Ile Asp Pro His Lys Met Gly Tyr Ile Pro Tyr Ser Ala
 385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
                420                 425                 430
Gly Ala Tyr Ile Leu Glu Gly Ser Lys Ala Gly Ala Thr Ala Ala Ser
                435                 440                 445
Val Trp Ala Ala His Lys Thr Leu Pro Leu Asn Val Thr Gly Tyr Gly
 450                 455                 460
Lys Leu Val Gly Ala Ser Ile Glu Gly Ala Arg Arg Phe Tyr Asn Phe
```

```
                465                 470                 475                 480
Leu Ser Gly Leu Glu Phe Lys Val Gly Asp Lys Thr Ile Glu Val His
                    485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                    565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
                    595                 600                 605

Met Gln Glu Lys Leu Glu Ala Ile Tyr Glu Asp Arg Lys
610                 615                 620

<210> SEQ ID NO 7
<211> LENGTH: 1863
<212> TYPE: DNA
<213> ORGANISM: Artificial sequence
<220> FEATURE:
<223> OTHER INFORMATION: Engineered sequence

<400> SEQUENCE: 7
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt gccatgaaa     540 gaagttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcgtaaaga tctggataaa ctgggtaaat ggctggttcc gcagaccaaa     720
cattatagtt ggctgaaagc cgcagatatt atcggcattg cctggatca ggttattccg     780 gttccggttg atagcaatta tcgtatggat atcaacgagc tggagaaaat atccgcgaa     840 ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960 atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
```

-continued

```
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaccctgcc gctgaatgtt     1380 accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500 ccggattttta atatggttga ttacgtgttc caggagaagg gcaataataa tctggtggaa   1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

```
<210> SEQ ID NO 8
<211> LENGTH: 621
<212> TYPE: PRT
<213> ORGANISM: Artificial sequence
<220> FEATURE:
<223> OTHER INFORMATION: Engineered sequence

<400> SEQUENCE: 8
```

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Glu Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

```
His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 9
<211> LENGTH: 1863
<212> TYPE: DNA
<213> ORGANISM: Artificial sequence
<220> FEATURE:
<223> OTHER INFORMATION: Engineered sequence
```

<400> SEQUENCE: 9

```
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc agaattatat gccgcaggat aaaccgatga tcagcgccga acagcagacc    180
agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg aatggtaac    360
aacgtggcct atgaaagcag cccggcaacc agccagatgg aagaagaagt tggtctggaa    420
tttgccaccc tgatgggcta caatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atccggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctgga aaagaaggt    960
atctatttct acttccacat cgacgccgcc tatggtggct atggtcgcgc aattctgctg   1020
gatgaagata ataagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatccc gtatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgttttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta tatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                  1863
```

<210> SEQ ID NO 10
<211> LENGTH: 621
<212> TYPE: PRT
<213> ORGANISM: Artificial sequence
<220> FEATURE:
<223> OTHER INFORMATION: Engineered sequence

<400> SEQUENCE: 10

```
Met Ser Asn Thr Ser Phe Ser Ala Lys Asp Thr Asp Leu Ser Ala Leu
1               5                   10                  15
```

-continued

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
 50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
            115                 120                 125

Ala Thr Ser Gln Met Glu Glu Glu Val Gly Leu Glu Phe Ala Thr Leu
 130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
            210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
        290                 295                 300

Gly Ile Asn Glu Ile Ala Glu Leu Arg Asn Lys Leu Glu Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
        370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 11
<211> LENGTH: 1863
<212> TYPE: DNA
<213> ORGANISM: Artificial sequence
<220> FEATURE:
<223> OTHER INFORMATION: Engineered sequence

<400> SEQUENCE: 11
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg cctggatca ggttattccg     780 gttccggttg atagcaatta tcgtatggat atcaacgagc tggagaaaat atccgcgaa     840 ctggcaagta ccgaaacccc gattctgggc gttgtgggcg ttgtgggtag taccgaagaa     900
ggtgccgtta tggcattaa tgaaattgca gaactgcgta acaagctggt gaaagaaggt     960
atctatttct acttccacat cgacgccgcc tatggtggct atggtcgcgc aattctgctg    1020

-continued

```
gatgaagata taaagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatcccg tatagtgca     1200 ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaaaaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                 1863
```

<210> SEQ ID NO 12
<211> LENGTH: 621
<212> TYPE: PRT
<213> ORGANISM: Artificial sequence
<220> FEATURE:
<223> OTHER INFORMATION: Engineered sequence

<400> SEQUENCE: 12

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205
```

```
Ala Asn Gly Asp Lys Ile Asp Glu Ile Lys Ala Lys Ser Ala Arg Gly
            210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                    245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
            290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                    325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                    405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Lys Thr Leu Pro Leu Asn Val Thr Gly Tyr Gly
            450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                    485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Lys
                    565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
610                 615                 620
```

<210> SEQ ID NO 13
<211> LENGTH: 1863
<212> TYPE: DNA
<213> ORGANISM: Artificial sequence
<220> FEATURE:
<223> OTHER INFORMATION: Engineered sequence

<400> SEQUENCE: 13

| | | | | | |
|---|---|---|---|---|---|
| atgagcaaca | ccagtttcag | cgcaaaagat | accgatctga | gtgcactgtt | tatcggtgac | 60 |
| aaagcagaaa | atggtcagct | gtataaggac | ctgctgggca | aactggttga | tgaacatctg | 120 |
| ggttggcgcc | agaattatat | gccgcaggat | aaaccgatga | tcagcgccga | acagcagacc | 180 |
| agcccggaat | tcgtggtac | cgtgaataat | atgaaggacg | ttctggatga | gctgagcagt | 240 |
| cgcctgcgta | gtcagagcgt | tccgtggcat | aatgccggtc | gttattgggg | ccacatgaat | 300 |
| agcgaaaccc | tgatgccggc | aattctggcc | tataattatg | caatgctgtg | gaatggtaac | 360 |
| aacgtggcct | atgaaagcag | cccggcaacc | agcagatgg | aagaagaagt | tggtctggaa | 420 |
| tttgccaccc | tgatgggcta | taccaatggt | tggggccata | ttgttgcaga | tggtagcctg | 480 |
| gcaaatctgg | aaggcctgtg | gtatgcacgc | aatattaaga | gcctgccgtt | gccatgaaa | 540 |
| gccgttgatc | cgaccattgt | tgccggcaaa | accgattggg | aactgagtaa | tatgagcacc | 600 |
| aaagaaatca | tggacctggt | tgaagccaat | ggtgacaaaa | ttgatgagat | caaggccaaa | 660 |
| agcgcccgcg | gcggtaaaga | tctggataaa | ctgggtaaat | ggctggttcc | gcagaccaaa | 720 |
| cattatagtt | ggctgaaagc | cgcagatatt | atcggcattg | gcctggatca | ggttattccg | 780 |
| gttccggttg | atagcaatta | tcgtatggat | atcaacgagc | tggagaaaat | tatccgcgaa | 840 |
| ctggcaagta | ccgaaacccc | gattctgggc | gttgtgggcg | ttgtgggtag | taccgaagaa | 900 |
| ggtgccgttg | atggcattaa | tgaaattgca | gaactgcgta | caagctggt | gaaagaaggt | 960 |
| atctatttct | acttccacat | cgacgccgcc | tatggtggct | atggtcgcgc | aattctgctg | 1020 |
| gatgaagata | taagctgat | cccgtataag | gaccttcaga | gtaaattcgc | cgaatataac | 1080 |
| gtgttcaccg | aagaagaaaa | cctggtgagt | gaacatacct | ataacgccta | tgccgcatt | 1140 |
| ccggaagccg | aaagtgttac | cattgatccg | cataaaatgg | gctatatccc | gtatagtgca | 1200 |
| ggcggcattg | ccattcagga | tattcgcatg | cgtgatgtta | tcagctattt | cgcaacctat | 1260 |
| gtgttcgaaa | agggcgcaga | tattccggca | ctgctgggtg | cttatattct | ggaaggcagt | 1320 |
| aaagcaggcg | caaccgcagc | cagtgttttgg | gcagcacata | aaaccctgcc | gctgaatgtt | 1380 |
| accggttatg | gtaaactgct | gggtgcaagc | attgaaggcg | cccgccgttt | ttataatttt | 1440 |
| ctgagcggcc | tggaattcaa | ggtgggcgat | aaaaccattg | aagttcatcc | gctgaccgat | 1500 |
| ccggattta | atatggttga | ttacgtgttc | caggagaagg | gcaataataa | tctggtggaa | 1560 |
| atgaacgagc | tgaaccatga | attttacaac | caggcaagct | acgttaccgg | tagcatctat | 1620 |
| ggcaatgaat | atctgaccag | ccataccgat | ttcgcaattc | cggattatgg | taatagcccg | 1680 |
| tttaagtttg | tgaacaacct | gggcgtgacc | gaagaaggct | ggaaagaagc | aggtaaagtg | 1740 |
| accgttctgc | gcgccgctgt | gatgacacct | tatatgaata | aggcagagaa | cttcgactac | 1800 |
| ttcgccccga | aaattaagca | ggccatgcag | gaaaaactgg | aagccatcta | tgaagatcgt | 1860 |
| aag | | | | | | 1863 |

<210> SEQ ID NO 14
<211> LENGTH: 621
<212> TYPE: PRT
<213> ORGANISM: Artificial sequence
<220> FEATURE:
<223> OTHER INFORMATION: Engineered sequence

<400> SEQUENCE: 14

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
        420                 425                 430

Gly Ala Tyr Ile Leu Glu Gly Ser Lys Ala Gly Ala Thr Ala Ala Ser
    435                 440                 445

Val Trp Ala Ala His Lys Thr Leu Pro Leu Asn Val Thr Gly Tyr Gly
450                 455                 460

Lys Leu Leu Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 15
<211> LENGTH: 1863
<212> TYPE: DNA
<213> ORGANISM: Artificial sequence
<220> FEATURE:
<223> OTHER INFORMATION: Engineered sequence

<400> SEQUENCE: 15
atgagcaaca ccagtttcag cgcaaaagat accgatctga gtgcactgtt tatcggtgac    60
aaagcagaaa atggtcagct gtataaggac ctgctgggca aactggttga tgaacatctg   120
ggttggcgcc agaattatat gccgcaggat aaaccgatga tcagcgccga acagcagacc   180
agcccggaat tcgtggtac cgtgaataat atgaaggacg ttctggatga gctgagcagt   240
cgcctgcgta gtcagagcgt tccgtggcat aatgccggtc gttattgggg ccacatgaat   300
agcgaaaccc tgatgccggc aattctggcc tataattatg caatgctgtg aatggtaac   360 aacgtggcct atgaaagcag cccggcaacc agccagatgg aagaagaagt tggtctggaa   420
tttgccaccc tgatgggcta taccaatggt tggggccata ttgttgcaga tggtagcctg   480
gcaaatctgg aaggcctgtg gtatgcacgc aatattaaga gcctgccgtt tgccatgaaa   540
gccgttgatc cgaccattgt tgccggcaaa accgattggg aactgagtaa tatgagcacc   600
aaagaaatca tggacctggt tgaagccaat ggtgacaaaa ttgatgagat caaggccaaa   660
agcgcccgcg gcgtaaaga tctggataaa ctgggtaaat ggctggttcc gcagaccaaa   720
cattatagtt ggctgaaagc cgcagatatt atcggcattg gctggatca ggttattccg   780

```
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt    960 atctatttct acttccacat cgacgccgcc tatggtggct atggtcgcgc aattctgctg   1020
gatgaagata taagctgat cccgtataag gaccttcaga gtaaattcgc cgaatataac    1080
gtgttcaccg aagaagaaaa cctggtgagt gaacatacct ataacgccta tgccgcactg   1140
ccggaagccg aaagtgttac cattgatccg cataaaatgg ctatatccc gtatagtgca    1200 ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaccctgcc gctgaatgtt    1380 accggttatg gtaaactggt tggtgcaagc attgaaggcg cccgccgttt ttataatttt    1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 16
<211> LENGTH: 621
<212> TYPE: PRT
<213> ORGANISM: Artificial sequence
<220> FEATURE:
<223> OTHER INFORMATION: Engineered sequence

<400> SEQUENCE: 16

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
```

-continued

```
                165                 170                 175
Phe Ala Met Lys Ala Val Asp Pro Thr Ile Val Ala Gly Lys Thr Asp
                180                 185                 190

Trp Glu Leu Ser Asn Met Ser Thr Lys Glu Ile Met Asp Leu Val Glu
                195                 200                 205

Ala Asn Gly Asp Lys Ile Asp Glu Ile Lys Ala Lys Ser Ala Arg Gly
            210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
                260                 265                 270

Glu Leu Glu Lys Ile Ile Arg Glu Leu Ala Ser Thr Glu Thr Pro Ile
                275                 280                 285

Leu Gly Val Val Gly Val Gly Ser Thr Glu Glu Gly Ala Val Asp
                290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
                355                 360                 365

Val Ser Glu His Thr Tyr Asn Ala Tyr Ala Ala Leu Pro Glu Ala Glu
                370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
            450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590
```

```
Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
    610                 615                 620
```

<210> SEQ ID NO 17
<211> LENGTH: 1863
<212> TYPE: DNA
<213> ORGANISM: Artificial sequence
<220> FEATURE:
<223> OTHER INFORMATION: Engineered sequence

<400> SEQUENCE: 17

```
atgagcaaca ccagtttcag cgcaaaagat accgatctga gtgcactgtt tatcggtgac    60
aaagcagaaa atggtcagct gtataaggac ctgctgggca aactggttga tgaacatctg   120
ggttggcgcc agaattatat gccgcaggat aaaccgatga tcagcgccga cagcagacc    180
agcccggaat tcgtggtac cgtgaataat atgaaggacg ttctggatga gctgagcagt   240
cgcctgcgta gtcagagcgt tccgtggcat aatgccggtc gttattgggg ccacatgaat   300
agcgaaaccc tgatgccggc aattctggcc tataattatg caatgctgtg gaatggtaac   360
aacgtggcct atgaaagcag cccggcaacc agccagatgg aagaagaagt tggtctggaa   420
tttgccaccc tgatgggcta ccaatggt tggggccata ttgttgcaga tggtagcctg    480
gcaaatctgg aaggcctgtg gtatgcacgc aatattaaga gcctgccgtt tgccatgaaa   540
gccgttgatc cgaccattgt tgccggcaaa accgattggg aactgagtaa tatgagcacc   600
aaagaaatca tggacctggt tgaagccaat ggtgacaaaa ttgatgagat caaggccaaa   660
agcgcccgcg gcgtaaaga tctggataaa ctgggtaaat ggctggttcc gcagaccaaa   720
cattatagtt ggctgaaagc cgcagatat tcggcattg cctggatca ggttattccg    780
gttccggttg atagcaatta tcgtatggat atcaacgagc tggagaaaat tatccgcgaa   840
ctggcaagta ccgaaacccc gattctgggc gttgtgggcg ttgtgggtag taccgaagaa   900
ggtgccgttg atggcattaa tgaaattgca gaactgcgta acaagctggt gaaagaaggt   960
atctatttct acttccacat cgacgccgcc tatggtggct atggtcgcgc aattctgctg  1020
gatgaagata taagctgat cccgtataag gaccttcaga gtaaattcgc cgaatataac  1080
gtgttcaccg aagaagaaa cctggtgagt gaacatacct ataacgccta tgccgcattt  1140
ccggaagccg aaagtgttac cattgatccg cataaaatgg ctatatccc gtatagtgca  1200
ggcggcattg ccattcagga tattcgcatg cgtgatgtta tcagctattt cgcaacctat  1260
gtgttcgaaa agggcgcaga tattccggca ctgctgggtg cttatattct ggaaggcagt  1320
aaagcaggcg caaccgcagc cagtgtttgg gcagcacata aaaccctgcc gctgaatgtt  1380
accggttatg gtaaactggt tggtgcaagc attgaaggcg cccgccgttt ttataatttt  1440
ctgagcggcc tggaattcaa ggtgggcgat aaaaccattg aagttcatcc gctgaccgat  1500
ccggatttta atatggttga ttacgtgttc caggagaagg gcaataataa tctggtggaa  1560
atgaacgagc tgaaccatga atttacgat caggcaagct acgttaccgg tagcatctat  1620
ggcaatgaat atctgaccag ccataccgat ttcgcaattc cggattatgg taatagcccg  1680
tttaagtttg tgaacaacct gggcgtgacc gaagaaggct ggaaagaagc aggtaaagtg  1740
accgttctgc gcgccgctgt gatgacacct tatatgaata aggcagagaa cttcgactac  1800
ttcgccccga aaattaagca ggccatgcag gaaaaactgg aagccatcta tgaagatcgt  1860
``` aag                                                                 1863

<210> SEQ ID NO 18
<211> LENGTH: 621
<212> TYPE: PRT
<213> ORGANISM: Artificial sequence
<220> FEATURE:
<223> OTHER INFORMATION: Engineered sequence

<400> SEQUENCE: 18

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
                20                  25                  30

Gly Lys Leu Val Asp Glu His Leu Gly Trp Arg Gln Asn Tyr Met Pro
            35                  40                  45

Gln Asp Lys Pro Met Ile Ser Ala Glu Gln Thr Ser Pro Glu Phe
        50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
                100                 105                 110

Tyr Ala Met Leu Trp Asn Gly Asn Val Ala Tyr Glu Ser Ser Pro
            115                 120                 125

Ala Thr Ser Gln Met Glu Glu Val Gly Leu Glu Phe Ala Thr Leu
        130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
                180                 185                 190

Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
        210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
                260                 265                 270

Glu Leu Glu Lys Ile Ile Arg Glu Leu Ala Ser Thr Glu Thr Pro Ile
            275                 280                 285

Leu Gly Val Val Gly Val Gly Ser Thr Glu Glu Gly Ala Val Asp
        290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Glu Asn Leu

```
                  355                 360                 365
Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asp Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
610                 615                 620

<210> SEQ ID NO 19
<211> LENGTH: 1863
<212> TYPE: DNA
<213> ORGANISM: Artificial sequence
<220> FEATURE:
<223> OTHER INFORMATION: Engineered sequence

<400> SEQUENCE: 19
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc agaattatat gccgcaggat ccgccgatga tcagcgccga acagcagacc    180
agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
```

-continued

```
aaagaaatca tggacctggt tgaagccaat ggtgacaaaa ttgatgagat caaggccaaa      660
agcgcccgcg gcggtaaaga tctggataaa ctgggtaaat ggctggttcc gcagaccaaa      720
cattatagtt ggctgaaagc cgcagatatt atcggcattg gcctggatca ggttattccg      780
gttccggttg atagcaatta tcgtatggat atcaacgagc tggagaaaat tatccgcgaa      840
ctggcaagta ccgaaacccc gattctgggc gttgtgggcg ttgtgggtag taccgaagaa      900
ggtgccgttg atggcattaa tgaaattgca gaactgcgta acaagctggt gaaagaaggt      960
atctatttct acttccacat cgacgccgcc tatggtggct atggtcgcgc aattctgctg     1020
gatgaagata taagctgat cccgtataag gaccttcaga gtaaattcgc cgaatataac      1080
gtgttcaccg aagaagaaaa cctggtgagt gaacatacct ataacgccta tgccgcattt     1140
ccggaagccg aaagtgttac cattgatccg cataaaatgg ctatatcccg gtatagtgca     1200
ggcggcattg ccattcagga tattcgcatg cgtgatgtta tcagctattt cgcaacctat     1260
gtgttcgaaa agggcgcaga tattccggca ctgctgggtg cttatattct ggaaggcagt     1320
aaagcaggcg caaccgcagc cagtgtttgg gcagcacata aaaccctgcc gctgaatgtt     1380
accggttatg gtaaactggt tggtgcaagc attgaaggcg cccgccgttt ttataatttt     1440
ctgagcggcc tggaattcaa ggtgggcgat aaaaccattg aagttcatcc gctgaccgat     1500
ccggatttta atatggttga ttacgtgttc caggagaagg gcaataataa tctggtggaa     1560
atgaacgagc tgaaccatga attttacaac caggcaagct acgttaccgg tagcatctat     1620
ggcaatgaat atctgaccag ccataccgat ttcgcaattc cggattatgg taatagcccg     1680
tttaagtttg tgaacaacct gggcgtgacc gaagaaggct ggaaagaagc aggtaaagtg     1740
accgttctgc gcgccgctgt gatgacacct tatatgaata aggcagagaa cttcgactac     1800
ttcgccccga aaattaagca ggccatgcag gaaaaactgg aagccatcta tgaagatcgt     1860
aag                                                                   1863
```

<210> SEQ ID NO 20
<211> LENGTH: 621
<212> TYPE: PRT
<213> ORGANISM: Artificial sequence
<220> FEATURE:
<223> OTHER INFORMATION: Engineered sequence

<400> SEQUENCE: 20

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125
```

```
Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
```

```
                545                 550                 555                 560
             Phe Lys Phe Val Asn Asn Leu Gly Val Thr Glu Glu Gly Trp Lys Glu
                             565                 570                 575

Ala Gly Lys Val Thr Val Leu Arg Ala Ala Val Met Thr Pro Tyr Met
                             580                 585                 590

Asn Lys Ala Glu Asn Phe Asp Tyr Phe Ala Pro Lys Ile Lys Gln Ala
                             595                 600                 605

Met Gln Glu Lys Leu Glu Ala Ile Tyr Glu Asp Arg Lys
                             610                 615                 620

<210> SEQ ID NO 21
<211> LENGTH: 1863
<212> TYPE: DNA
<213> ORGANISM: Artificial sequence
<220> FEATURE:
<223> OTHER INFORMATION: Engineered sequence

<400> SEQUENCE: 21
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat actccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg aatggtaac     360 aacgtggcct atgaaagcag cccggcaacc agccagatgg aagaagaagt tggtctggaa     420
tttgccaccc tgatgggcta caccatggt tggggccata ttgttgcaga tggtagcctg      480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt cgggcattg gcctggatca ggttattccg       780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta acaagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac      1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg caataataa tctggtggaa      1560 atgaacgagc tgaaccatga attttacaac caggcaagct acgttaccgg tagcatctat    1620
ggcaatgaat atctgaccag ccataccgat ttcgcaattc cggattatgg taatagcccg    1680
```

```
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 22
<211> LENGTH: 621
<212> TYPE: PRT
<213> ORGANISM: Artificial sequence
<220> FEATURE:
<223> OTHER INFORMATION: Engineered sequence

<400> SEQUENCE: 22

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Thr Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320
```

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 23
<211> LENGTH: 1863
<212> TYPE: DNA
<213> ORGANISM: Artificial sequence
<220> FEATURE:
<223> OTHER INFORMATION: Engineered sequence

<400> SEQUENCE: 23
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaactatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360

```
aacgtggcct atgaaagcag cccggcaacc agccagatgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatcccc gtatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt tataattttt   1440
ctgagcggcc tggaattcaa ggtgggcgat aaaaccattg aagttcatcc gctgaccgat   1500 ccggattttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 24
<211> LENGTH: 621
<212> TYPE: PRT
<213> ORGANISM: Artificial sequence
<220> FEATURE:
<223> OTHER INFORMATION: Engineered sequence

<400> SEQUENCE: 24

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Thr Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95
```

```
Gly His Met Asn Ser Glu Thr Leu Met Pro Ala Ile Leu Ala Tyr Asn
            100                 105                 110

Tyr Ala Met Leu Trp Asn Gly Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
        420                 425                 430

Gly Ala Tyr Ile Leu Glu Gly Ser Lys Ala Gly Ala Thr Ala Ala Ser
    435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510
```

```
Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
            565                 570                 575

Ala Gly Lys Val Thr Val Leu Arg Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
        610                 615                 620

<210> SEQ ID NO 25
<211> LENGTH: 1863
<212> TYPE: DNA
<213> ORGANISM: Artificial sequence
<220> FEATURE:
<223> OTHER INFORMATION: Engineered sequence

<400> SEQUENCE: 25
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaagtgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg cctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
```

```
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                 1863

<210> SEQ ID NO 26
<211> LENGTH: 621
<212> TYPE: PRT
<213> ORGANISM: Artificial sequence
<220> FEATURE:
<223> OTHER INFORMATION: Engineered sequence

<400> SEQUENCE: 26
```

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Val Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Gly Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
                355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
                595                 600                 605

Met Gln Glu Lys Leu Glu Ala Ile Tyr Glu Asp Arg Lys
    610                 615                 620

<210> SEQ ID NO 27
<211> LENGTH: 1863
<212> TYPE: DNA
<213> ORGANISM: Artificial sequence
<220> FEATURE:
<223> OTHER INFORMATION: Engineered sequence

<400> SEQUENCE: 27
atgagcaaca ccagtttcag cgcaaaagat accgatctga gtgcactgtt tatcggtgac    60
aaagcagaaa atggtcagct gtataaggac ctgctgggca aactggttga tgaacatctg   120
ggttggcgcc agaattatat gccgcaggat aaaccgatga tcagcgccga acagcagacc   180

```
agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta ccaatggt tggggccata ttgttgcaga tggtagcctg      480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg cctggatca ggttattccg     780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt      960
atctatttct acttccacat cgacgccgcc tatggtggct atggtcgcgc aattctgctg   1020
gatgaagata taagctgat cccgtataag gaccttcaga gtaaattcgc cgaatataac    1080
gtgttcaccg aagaagaaaa cctggtgagt gaacatacct ataacgccta tgccgcattt   1140
ccggaagccg aaagtgttac cattgatccg cataaaatgg ctatatccc gtatagtgca    1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct actggaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 28
<211> LENGTH: 621
<212> TYPE: PRT
<213> ORGANISM: Artificial sequence
<220> FEATURE:
<223> OTHER INFORMATION: Engineered sequence

<400> SEQUENCE: 28

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Gln Thr Ser Pro Glu Phe
```

```
            50                  55                  60
Arg Gly Thr Val Asn Asn Met Lys Asp Val Leu Asp Glu Leu Ser Ser
 65                  70                  75                  80

Arg Leu Arg Ser Gln Ser Val Pro Trp His Asn Ala Gly Arg Tyr Trp
                 85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
            115                 120                 125

Ala Thr Ser Gln Met Glu Glu Val Gly Leu Glu Phe Ala Thr Leu
130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480
```

| | | | | | | | | | | | |
|---|---|---|---|---|---|---|---|---|---|---|---|
|Leu|Ser|Gly|Leu|Glu|Phe|Lys|Val|Gly|Asp|Lys|Thr|Ile|Glu|Val|His|
| | | | |485| | | | |490| | | | |495| |

Pro Leu Thr Asp Pro Asp Phe Asn Met Val Asp Tyr Val Phe Gln Glu
             500                 505                 510

Lys Gly Asn Asn Asn Leu Val Glu Met Asn Glu Leu Asn His Glu Phe
             515                 520                 525

Tyr Asn Gln Ala Ser Tyr Trp Thr Gly Ser Ile Tyr Gly Asn Glu Tyr
             530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
             565                 570                 575

Ala Gly Lys Val Thr Val Leu Arg Ala Ala Val Met Thr Pro Tyr Met
             580                 585                 590

Asn Lys Ala Glu Asn Phe Asp Tyr Phe Ala Pro Lys Ile Lys Gln Ala
             595                 600                 605

Met Gln Glu Lys Leu Glu Ala Ile Tyr Glu Asp Arg Lys
    610                 615                 620

<210> SEQ ID NO 29
<211> LENGTH: 1863
<212> TYPE: DNA
<213> ORGANISM: Artificial sequence
<220> FEATURE:
<223> OTHER INFORMATION: Engineered sequence

<400> SEQUENCE: 29

```
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc agaattatat gccgcaggat aaaccgatga tcagcgccga cagcagacc    180
agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccaggtgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcgtaaaga tctggataaa ctgggtaaat ggctggttcc gcagaccaaa    720
cattatagtt ggctgaaagc cgcagatatt atcggcattg cctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgcg gaactgcgta caagctggt gaagaaggt    960
atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaa cctggtgagt gaacataccct ataacgccta tgccgcattt   1140
ccggaagcca aaagtgttac cattgatccg cataaaatgg ctatatccc gtatagtgca   1200
ggcggcattg ccattcagga tattcgcatg cgtgatgtta tcagctattt cgcaacctat   1260
```

```
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtagactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                 1863
```

<210> SEQ ID NO 30
<211> LENGTH: 621
<212> TYPE: PRT
<213> ORGANISM: Artificial sequence
<220> FEATURE:
<223> OTHER INFORMATION: Engineered sequence

<400> SEQUENCE: 30

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Val Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
```

```
                  245                 250                 255
    Gln Val Ile Pro Val Pro Val Asp Ser Asn Tyr Arg Met Asp Ile Asn
                      260                 265                 270
    Glu Leu Glu Lys Ile Ile Arg Glu Leu Ala Ser Thr Glu Thr Pro Ile
                  275                 280                 285
    Leu Gly Val Val Gly Val Val Gly Ser Thr Glu Glu Gly Ala Val Asp
                  290                 295                 300
    Gly Ile Asn Glu Ile Ala Glu Leu Arg Asn Lys Leu Val Lys Glu Gly
    305                 310                 315                 320
    Ile Tyr Phe Tyr Phe His Ile Asp Ala Ala Tyr Gly Gly Tyr Gly Arg
                      325                 330                 335
    Ala Ile Leu Leu Asp Glu Asp Asn Lys Leu Ile Pro Tyr Lys Asp Leu
                  340                 345                 350
    Gln Ser Lys Phe Ala Glu Tyr Asn Val Phe Thr Glu Glu Asn Leu
                  355                 360                 365
    Val Ser Glu His Thr Tyr Asn Ala Tyr Ala Ala Phe Pro Glu Ala Glu
    370                 375                 380
    Ser Val Thr Ile Asp Pro His Lys Met Gly Tyr Ile Pro Tyr Ser Ala
    385                 390                 395                 400
    Gly Gly Ile Ala Ile Gln Asp Ile Arg Met Arg Asp Val Ile Ser Tyr
                      405                 410                 415
    Phe Ala Thr Tyr Val Phe Glu Lys Gly Ala Asp Ile Pro Ala Leu Leu
                  420                 425                 430
    Gly Ala Tyr Ile Leu Glu Gly Ser Lys Ala Gly Ala Thr Ala Ala Ser
                  435                 440                 445
    Val Trp Ala Ala His Lys Thr Leu Pro Leu Asn Val Thr Gly Tyr Gly
                  450                 455                 460
    Arg Leu Val Gly Ala Ser Ile Glu Gly Ala Arg Arg Phe Tyr Asn Phe
    465                 470                 475                 480
    Leu Ser Gly Leu Glu Phe Lys Val Gly Asp Lys Thr Ile Glu Val His
                      485                 490                 495
    Pro Leu Thr Asp Pro Asp Phe Asn Met Val Asp Tyr Val Phe Gln Glu
                  500                 505                 510
    Lys Gly Asn Asn Asn Leu Val Glu Met Asn Glu Leu Asn His Glu Phe
                  515                 520                 525
    Tyr Asn Gln Ala Ser Tyr Val Thr Gly Ser Ile Tyr Gly Asn Glu Tyr
                  530                 535                 540
    Leu Thr Ser His Thr Asp Phe Ala Ile Pro Asp Tyr Gly Asn Ser Pro
    545                 550                 555                 560
    Phe Lys Phe Val Asn Asn Leu Gly Val Thr Glu Gly Trp Lys Glu
                      565                 570                 575
    Ala Gly Lys Val Thr Val Leu Arg Ala Ala Val Met Thr Pro Tyr Met
                  580                 585                 590
    Asn Lys Ala Glu Asn Phe Asp Tyr Phe Ala Pro Lys Ile Lys Gln Ala
                  595                 600                 605
    Met Gln Glu Lys Leu Glu Ala Ile Tyr Glu Asp Arg Lys
                  610                 615                 620

<210> SEQ ID NO 31
<211> LENGTH: 1863
<212> TYPE: DNA
<213> ORGANISM: Artificial sequence
<220> FEATURE:
<223> OTHER INFORMATION: Engineered sequence
```

<400> SEQUENCE: 31

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagcc aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggattta atatggttga ttacgtgttc caggagaagg gcaataataa tctggtggaa    1560
atgaacgagc tgaaccatga attttacaac caggcaagct acgttggtgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                   1863
```

<210> SEQ ID NO 32
<211> LENGTH: 621
<212> TYPE: PRT
<213> ORGANISM: Artificial sequence
<220> FEATURE:
<223> OTHER INFORMATION: Engineered sequence

<400> SEQUENCE: 32

```
Met Ser Asn Thr Ser Phe Ser Ala Lys Asp Thr Asp Leu Ser Ala Leu
1               5                   10                  15
```

```
Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
            115                 120                 125

Ala Thr Ser Gln Met Glu Glu Val Gly Leu Glu Phe Ala Thr Leu
130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Phe Pro Glu Ala Glu
        370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
```

| | 435 | | | 440 | | | 445 | | | | |
|---|---|---|---|---|---|---|---|---|---|---|---|
Val Trp Ala Ala His Lys Thr Leu Pro Leu Asn Val Thr Gly Tyr Gly
450                     455                     460

Lys Leu Val Gly Ala Ser Ile Glu Gly Ala Arg Arg Phe Tyr Asn Phe
465                     470                     475                     480

Leu Ser Gly Leu Glu Phe Lys Val Gly Asp Lys Thr Ile Glu Val His
                485                     490                     495

Pro Leu Thr Asp Pro Asp Phe Asn Met Val Asp Tyr Val Phe Gln Glu
            500                     505                     510

Lys Gly Asn Asn Asn Leu Val Glu Met Asn Glu Leu Asn His Glu Phe
        515                     520                     525

Tyr Asn Gln Ala Ser Tyr Val Gly Gly Ser Ile Tyr Gly Asn Glu Tyr
    530                     535                     540

Leu Thr Ser His Thr Asp Phe Ala Ile Pro Asp Tyr Gly Asn Ser Pro
545                     550                     555                     560

Phe Lys Phe Val Asn Asn Leu Gly Val Thr Glu Glu Gly Trp Lys Glu
                565                     570                     575

Ala Gly Lys Val Thr Val Leu Arg Ala Ala Val Met Thr Pro Tyr Met
            580                     585                     590

Asn Lys Ala Glu Asn Phe Asp Tyr Phe Ala Pro Lys Ile Lys Gln Ala
        595                     600                     605

Met Gln Glu Lys Leu Glu Ala Ile Tyr Glu Asp Arg Lys
    610                     615                     620

<210> SEQ ID NO 33
<211> LENGTH: 1863
<212> TYPE: DNA
<213> ORGANISM: Artificial sequence
<220> FEATURE:
<223> OTHER INFORMATION: Engineered sequence

<400> SEQUENCE: 33
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc agaattatat gccgcaggat aaaccgatga tcagcgccga acagcagacc    180
agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg aatggtaac    360 aacgtggcct atgaaagcag cccggcaacc agccagatgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660 agcgccccgcg gcggtaaaga tctggataaa ctgggtaaat ggctggttcc gcagaccaaa    720
cattatagtt ggctgaaagc cgcagatatt atccggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020

```
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tgtgatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 34
<211> LENGTH: 621
<212> TYPE: PRT
<213> ORGANISM: Artificial sequence
<220> FEATURE:
<223> OTHER INFORMATION: Engineered sequence

<400> SEQUENCE: 34

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205
```

```
Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
                260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Leu Val Glu Met Asn Glu Leu Asn His Glu Phe
    515                 520                 525

Tyr Asn Gln Ala Ser Tyr Val Thr Gly Val Ile Tyr Gly Asn Glu Tyr
530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
610                 615                 620
```

<210> SEQ ID NO 35
<211> LENGTH: 1863
<212> TYPE: DNA
<213> ORGANISM: Artificial sequence
<220> FEATURE:
<223> OTHER INFORMATION: Engineered sequence

<400> SEQUENCE: 35

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tgggccata ttgttgcaga tggtagcctg      480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg cggtaaaga tctggataaa ctgggtaaat ggctggttcc gcagaccaaa      720
cattatagtt ggctgaaagc cgcagatatt atcggcattg cctggatca ggttattccg      780 gttccggttg atagcaatta tcgtatggat ccgaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta acaagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac     1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt tgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500 ccggattta atatggttga ttacgtgttc caggagaagg gcaataataa tctggtggaa     1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                   1863
```

<210> SEQ ID NO 36
<211> LENGTH: 621
<212> TYPE: PRT
<213> ORGANISM: Artificial sequence
<220> FEATURE:

<223> OTHER INFORMATION: Engineered sequence

<400> SEQUENCE: 36

Met Ser Asn Thr Ser Phe Ser Ala Lys Asp Thr Asp Leu Ser Ala Leu
1               5                   10                  15
Phe Ile Gly Asp Lys Ala Glu Asn Gly Gln Leu Tyr Lys Asp Leu Leu
            20                  25                  30
Gly Lys Leu Val Asp Glu His Leu Gly Trp Arg Gln Asn Tyr Met Pro
        35                  40                  45
Gln Asp Lys Pro Met Ile Ser Ala Glu Gln Gln Thr Ser Pro Glu Phe
    50                  55                  60
Arg Gly Thr Val Asn Asn Met Lys Asp Val Leu Asp Glu Leu Ser Ser
65                  70                  75                  80
Arg Leu Arg Ser Gln Ser Val Pro Trp His Asn Ala Gly Arg Tyr Trp
                85                  90                  95
Gly His Met Asn Ser Glu Thr Leu Met Pro Ala Ile Leu Ala Tyr Asn
            100                 105                 110
Tyr Ala Met Leu Trp Asn Gly Asn Val Ala Tyr Glu Ser Ser Pro
        115                 120                 125
Ala Thr Ser Gln Met Glu Glu Val Gly Leu Glu Phe Ala Thr Leu
    130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
            180                 185                 190
Trp Glu Leu Ser Asn Met Ser Thr Lys Glu Ile Met Asp Leu Val Glu
        195                 200                 205
Ala Asn Gly Asp Lys Ile Asp Glu Ile Lys Ala Lys Ser Ala Arg Gly
    210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Pro Asn
            260                 265                 270
Glu Leu Glu Lys Ile Ile Arg Glu Leu Ala Ser Thr Glu Thr Pro Ile
        275                 280                 285
Leu Gly Val Val Gly Val Val Gly Ser Thr Glu Glu Gly Ala Val Asp
    290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
        355                 360                 365
Val Ser Glu His Thr Tyr Asn Ala Tyr Ala Ala Phe Pro Glu Ala Glu
    370                 375                 380
Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
        435                 440                 445
Val Trp Ala Ala His Lys Thr Leu Pro Leu Asn Val Thr Gly Tyr Gly
    450                 455                 460
Lys Leu Val Gly Ala Ser Ile Glu Gly Ala Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Asn Leu Val Glu Met Asn Glu Leu Asn His Glu Phe
        515                 520                 525
Tyr Asn Gln Ala Ser Tyr Val Thr Gly Ser Ile Tyr Gly Asn Glu Tyr
    530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
        595                 600                 605
Met Gln Glu Lys Leu Glu Ala Ile Tyr Glu Asp Arg Lys
    610                 615                 620

<210> SEQ ID NO 37
<211> LENGTH: 1863
<212> TYPE: DNA
<213> ORGANISM: Artificial sequence
<220> FEATURE:
<223> OTHER INFORMATION: Engineered sequence

<400> SEQUENCE: 37
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc agaattatat gccgcaggat aaaccgatga tcagcgccga cagcagacc    180 agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg aatggtaac    360 aacgtgtcct atgaaagcag cccggcaacc agccagatgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gctgcatca ggttattccg    780 gttccggttg atagcaatta tcgtatggat agtaacgagc tggagaaat tatccgcgaa    840

```
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata ataagctgat cccgtataag gaccttcaga gtaaattcgc cgaatataac   1080
gtgttcaccg aagaagaaaa cctggtgagt gaacatacct ataacgccta tgccgcattt   1140
ccggaagcca aagtgttac cattgatccg cataaaatgg ctatatcccg tatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863

<210> SEQ ID NO 38
<211> LENGTH: 621
<212> TYPE: PRT
<213> ORGANISM: Artificial sequence
<220> FEATURE:
<223> OTHER INFORMATION: Engineered sequence

<400> SEQUENCE: 38

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ser Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175
```

-continued

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ser Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

```
Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
    610                 615                 620
```

<210> SEQ ID NO 39
<211> LENGTH: 1863
<212> TYPE: DNA
<213> ORGANISM: Artificial sequence
<220> FEATURE:
<223> OTHER INFORMATION: Engineered sequence

<400> SEQUENCE: 39

| | | | | | |
|---|---|---|---|---|---|
| atgagcaaca | ccagtttcag | cgcaaaagat | accgatctga | gtgcactgtt | tatcggtgac | 60 |
| aaagcagaaa | atggtcagct | gtataaggac | ctgctgggca | aactggttga | tgaacatctg | 120 |
| ggttggcgcc | agaattatat | gccgcaggat | aaaccgatga | tcagcgccga | acagcagacc | 180 |
| agcccggaat | tcgtggtac | cgtgaataat | atgaaggacg | ttctggatga | gctgagcagt | 240 |
| cgcctgcgta | gtcagagcgt | tccgtggcat | aatgccggtc | gttattgggg | ccacatgaat | 300 |
| agcgaaaccc | tgatgccggc | aattctggcc | tataattatg | caatgctgtg | aatggtaac | 360 |
| aacgtggcct | atgaaagcag | cccggcaacc | agccagatga | agaagaagt | tggtctggaa | 420 |
| tttgccaccc | tgatgggcta | taccaatggt | tggggccata | tgttgcaga | tggtagcctg | 480 |
| gcaaatctgg | aaggcctgtg | gtatgcacgc | aatattaaga | gcctgccgtt | tgccatgaaa | 540 |
| gccgttgatc | cgaccattgt | tgccggcaaa | accgattggg | aactgagtaa | tatgagcacc | 600 |
| aaagaaatca | tggacctggt | tgaagccaat | ggtgacaaaa | ttgatgagat | caaggccaaa | 660 |
| agcgcccgcg | gcggtaaaga | tctggataaa | ctgggtaaat | ggctggttcc | gcagaccaaa | 720 |
| cattatagtt | ggctgaaagc | cgcagatatt | atcggcattg | gcctggatca | ggttattccg | 780 |
| gttccggttg | atagcaatta | tcgtatggat | atcaacgagc | tggagaaaat | tatccgcgaa | 840 |
| ctggcaagta | ccgaaacccc | gattctgggc | gttgtgggcg | ctgtgggtag | taccgaagaa | 900 |
| ggtgccgttg | atggcattaa | tgaaattgca | gaactgcgta | acaagctggt | gaagaaggt | 960 |
| atctatttct | acttccacat | cgacgccgcc | tatggtggcc | atggtcgcgc | aattctgctg | 1020 |
| gatgaagata | taagctgat | cccgtataag | gaccttcaga | gtaaattcgc | cgaatataac | 1080 |
| gtgttcaccg | aagaagaaaa | cctggtgagt | gaacatacct | ataactccta | tgccgcattt | 1140 |
| ccggaagccg | aaagtgttac | cattgatccg | cataaaatgg | gctatatccc | gtatagtgca | 1200 |
| ggcggcattg | ccattcagga | tattcgcatg | cgtgatgtta | tcagctattt | cgcaacctat | 1260 |
| gtgttcgaaa | agggcgcaga | tattccggca | ctgctgggtg | cttatattct | ggaaggcagt | 1320 |
| aaagcaggcg | caaccgcagc | cagtgtttgg | gcagcacata | aaaccctgcc | gctgaatgtt | 1380 |
| accggttatg | gtaaactggt | tggtgcaagc | attgaaggcg | cccgccgttt | ttataatttt | 1440 |
| ctgagcggcc | tggaattcaa | ggtgggcgat | aaaaccattg | aagttcatcc | gctgaccgat | 1500 |
| ccggattta | atatggttga | ttacgtgttc | caggagaagg | gcaataataa | tctggtggaa | 1560 |
| atgaacgagc | tgaaccatga | atttacaac | caggcaagct | acgttaccgg | tagcatctat | 1620 |
| ggcaatgaat | atctgaccag | ccataccgat | ttcgcaattc | cggattatgg | taatagcccg | 1680 |
| tttaagtttg | tgaacaacct | gggcgtgacc | gaagaaggct | ggaaagaagc | aggtaaagtg | 1740 |
| accgttctgc | gcgccgctgt | gatgacacct | tatatgaata | aggcagagaa | cttcgactac | 1800 |
| ttcgccccga | aaattaagca | ggccatgcag | gaaaaactgg | aagccatcta | tgaagatcgt | 1860 |
| aag | | | | | | 1863 |

<210> SEQ ID NO 40
<211> LENGTH: 621
<212> TYPE: PRT
<213> ORGANISM: Artificial sequence
<220> FEATURE:
<223> OTHER INFORMATION: Engineered sequence

<400> SEQUENCE: 40

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Ala Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Glu Asn Leu
        355                 360                 365

Val Ser Glu His Thr Tyr Asn Ser Tyr Ala Ala Phe Pro Glu Ala Glu
        370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Lys Thr Leu Pro Leu Asn Val Thr Gly Tyr Gly
        450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
        610                 615                 620

<210> SEQ ID NO 41
<211> LENGTH: 1863
<212> TYPE: DNA
<213> ORGANISM: Artificial sequence
<220> FEATURE:
<223> OTHER INFORMATION: Engineered sequence

<400> SEQUENCE: 41
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat aaaccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatga agaagaagt tggtctggaa      420 tttgccaccc tgatgggcta ccaatggt tggggccata ttgttgcaga tggtagcctg        480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600

```
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac     1080
gtgttcaccg aagaagaaaa cctggtgagt gaacataccct ataacgccta tgccgcattt   1140
ccggaagccg aaagtgttac cactgatccg cataaaatgg gctatatccc gtatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgttttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaccatga attttacaac caggcaagct acgttaccgg tagcatctat    1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 42
<211> LENGTH: 621
<212> TYPE: PRT
<213> ORGANISM: Artificial sequence
<220> FEATURE:
<223> OTHER INFORMATION: Engineered sequence

<400> SEQUENCE: 42

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Lys Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
```

```
              130                 135                 140
Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Glu Asn Leu
        355                 360                 365

Val Ser Glu His Thr Tyr Asn Ala Tyr Ala Ala Phe Pro Glu Ala Glu
    370                 375                 380

Ser Val Thr Thr Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560
```

```
Phe Lys Phe Val Asn Asn Leu Gly Val Thr Glu Gly Trp Lys Glu
            565                 570                 575
Ala Gly Lys Val Thr Val Leu Arg Ala Ala Val Met Thr Pro Tyr Met
        580                 585                 590
Asn Lys Ala Glu Asn Phe Asp Tyr Phe Ala Pro Lys Ile Lys Gln Ala
        595                 600                 605
Met Gln Glu Lys Leu Glu Ala Ile Tyr Glu Asp Arg Lys
    610                 615                 620

<210> SEQ ID NO 43
<211> LENGTH: 1863
<212> TYPE: DNA
<213> ORGANISM: Artificial sequence
<220> FEATURE:
<223> OTHER INFORMATION: Engineered sequence

<400> SEQUENCE: 43
```

| | | |
|---|---|---|
| atgagcaaca ccagtttcag cgcaaaagat accgatctga gtgcactgtt tatcggtgac | 60 |
| aaagcagaaa atggtcagct gtataaggac ctgctgggca aactggttga tgaacatctg | 120 |
| ggttggcgcc agaattatat gccgcaggat ccgccgatga tcagcgccga acagcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg aatggtaac | 360 |
| aacgtggcct atgaaagcag cccggcaacc agccagatgg aagaagaagt tggtctggaa | 420 |
| tttgccaccc tgatgggcta caccaatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc gaccattgt tgccggcaaa accgattggg aactgagtaa tatgagcacc | 600 |
| aaagaaatca tggacctggt tgaagccaat ggtgacaaaa ttgatgagat caaggccaaa | 660 |
| agcgcccgcg gcggtaaaga tctggataaa ctgggtaaat ggctggttcc gcagaccaaa | 720 |
| cattatagtt ggctgaaagc cgcagatatt atcggcattg cctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta caagctggt gaaagaaggt | 960 |
| atctatttct acttccacat cgacgccgcc tatggtggct atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacatacct ataacgccta tgccgcattt | 1140 |
| ccggaagcca aagtgttac cattgatccg cataaaatgg gctatatccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaaccctgcc gctgaatgtt | 1380 |
| accggttatg tgttctggt tggtgcaagc attgaaggcg cccgccgttt ttataatttt | 1440 |
| ctgagcggcc tggaattcaa ggtgggcgat aaaaccattg aagttcatcc gctgaccgat | 1500 |
| ccggatttta atatggttga ttacgtgttc caggagaagg gcaataataa tctggtggaa | 1560 |
| atgaacgagc tgaaccatga attttacaac caggcaagct acgttaccgg tagcatctat | 1620 |
| ggcaatgaat atctgaccag ccataccgat ttcgcaattc cggattatgg taatagcccg | 1680 |

-continued

```
tttaagtttg tgaacaacct gggcgtgacc gaagaaggct ggaaagaagc aggtaaagtg      1740
accgttctgc gcgccgctgt gatgacacct tatatgaata aggcagagaa cttcgactac      1800
ttcgccccga aaattaagca ggccatgcag gaaaaactgg aagccatcta tgaagatcgt     1860
aag                                                                    1863
```

<210> SEQ ID NO 44
<211> LENGTH: 621
<212> TYPE: PRT
<213> ORGANISM: Artificial sequence
<220> FEATURE:
<223> OTHER INFORMATION: Engineered sequence

<400> SEQUENCE: 44

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
```

```
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
            355                 360                 365
Val Ser Glu His Thr Tyr Asn Ala Tyr Ala Ala Phe Pro Glu Ala Glu
370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
            435                 440                 445
Val Trp Ala Ala His Lys Thr Leu Pro Leu Asn Val Thr Gly Tyr Gly
450                 455                 460
Val Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
                500                 505                 510
Lys Gly Asn Asn Asn Leu Val Glu Met Asn Glu Leu Asn His Glu Phe
            515                 520                 525
Tyr Asn Gln Ala Ser Tyr Val Thr Gly Ser Ile Tyr Gly Asn Glu Tyr
530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
            595                 600                 605
Met Gln Glu Lys Leu Glu Ala Ile Tyr Glu Asp Arg Lys
    610                 615                 620

<210> SEQ ID NO 45
<211> LENGTH: 1863
<212> TYPE: DNA
<213> ORGANISM: Artificial sequence
<220> FEATURE:
<223> OTHER INFORMATION: Engineered sequence

<400> SEQUENCE: 45
atgagcaaca ccagtttcag cgcaaaagat accgatctga gtgcactgtt tatcggtgac      60
aaagcagaaa tggtcagct gtataaggac ctgctgggca aactggttga tgaacatctg      120
ggttggcgcc agaattatat gccgcaggat ccgccgatga tcagcgccga acagcagacc      180
agcccggaat tcgtggtac cgtgaataat atgaaggacg ttctggatga gctgagcagt      240
cgcctgcgta gtcagagcgt tccgtggcat aatgccggtc gttattgggg ccacatgaat      300
agcgaaaccc tgatgccggc aattctggcc tataattatg caatgctgtg gaatggtaac      360
aacgtggcct atgaaagcag cccggcaacc agccagatgg aagaagaagt tggtctggaa      420
```

-continued

```
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg    1020
gatgaagata taagctgatc ccgtataaga gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200 ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactgct gggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 46
<211> LENGTH: 621
<212> TYPE: PRT
<213> ORGANISM: Artificial sequence
<220> FEATURE:
<223> OTHER INFORMATION: Engineered sequence

<400> SEQUENCE: 46

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95
```

```
Gly His Met Asn Ser Glu Thr Leu Met Pro Ala Ile Leu Ala Tyr Asn
            100                 105                 110

Tyr Ala Met Leu Trp Asn Gly Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Leu Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
```

```
               515                 520                 525
Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
                595                 600                 605

Met Gln Glu Lys Leu Glu Ala Ile Tyr Glu Asp Arg Lys
610                 615                 620

<210> SEQ ID NO 47
<211> LENGTH: 1863
<212> TYPE: DNA
<213> ORGANISM: Artificial sequence
<220> FEATURE:
<223> OTHER INFORMATION: Engineered sequence

<400> SEQUENCE: 47
```

| | | |
|---|---|---|
| atgagcaaca ccagtttcag cgcaaaagat accgatctga gtgcactgtt tatcggtgac | 60 |
| aaagcagaaa atggtcagct gtataaggac ctgctgggca aactggttga tgaacatctg | 120 |
| ggttggcgcc agaattatat gccgcaggat ccgccgatga tcagcgccga acagcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg gaatggtaac | 360 |
| aacgtggcct atgaaagcag cccggcaacc agccagatgg aagaagaagt tggtctggaa | 420 |
| tttgccaccc tgatgggcta caatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc cgaccattgt tgccggcaaa accgattggg aactgagtaa tatgagcacc | 600 |
| aaagaaatca tggacctggt tgaagccctg ggtgacaaaa ttgatgagat caaggccaaa | 660 |
| agcgcccgcg cgcgtaaaga tctggataaa ctgggtaaat ggctggttcc gcagaccaaa | 720 |
| cattatagtt ggctgaaagc cgcagatatt atcggcattg cctggatca ggttattccg | 780 |
| gttccggttg atagcaatta tcgtatggat atcaacgagc tggagaaaat atccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta acaagctggt gaaagaaggt | 960 |
| atctatttct acttccacat cgacgccgcc tatggtggct atggtcgcgc aattctgctg | 1020 |
| gatgaagata taagctgat cccgtataag accttcaga gtaaattcgc cgaatataac | 1080 |
| gtgttcaccg aagaagaaaa cctggtgagt gaacatacct ataacgccta tgccgcattt | 1140 |
| ccggaagccg aaagtgttac cattgatccg cataaaatgg ctatatccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaccctgcc gctgaatgtt | 1380 |
| accggttatg gtaaactggt tggtgcaagc attgaaggcg cccgccgttt ttataatttt | 1440 |
| ctgagcggcc tggaattcaa ggtgggcgat aaaaccattg aagttcatcc gctgaccgat | 1500 |

-continued

```
ccggatttta atatggttga ttacgtgttc caggagaagg gcaataataa tctggtggaa    1560
atgaacgagc tgaaccatga attttacgac caggcaagct acgttaccgg tagcatctat    1620
ggcaatgaat atctgaccag ccataccgat tcgcaattc cggattatgg taatagcccg      1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                   1863
```

<210> SEQ ID NO 48
<211> LENGTH: 621
<212> TYPE: PRT
<213> ORGANISM: Artificial sequence
<220> FEATURE:
<223> OTHER INFORMATION: Engineered sequence

<400> SEQUENCE: 48

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Leu Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285
```

```
Leu Gly Val Gly Val Val Gly Ser Thr Glu Glu Gly Ala Val Asp
        290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
        355                 360                 365
Val Ser Glu His Thr Tyr Asn Ala Tyr Ala Ala Phe Pro Glu Ala Glu
370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
        435                 440                 445
Val Trp Ala Ala His Lys Thr Leu Pro Leu Asn Val Thr Gly Tyr Gly
450                 455                 460
Lys Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Asn Leu Val Glu Met Asn Glu Leu Asn His Glu Phe
        515                 520                 525
Tyr Asp Gln Ala Ser Tyr Val Thr Gly Ser Ile Tyr Gly Asn Glu Tyr
530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
        595                 600                 605
Met Gln Glu Lys Leu Glu Ala Ile Tyr Glu Asp Arg Lys
610                 615                 620
```

<210> SEQ ID NO 49
<211> LENGTH: 1863
<212> TYPE: DNA
<213> ORGANISM: Artificial sequence
<220> FEATURE:
<223> OTHER INFORMATION: Engineered sequence

<400> SEQUENCE: 49
atgagcaaca ccagtttcag cgcaaaagat accgatctga gtgcactgtt tatcggtgac       60
aaagcagaaa atggtcagct gtataaggac ctgctgggca aactggttga tgaacatctg      120
ggttggcgcc agaattatat gccgcaggat ccgccgatga tcagcgccga acagcagacc      180

-continued

| | |
|---|---|
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg gaatggtaac | 360 |
| aacgtggcct atgaaagcag cccggcaacc agccagatgg aagaagaagt tggtctggaa | 420 |
| tttgccaccc tgatgggcta caccaatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc cgaccattgt tgccggcaaa accgattggg aactgagtaa tatgagcacc | 600 |
| aaagaaatca tggacctggt tgaagccaat ggtgacaaaa ttgatgagat caaggccaaa | 660 |
| agcgcccgcg gcggtaaaga tctggataaa ctgggtaaat ggctggttcc gcagaccaaa | 720 |
| cattatagtt ggctgaaagc cgcagatatt atcggcattg gcctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg cggtgggtag taccgaagaa | 900 |
| ggtgccgttg atggcattaa tgaaattgca gaactgcgta caagctggt gaaagaaggt | 960 |
| atctatttct acttccacat cgacgccgcc tatggtggct atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacatacct ataacgccta tgccgcattt | 1140 |
| ccggaagccg aaagtgttac cattgatccg cataaaatgg gctatatccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaaccctgcc gctgaatgtt | 1380 |
| accggttatg gtaaactggt tggtgcaagc attgaaggcg cccgccgttt ttataatttt | 1440 |
| ctgagcggcc tggaattcaa ggtgggcgat aaaaccattg aagttcatcc gctgaccgat | 1500 |
| ccggattta atatggttga ttacgtgttc caggagaagg gcaataataa tctggtggaa | 1560 |
| atgaacgagc tgaaccatga atttacaac caggcaagct actggaccgg tagcatctat | 1620 |
| ggcaatgaat atctgaccag ccataccgat ttcgcaattc cggattatgg taatagcccg | 1680 |
| tttaagtttg tgaacaacct gggcgtgacc gaagaaggct ggaaagaagc aggtaaagtg | 1740 |
| accgttctgc gcgccgctgt gatgacacct tatatgaata aggcagagaa cttcgactac | 1800 |
| ttcgccccga aaattaagca ggccatgcag gaaaaactgg aagccatcta tgaagatcgt | 1860 |
| aag | 1863 |

<210> SEQ ID NO 50
<211> LENGTH: 621
<212> TYPE: PRT
<213> ORGANISM: Artificial sequence
<220> FEATURE:
<223> OTHER INFORMATION: Engineered sequence

<400> SEQUENCE: 50

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

```
Arg Gly Thr Val Asn Asn Met Lys Asp Val Leu Asp Glu Leu Ser Ser
 65                  70                  75                  80

Arg Leu Arg Ser Gln Ser Val Pro Trp His Asn Ala Gly Arg Tyr Trp
                 85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Ala Val Gly Ser Thr Glu Glu Gly Ala Val Asp
290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480
```

```
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Asn Leu Val Glu Met Asn Glu Leu Asn His Glu Phe
        515                 520                 525
Tyr Asn Gln Ala Ser Tyr Trp Thr Gly Ser Ile Tyr Gly Asn Glu Tyr
    530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
        595                 600                 605
Met Gln Glu Lys Leu Glu Ala Ile Tyr Glu Asp Arg Lys
    610                 615                 620
```

<210> SEQ ID NO 51
<211> LENGTH: 1863
<212> TYPE: DNA
<213> ORGANISM: Artificial sequence
<220> FEATURE:
<223> OTHER INFORMATION: Engineered sequence

<400> SEQUENCE: 51

| | | | | | |
|---|---|---|---|---|---|
| atgagcaaca | ccagtttcag | cgcaaaagat | accgatctga | gtgcactgtt | tatcggtgac | 60 |
| aaagcagaaa | atggtcagct | gtataaggac | ctgctgggca | aactggttga | tgaacatctg | 120 |
| ggttggcgcc | agaattatat | gccgcaggat | ccgccgatga | tcagcgccga | acagcagacc | 180 |
| agcccggaat | tcgtggtac | cgtgaataat | atgaaggacg | ttctggatga | gctgagcagt | 240 |
| cgcctgcgta | gtcagagcgt | tccgtggcat | aatgccggtc | gttattgggg | ccacatgaat | 300 |
| agcgaaaccc | tgatgccggc | aattctggcc | tataattatg | caatgctgtg | aatggtaac | 360 |
| aacgtggcct | atgaaagcag | cccggcaacc | agccagatga | agaagaagt | tggtctggaa | 420 |
| tttgccaccc | tgatgggcta | taccaatggt | tggggccata | ttgttgcaga | tggtagcctg | 480 |
| gcaaatctgg | aaggcctgtg | gtatgcacgc | aatattaaga | gctgccgtt | tgccatgaaa | 540 |
| gccgttgatc | cgaccattgt | tgccggcaaa | accgattggg | aactgagtaa | tatgagcacc | 600 |
| aaagaaatca | tggacctggt | tgaagccaat | ggtgacaaaa | ttgatgagat | caaggccaaa | 660 |
| agcgcccgcg | gcggtaaaga | tctggataaa | ctgggtaaat | ggctggttcc | gcagaccaaa | 720 |
| cattatagtt | ggctgaaagc | gcagatatt | tccggcattg | gctggatca | ggttattccg | 780 |
| gttccggttg | atagcaatta | tcgtatggat | atcaacgagc | tggagaaaat | tatccgcgaa | 840 |
| ctggcaagta | ccgaaacccc | gattctgggc | gttgtgggcg | ttgtgggtag | taccgaagaa | 900 |
| ggtgccgttg | atggcattaa | tgaaattgca | gaactgcgta | caagctggt | gaagaaggt | 960 |
| atctatttct | acttccacat | cgacgccgcc | tatggtggct | atggtcgcgc | aattctgctg | 1020 |
| gatgaagata | taagctgat | cccgtataag | gaccttcaga | gtaaattcgc | cgaatataac | 1080 |
| gtgttcaccg | aagaagaaaa | cctggtgagt | gaacataccct | ataacgccta | tgccgcattt | 1140 |
| ccggaagccg | aaagtgttac | cattgatccg | cataaaatgg | ctatatccc | gtatagtgca | 1200 |
| ggcggcattg | ccattcagga | tattcgcatg | cgtgatgtta | tcagctattt | cgcaacctat | 1260 |

```
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacgac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                1863
```

<210> SEQ ID NO 52
<211> LENGTH: 621
<212> TYPE: PRT
<213> ORGANISM: Artificial sequence
<220> FEATURE:
<223> OTHER INFORMATION: Engineered sequence

<400> SEQUENCE: 52

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255
```

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asp Gln Ala Ser Tyr Val Thr Gly Ser Ile Tyr Gly Asn Glu Tyr
530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
610                 615                 620

<210> SEQ ID NO 53
<211> LENGTH: 1863
<212> TYPE: DNA
<213> ORGANISM: Artificial sequence
<220> FEATURE:
<223> OTHER INFORMATION: Engineered sequence

<400> SEQUENCE: 53

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt     240
cgcctgcgta gtcaaagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg cggtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc aggagaagg gcaataataa tctggtggaa    1560
atgaacgagc tgaccatga tttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 54
<211> LENGTH: 621
<212> TYPE: PRT
<213> ORGANISM: Artificial sequence
<220> FEATURE:
<223> OTHER INFORMATION: Engineered sequence

<400> SEQUENCE: 54

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu

```
                20                  25                  30
Gly Lys Leu Val Asp Glu His Leu Gly Trp Arg Gln Asn Tyr Met Pro
            35                  40                  45
Gln Asp Pro Pro Met Ile Ser Ala Glu Gln Gln Thr Ser Pro Glu Phe
 50                  55                  60
Arg Gly Thr Val Asn Asn Met Lys Asp Val Leu Asp Glu Leu Ser Ser
 65                  70                  75                  80
Arg Leu Arg Ser Gln Ser Val Pro Trp His Asn Ala Gly Arg Tyr Trp
            85                  90                  95
Gly His Met Asn Ser Glu Thr Leu Met Pro Ala Ile Leu Ala Tyr Asn
                100                 105                 110
Tyr Ala Met Leu Trp Asn Gly Asn Val Ala Tyr Glu Ser Ser Pro
            115                 120                 125
Ala Thr Ser Gln Met Glu Glu Val Gly Leu Glu Phe Ala Thr Leu
            130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
                180                 185                 190
Trp Glu Leu Ser Asn Met Ser Thr Lys Glu Ile Met Asp Leu Val Glu
            195                 200                 205
Ala Asn Gly Asp Lys Ile Asp Glu Ile Lys Ala Lys Ser Ala Arg Gly
            210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
                260                 265                 270
Glu Leu Glu Lys Ile Ile Arg Glu Leu Ala Ser Thr Glu Thr Pro Ile
            275                 280                 285
Leu Gly Val Val Gly Ala Val Gly Ser Thr Glu Glu Gly Ala Val Asp
            290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
            355                 360                 365
Val Ser Glu His Thr Tyr Asn Ala Tyr Ala Ala Phe Pro Glu Ala Glu
            370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
                420                 425                 430
Gly Ala Tyr Ile Leu Glu Gly Ser Lys Ala Gly Ala Thr Ala Ala Ser
            435                 440                 445
```

```
Val Trp Ala Ala His Lys Thr Leu Pro Leu Asn Val Thr Gly Tyr Gly
    450                 455                 460
Lys Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Asn Leu Val Glu Met Asn Glu Leu Asn His Glu Phe
        515                 520                 525
Tyr Asn Gln Ala Ser Tyr Val Thr Gly Ser Ile Tyr Gly Asn Glu Tyr
    530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
        595                 600                 605
Met Gln Glu Lys Leu Glu Ala Ile Tyr Glu Asp Arg Lys
    610                 615                 620

<210> SEQ ID NO 55
<211> LENGTH: 1863
<212> TYPE: DNA
<213> ORGANISM: Artificial sequence
<220> FEATURE:
<223> OTHER INFORMATION: Engineered sequence

<400> SEQUENCE: 55
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg tatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccctg ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg cctggatca ggttattccg     780
gttccggttg atagcaatta tcgtatggat atcaacgagc tggagaaaat tatccgcgaa     840
ctggcaagta ccgaaacccc gattctgggc gttgtgggcg cggtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
```

```
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaccctgccg ctgaatgtt     1380 accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga atttacaac caggcaagct actggaccgg tagcatctat      1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                   1863

<210> SEQ ID NO 56
<211> LENGTH: 621
<212> TYPE: PRT
<213> ORGANISM: Artificial sequence
<220> FEATURE:
<223> OTHER INFORMATION: Engineered sequence

<400> SEQUENCE: 56

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
                20                  25                  30

Gly Lys Leu Val Asp Glu His Leu Gly Trp Arg Gln Asn Tyr Met Pro
            35                  40                  45

Gln Asp Pro Pro Met Ile Ser Ala Glu Gln Gln Thr Ser Pro Glu Phe
        50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
                100                 105                 110

Tyr Ala Met Leu Trp Asn Gly Asn Asn Val Ala Tyr Glu Ser Ser Pro
            115                 120                 125

Ala Thr Ser Gln Met Glu Glu Val Gly Leu Glu Phe Ala Thr Leu
        130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Leu Gly Asp Lys Ile Asp Glu Ile Lys Ala Lys Ser Ala Arg Gly
```

```
                210                 215                 220
Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
                260                 265                 270

Glu Leu Glu Lys Ile Ile Arg Glu Leu Ala Ser Thr Glu Thr Pro Ile
                275                 280                 285

Leu Gly Val Val Gly Ala Val Gly Ser Thr Glu Glu Gly Ala Val Asp
                290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
                355                 360                 365

Val Ser Glu His Thr Tyr Asn Ala Tyr Ala Ala Phe Pro Glu Ala Glu
                370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Lys Thr Leu Pro Leu Asn Val Thr Gly Tyr Gly
                450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
                515                 520                 525

Tyr Asn Gln Ala Ser Tyr Trp Thr Gly Ser Ile Tyr Gly Asn Glu Tyr
                530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
                595                 600                 605

Met Gln Glu Lys Leu Glu Ala Ile Tyr Glu Asp Arg Lys
610                 615                 620

<210> SEQ ID NO 57
```

<211> LENGTH: 1863
<212> TYPE: DNA
<213> ORGANISM: Artificial sequence
<220> FEATURE:
<223> OTHER INFORMATION: Engineered sequence

<400> SEQUENCE: 57

| | |
|---|---|
| atgagcaaca ccagtttcag cgcaaaagat accgatctga gtgcactgtt tatcggtgac | 60 |
| aaagcagaaa atggtcagct gtataaggac ctgctgggca aactggttga tgaacatctg | 120 |
| ggttggcgcc agaattatat gccgcaggat ccgccgatga tcagcgccga acagcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg gaatggtaac | 360 |
| aacgtggcct atgaaagcag cccggcaacc agccagatgg aagaagaagt tggtctggaa | 420 |
| tttgccaccc tgatgggcta taccaatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc cgaccattgt tgccggcaaa accgattggg aactgagtaa tatgagcacc | 600 |
| aaagaaatca tggacctggt tgaagccaat ggtgacaaaa ttgatgagat caaggccaaa | 660 |
| agcgcccgcg cggtaaaga tctggataaa ctgggtaaat ggctggttcc gcagaccaaa | 720 |
| cattatagtt ggctgaaagc cgcagatatt atccggcattg cctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta acaagctggt gaaagaaggt | 960 |
| atctatttct acttccacat cgacgccgcc tatggtggct atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacataccc taacgcccta tgccgcattt | 1140 |
| ccggaagccg aaagtgttac caccgatccg cataaaatgg ctatatccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaaccctgcc gctgaatgtt | 1380 |
| accggttatg gtaaactggt tggtgcaagc attgaaggcg cccgccgttt ttataattt | 1440 |
| ctgagcggcc tggaattcaa ggtgggcgat aaaaccattg aagttcatcc gctgaccgat | 1500 |
| ccggatttta atatggttga ttacgtgttc caggagaagg gcaataataa tctggtggaa | 1560 |
| atgaacgagc tgaaccatga attttacaac caggcaagct acgttaccgg tagcatctat | 1620 |
| ggcaatgaat atctgaccag ccataccgat ttcgcaattc cggattatgg taatagcccg | 1680 |
| tttaagtttg tgaacaacct gggcgtgacc gaagaaggct ggaaagaagc aggtaaagtg | 1740 |
| accgttctgc gcgccgctgt gatgacacct tatatgaata ggcagagaa cttcgactac | 1800 |
| ttcgccccga aaattaagca ggccatgcag gaaaaactgg aagccatcta tgaagatcgt | 1860 |
| aag | 1863 |

<210> SEQ ID NO 58
<211> LENGTH: 621
<212> TYPE: PRT
<213> ORGANISM: Artificial sequence
<220> FEATURE:
<223> OTHER INFORMATION: Engineered sequence

<400> SEQUENCE: 58

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Thr Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
```

```
                       405                 410                 415
Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
        450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
610                 615                 620

<210> SEQ ID NO 59
<211> LENGTH: 1863
<212> TYPE: DNA
<213> ORGANISM: Artificial sequence
<220> FEATURE:
<223> OTHER INFORMATION: Engineered sequence

<400> SEQUENCE: 59
atgagcaaca ccagtttcag cgcaaaagat accgatctga gtgcactgtt tatcggtgac    60
aaagcagaaa atggtcagct gtataaggaa ctgctgggca aactggttga tgaacatctg   120
ggttggcgcc agaattatat gccgcaggat ccgtcgatga tcagcgccga acagcagacc   180
agcccggaat tcgtggtac cgtgaataat atgcgtgacg ttctggatga gctgagcagt   240
cgcctgcgta gtcagagcgt tccgtggcat aatgccggtc gttattgggg ccacatgaat   300
agcgaaaccc tgatgccggc aattctggcc tataattatg caatgctgtg gaatggtaac   360
aacgtggcct atgaaagcag cccggcaacc agccagatgg aagaagaagt tggtctggaa   420
tttgccaccc tgatgggcta caccaatggt tggggccata ttgttgcaga tggtagcctg   480
gcaaatctgg aaggcctgtg gtatgcacgc aatattaaga gcctgccgtt tgccatgaaa   540
gccgttgatc cgaccattgt tgccggcaaa accgattggg aactgagtaa tatgagcacc   600
aaagaaatca tggacctggt tgaagccaat ggtgacaaaa ttgatgagat caaggccaaa   660
agcgcccgcg gcggtaaaga tctggataaa ctgggtaaat ggctggttcc gcagaccaaa   720
cattatagtt ggctgaaagc cgcagatatt atcggcattg cctgatca ggttattccg   780 gttccggttg atagcaatta tcgtatggat atcaacgagc tggagaaaat tatccgcgaa   840
```

-continued

```
ctggcaagta ccgaaacccc gattctgggc gttgtgggcg ttgtgggtag taccgaagaa        900
ggtgccgttg atggcattaa tgaaattgca gaactgcgta acaagctggt gaaagaaggt        960
atctatttct acttccacat cgacgccgcc tatggtggct atggtcgcgc aattctgctg       1020
gatgaagata taagctgat cccgtataag gaccttcaga gtaaattcgc cgaatataac       1080
gtgttcaccg aagaagaaaa cctggtgagt gaacatacct ataacgccta tgccgcattt       1140
ccggaagccg aaagtgttac cattgatccg cataaaatgg ctatatcccg gtatagtgca       1200
ggcggcattg ccattcagga tattcgcatg cgtgatgtta tcagctattt cgcaacctat       1260
gtgttcgaaa agggcgcaga tattccggca ctgctgggtg cttatattct ggaaggcagt       1320
aaagcaggcg caaccgcagc cagtgttggg gcagcacata aaaccctgcc gctgaatgtt       1380
accggttatg gtaaactggt tggtgcaagc attgaaggcg cccgccgttt ttataatttt       1440
ctgagcggcc tggaattcaa ggtgggcgat aaaaccattg aagttcatcc gctgaccgat       1500
ccggatttta atatggttga ttacgtgttc caggagaagg gcaataataa tctggtggaa       1560
atgaacgagc tgaaccatga attttacaac caggcaagct acgttaccgg tagcatctat       1620
ggcaatgaat atctgaccag ccataccgat ttcgcaattc cggattatgg taatagcccg       1680
tttaagtttg tgaacaacct gggcgtgacc gaagaaggct ggaaagaagc aggtaaagtg       1740
accgttctgc gcgccgctgt gatgacacct tatatgaata aggcagagaa cttcgactac       1800
ttcgccccga aaattaagca ggccatgcag gaaaaactgg aagccatcta tgaagatcgt       1860
aag                                                                    1863
```

<210> SEQ ID NO 60
<211> LENGTH: 621
<212> TYPE: PRT
<213> ORGANISM: Artificial sequence
<220> FEATURE:
<223> OTHER INFORMATION: Engineered sequence

<400> SEQUENCE: 60

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Glu Leu Leu
            20                  25                  30

Gly Lys Leu Val Asp Glu His Leu Gly Trp Arg Gln Asn Tyr Met Pro
        35                  40                  45

Gln Asp Pro Ser Met Ile Ser Ala Glu Gln Thr Ser Pro Glu Phe
    50                  55                  60

Arg Gly Thr Val Asn Asn Met Arg Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175
```

```
Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
```

```
              595                 600                 605
Met Gln Glu Lys Leu Glu Ala Ile Tyr Glu Asp Arg Lys
            610                 615                 620

<210> SEQ ID NO 61
<211> LENGTH: 1863
<212> TYPE: DNA
<213> ORGANISM: Artificial sequence
<220> FEATURE:
<223> OTHER INFORMATION: Engineered sequence

<400> SEQUENCE: 61
```

| | | | | | |
|---|---|---|---|---|---|
| atgagcaaca | ccagtttcag | cgcaaaagat | accgatctga | gtgcactgtt | tatcggtgac | 60 |
| aaagcagaaa | atggtcagct | gtataaggaa | ctgctgggca | aactggttga | tgaacatctg | 120 |
| ggttggcgcc | agaattatat | gccgcaggat | ccgccgatga | tcagcgccga | acagcagacc | 180 |
| agcccggaat | tcgtggtac | cgtgaataat | atgcgtgacg | ttctggatga | gctgagcagt | 240 |
| cgcctgcgta | gtcagagcgt | tccgtggcat | aatgccggtc | gttattgggg | ccacatgaat | 300 |
| agcgaaaccc | tgatgccggc | aattctggcc | tataattatg | caatgctgtg | aatggtaac | 360 |
| aacgtggcct | atgaaagcag | cccggcaacc | agccagatgg | aagaagaagt | tggtctggaa | 420 |
| tttgccaccc | tgatgggcta | taccaatggt | tggggccata | ttgttgcaga | tggtagcctg | 480 |
| gcaaatctgg | aaggcctgtg | gtatgcacgc | aatattaaga | gcctgccgtt | tgccatgaaa | 540 |
| gccgttgatc | cgaccattgt | tgccggcaaa | accgattggg | aactgagtaa | tatgagcacc | 600 |
| aaagaaatca | tggacctggt | tgaagccaat | ggtgacaaaa | ttgatgagat | caaggccaaa | 660 |
| agcgcccgcg | gcggtaaaga | tctggataaa | ctgggtaaat | ggctggttcc | gcagaccaaa | 720 |
| cattatagtt | ggctgaaagc | cgcagatatt | atcggcattg | gcctggatca | ggttattccg | 780 |
| gttccggttg | atagcaatta | tcgtatggat | atcaacgagc | tggagaaaat | tatccgcgaa | 840 |
| ctggcaagta | ccgaaacccc | gattctgggc | gttgtgggcg | ttgtgggtag | taccgaagaa | 900 |
| ggtgccgttg | atggcattaa | tgaaattgca | gaactgcgta | acaagctggt | gaagaaggt | 960 |
| atctatttct | acttccacat | cgacgccgcc | tatggtggct | atggtcgcgc | aattctgctg | 1020 |
| gatgaagata | taagctgat | cccgtataag | gaccttcaga | gtaaattcgc | cgaatataac | 1080 |
| gtgttcaccg | aagaagaaaa | cctggtgagt | gaacatacct | ataacgccta | tgccgcatt | 1140 |
| ccggaagccg | aaagtgttac | cattgatccg | cataaaatgg | gctatatccc | gtatagtgca | 1200 |
| ggcggcattg | ccattcagga | tattcgcatg | cgtgatgtta | tcagctattt | cgcaacctat | 1260 |
| gtgttcgaaa | agggcgcaga | tattccggca | ctgctgggtg | cttatattct | ggaaggcagt | 1320 |
| aaagcaggcg | caaccgcagc | cagtgtttgg | gcagcacata | aaaccctgcc | gctgaatgtt | 1380 |
| accggttatg | gtaaactggt | tggtgcaagc | attgaaggcg | cccgccgttt | ttataatttt | 1440 |
| ctgagcggcc | tggaattcaa | ggtgggcgat | aaaaccattg | aagttcatcc | gctgaccgat | 1500 |
| ccggatttta | tatggttga | ttacgtgttc | caggagaagg | gcaataataa | tctggtggaa | 1560 |
| atgaacgagc | tgaaccatga | attttacaac | caggcaagct | acgttaccgg | tagcatctat | 1620 |
| ggcaatgaat | atctgaccag | ccataccgat | ttcgcaattc | cggattatgg | taatagcccg | 1680 |
| tttaagtttg | tgaacaacct | gggcgtgacc | gaagaaggct | ggaaagaagc | aggtaaagtg | 1740 |
| accgttctgc | gcgccgctgt | gatgacacct | tatatgaata | ggcagagaa | cttcgactac | 1800 |
| ttcgccccga | aaattaagca | ggccatgcag | gaaaaactgg | aagccatcta | tgaagatcgt | 1860 |
| aag | | | | | | 1863 |

```
<210> SEQ ID NO 62
<211> LENGTH: 621
<212> TYPE: PRT
<213> ORGANISM: Artificial sequence
<220> FEATURE:
<223> OTHER INFORMATION: Engineered sequence

<400> SEQUENCE: 62

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Glu Leu Leu
                20                  25                  30

Gly Lys Leu Val Asp Glu His Leu Gly Trp Arg Gln Asn Tyr Met Pro
            35                  40                  45

Gln Asp Pro Pro Met Ile Ser Ala Glu Gln Gln Thr Ser Pro Glu Phe
        50                  55                  60

Arg Gly Thr Val Asn Asn Met Arg Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
        130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365
```

| | | | | | | | | | | | |
|---|---|---|---|---|---|---|---|---|---|---|---|
|Val|Ser|Glu|His|Thr|Tyr|Asn|Ala|Tyr|Ala|Ala|Phe Pro Glu Ala Glu|
| |370| | | |375| | | |380| | |

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
            485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 63
<211> LENGTH: 1863
<212> TYPE: DNA
<213> ORGANISM: Artificial sequence
<220> FEATURE:
<223> OTHER INFORMATION: Engineered sequence

<400> SEQUENCE: 63

```
atgagcaaca ccagtttcag cgcaaaagat accgatctga gtgcactgtt tatcggtgac      60
aaagcagaaa atggtcagct gtataaggaa ctgctgggca aactggttga tgaacatctg     120
ggttggcgcc agaattatat gccgcaggat ccgtcgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta ccaatggtg tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
```

```
agcgcccgcg gcggtaaaga tctggataaa ctgggtaaat ggctggttcc gcagaccaaa    720
cattatagtt ggctgaaagc cgcagatatt atcggcattg cctggatca ggttattccg     780 gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt     960 atctatttct acttccacat cgacgccgcc tatggtggct atggtcgcgc aattctgctg   1020
gatgaagata taagctgat cccgtataag gaccttcaga gtaaattcgc cgaatataac    1080
gtgttcaccg aagaagaaaa cctggtgagt gaacatacct ataacgccta tgccgcattt   1140
ccggaagccg aaagtgttac cattgatccg cataaaatgg ctatatccc gtatagtgca    1200 ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 64
<211> LENGTH: 621
<212> TYPE: PRT
<213> ORGANISM: Artificial sequence
<220> FEATURE:
<223> OTHER INFORMATION: Engineered sequence

<400> SEQUENCE: 64

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Glu Leu Leu
            20                  25                  30

Gly Lys Leu Val Asp Glu His Leu Gly Trp Arg Gln Asn Tyr Met Pro
        35                  40                  45

Gln Asp Pro Ser Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140
```

-continued

```
Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
            165                 170                 175

Phe Ala Met Lys Ala Val Asp Pro Thr Ile Val Ala Gly Lys Thr Asp
        180                 185                 190

Trp Glu Leu Ser Asn Met Ser Thr Lys Glu Ile Met Asp Leu Val Glu
    195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560
```

```
Phe Lys Phe Val Asn Asn Leu Gly Val Thr Glu Gly Trp Lys Glu
            565                 570                 575

Ala Gly Lys Val Thr Val Leu Arg Ala Ala Val Met Thr Pro Tyr Met
        580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
610                 615                 620

<210> SEQ ID NO 65
<211> LENGTH: 1863
<212> TYPE: DNA
<213> ORGANISM: Artificial sequence
<220> FEATURE:
<223> OTHER INFORMATION: Engineered sequence

<400> SEQUENCE: 65
atgagcaaca ccagtttcag cgcaaaagat accgatctga gtgcactgtt tatcggtgac      60
aaagcagaaa atggtcagct gtataaggac ctgctgggca actggttga tgaacatctg     120
ggttggcgcc gtaactatat gccgcaggat ccgccgatga tcagctcgga cagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcgtaaaga tctggataaa ctgggtaaat ggctggttcc gcagaccaaa     720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgttttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
```

```
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 66
<211> LENGTH: 621
<212> TYPE: PRT
<213> ORGANISM: Artificial sequence
<220> FEATURE:
<223> OTHER INFORMATION: Engineered sequence

<400> SEQUENCE: 66

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Arg Asn Tyr Met Pro
        35                  40                  45

Gln Asp Pro Pro Met Ile Ser Ser Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335
```

```
Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 67
<211> LENGTH: 1863
<212> TYPE: DNA
<213> ORGANISM: Artificial sequence
<220> FEATURE:
<223> OTHER INFORMATION: Engineered sequence

<400> SEQUENCE: 67
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc gtaactatat gccgcaggat ccgccgatga tcagcacgga acgtcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
```

```
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt    960 atctatttct acttccacat cgacgccgcc tatggtggct atggtcgcgc aattctgctg    1020
gatgaagata ataagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200 ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgttttgg gcagcacatc gtaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga atttttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                   1863
```

<210> SEQ ID NO 68
<211> LENGTH: 621
<212> TYPE: PRT
<213> ORGANISM: Artificial sequence
<220> FEATURE:
<223> OTHER INFORMATION: Engineered sequence

<400> SEQUENCE: 68

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Arg Asn Tyr Met Pro
        35                  40                  45

Gln Asp Pro Pro Met Ile Ser Thr Glu Arg Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
```

```
                100                 105                 110
Tyr Ala Met Leu Trp Asn Gly Asn Asn Val Ala Tyr Glu Ser Ser Pro
            115                 120                 125

Ala Thr Ser Gln Met Glu Glu Val Gly Leu Glu Phe Ala Thr Leu
130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
            165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
            210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
            245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
            290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
            325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
            370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Arg Thr Leu Pro Leu Asn Val Thr Gly Tyr Gly
            450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
            485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
            515                 520                 525
```

```
Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 69
<211> LENGTH: 1863
<212> TYPE: DNA
<213> ORGANISM: Artificial sequence
<220> FEATURE:
<223> OTHER INFORMATION: Engineered sequence

<400> SEQUENCE: 69
atgagcaaca ccagtttcag cgcaaaagat accgatctga gtgcactgtt tatcggtgac     60
aaagcagaaa atggtcagct gtataaggac ctgctgggca aactggttga tgaacatctg    120
ggttggcgcc gtaactatat gccgcaggat ccgccgatga tcagcgcgga cagcagacc    180 agcccggaat tcgtggtac cgtgaataat atgaaggacg ttctggatga gctgagcagt    240
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta ccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg cggtaaaga tctggataaa ctgggtaaat ggctggttcc gcagaccaaa    720
cattatagtt ggctgaaagc cgcagatatt atcggcattg cctggatca ggttattccg    780 gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt    960 atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatccc gtatagtgca   1200 ggcggcattg ccattcagga tattcgcatg cgtgatgtta tcagctattt cgcaaccctat   1260 gtgttcgaaa agggcgcaga tattccggca ctgctgggtg cttatattct ggaaggcagt   1320
aaagcaggcg caaccgcagc cagtgtttgg gcagcacatc gtaccctgcc gctgaatgtt   1380
accggttatg gtaaactggt tggtgcaagc attgaaggcg cccgccgttt ttataattttt   1440 ctgagcggcc tggaattcaa ggtgggcgat aaaaccattg aagttcatcc gctgaccgat   1500
```

```
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 70
<211> LENGTH: 621
<212> TYPE: PRT
<213> ORGANISM: Artificial sequence
<220> FEATURE:
<223> OTHER INFORMATION: Engineered sequence

<400> SEQUENCE: 70

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Arg Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
```

```
                290                 295                 300
Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
                355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
                435                 440                 445

Val Trp Ala Ala His Arg Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
                530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
                595                 600                 605

Met Gln Glu Lys Leu Glu Ala Ile Tyr Glu Asp Arg Lys
610                 615                 620

<210> SEQ ID NO 71
<211> LENGTH: 1863
<212> TYPE: DNA
<213> ORGANISM: Artificial sequence
<220> FEATURE:
<223> OTHER INFORMATION: Engineered sequence

<400> SEQUENCE: 71
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaactatat gccgcaggat ccgccgatga tcagctcgga acagcagacc     180
agcccggact tcgtggtac cgtgaataat atgaaggacg ttctggatga gctgagcagt     240
```

```
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta taccaatggt tggggccata ttgttgcaga tggtagcctg    480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcgtaaaga tctggataaa ctgggtaaat ggctggttcc gcagaccaaa    720
cattatagtt ggctgaaagc cgcagatatt atcggcattg cctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatcccc gtatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgttttgg gcagcacatc gtaccctgcc gctgaatgtt   1380
accggttatg gtaaactggt tggtgcaagc attgaaggcg cccgccgttt ttataattt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga atttttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggcg ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                  1863
```

<210> SEQ ID NO 72
<211> LENGTH: 621
<212> TYPE: PRT
<213> ORGANISM: Artificial sequence
<220> FEATURE:
<223> OTHER INFORMATION: Engineered sequence

<400> SEQUENCE: 72

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ser Glu Gln Gln Thr Ser Pro Asp Phe
    50                  55                  60

-continued

```
Arg Gly Thr Val Asn Asn Met Lys Asp Val Leu Asp Glu Leu Ser Ser
 65                  70                  75                  80

Arg Leu Arg Ser Gln Ser Val Pro Trp His Asn Ala Gly Arg Tyr Trp
                 85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Arg Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
```

|     | 485 |     |     |     | 490 |     |     |     | 495 |     |     |
| --- | --- | --- | --- | --- | --- | --- | --- | --- | --- | --- | --- |
| Pro | Leu | Thr | Asp | Pro | Asp | Phe | Asn | Met | Val | Asp | Tyr | Val | Phe | Gln | Glu |
|     |     |     | 500 |     |     |     |     | 505 |     |     |     |     | 510 |     |     |

Lys Gly Asn Asn Asn Leu Val Glu Met Asn Glu Leu Asn His Glu Phe
          515                 520             525

Tyr Asn Gln Ala Ser Tyr Val Thr Gly Ser Ile Tyr Gly Asn Glu Tyr
    530               535               540

Leu Thr Ser His Thr Asp Phe Ala Ile Pro Asp Tyr Gly Asn Ser Pro
545             550               555            560

Phe Lys Phe Val Asn Asn Leu Gly Val Thr Glu Glu Gly Trp Lys Glu
          565               570            575

Ala Gly Lys Val Thr Val Leu Arg Ala Ala Val Met Thr Pro Tyr Met
        580               585            590

Asn Lys Ala Glu Asn Phe Asp Tyr Phe Ala Pro Lys Ile Lys Gln Ala
    595               600            605

Met Gln Glu Lys Leu Glu Ala Ile Tyr Glu Asp Arg Lys
610             615               620

<210> SEQ ID NO 73
<211> LENGTH: 1863
<212> TYPE: DNA
<213> ORGANISM: Artificial sequence
<220> FEATURE:
<223> OTHER INFORMATION: Engineered sequence

<400> SEQUENCE: 73

| | |
| --- | --- |
| atgagcaaca ccagtttcag cgcaaaagat accgatctga gtgcactgtt tatcggtgac | 60 |
| aaagcagaaa tggtcagct gtataaggac ctgctgggca aactggttga tgaacatctg | 120 |
| ggttggcgca agaactatat gccgcaggat ccgccgatga tcagcccgga acgtcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg aatggtaac | 360 |
| aacgtggcct atgaaagcag cccggcaacc agccagatgg aagaagaagt tggtctggaa | 420 |
| tttgccaccc tgatgggcta taccaatggt tggggccata ttgttgcaga tggtagcctg | 480 |
| gcaaatctgg aaggcctgtg gtatgcacgc aatattaaga gcctgccgtt tgccatgaaa | 540 |
| gccgttgatc gaccattgt tgccggcaaa accgattggg aactgagtaa tatgagcacc | 600 |
| aaagaaatca tggacctggt tgaagccaat ggtgacaaaa ttgatgagat caaggccaaa | 660 |
| agcgcccgcg cggtaaaga tctggataaa ctgggtaaat ggctggttcc gcagaccaaa | 720 |
| cattatagtt ggctgaaagc cgcagatatt atcggcattg gcctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta caagctggt gaaagaaggt | 960 |
| atctatttct acttccacat cgacgccgcc tatggtggct atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacatacct ataacgccta tgccgcattt | 1140 |
| ccggaagccg aaagtgttac cattgatccg cataaaatgg ctatatccc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |

```
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga atttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 74
<211> LENGTH: 621
<212> TYPE: PRT
<213> ORGANISM: Artificial sequence
<220> FEATURE:
<223> OTHER INFORMATION: Engineered sequence

<400> SEQUENCE: 74

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Lys Asn Tyr Met Pro
        35                  40                  45

Gln Asp Pro Pro Met Ile Ser Pro Glu Arg Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255
```

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 75
<211> LENGTH: 1863
<212> TYPE: DNA
<213> ORGANISM: Artificial sequence
<220> FEATURE:
<223> OTHER INFORMATION: Engineered sequence

<400> SEQUENCE: 75

```
atgagcaaca ccagtttcag cgcaaaagat accgatctga gtgcactgtt tatcggtgac    60
aaagcagaaa atggtcagct gtataaggac ctgctgggca aactggttga tgaacatctg   120
ggttggcgcc agaactatat gccgcaggat ccgccgatga tcagcccgga acgtcagacc   180
agcccggact tcgtggtac cgtgaataat atgaaggacg ttctggatga gctgagcagt    240
cgcctgcgta gtcagagcgt tccgtggcat aatgccggtc gttattgggg ccacatgaat   300
agcgaaaccc tgatgccggc aattctggcc tataattatg caatgctgtg aatggtaac    360
aacgtggcct atgaaagcag cccggcaacc agccagatgg aagaagaagt tggtctggaa   420
tttgccaccc tgatgggcta ccaatggt tggggccata ttgttgcaga tggtagcctg     480
gcaaatctgg aaggcctgtg gtatgcacgc aatattaaga gcctgccgtt tgccatgaaa   540
gccgttgatc cgaccattgt tgccggcaaa accgattggg aactgagtaa tatgagcacc   600
aaagaaatca tggacctggt tgaagccaat ggtgacaaaa ttgatgagat caaggccaaa   660
agcgcccgcg gcggtaaaga tctggataaa ctgggtaaat ggctggttcc gcagaccaaa   720
cattatagtt ggctgaaagc cgcagatatt atcggcattg gcctggatca ggttattccg   780
gttccggttg atagcaatta tcgtatggat atcaacgagc tggagaaaat tatccgcgaa   840
ctggcaagta ccgaaacccc gattctgggc gttgtgggcg ttgtgggtag taccgaagaa   900
ggtgccgttg atggcattaa tgaaattgca gaactgcgta caagctggt gaaagaaggt    960
atctatttct acttccacat cgacgccgcc tatggtggct atggtcgcgc aattctgctg  1020
gatgaagata taagctgat cccgtataag gaccttcaga gtaaattcgc cgaatataac    1080
gtgttcaccg aagaagaaaa cctggtgagt gaacatacct ataacgccta tgccgcattt  1140
ccggaagccg aaagtgttac cattgatccg cataaaatgg ctatatccc gtatagtgca   1200
ggcggcattg ccattcagga tattcgcatg cgtgatgtta tcagctattt cgcaacctat  1260
gtgttcgaaa agggcgcaga tattccggca ctgctgggtg cttatattct ggaaggcagt  1320
aaagcaggcg caaccgcagc cagtgtttgg gcagcacata aaaccctgcc gctgaatgtt  1380
accggttatg gtaaactggt tggtgcaagc attgaaggcg cccgccgttt ttataatttt  1440
ctgagcggcc tggaattcaa ggtgggcgat aaaaccattg aagttcatcc gctgaccgat  1500
ccggatttta atatggttga ttacgtgttc caggagaagg gcaataataa tctggtggaa  1560
atgaacgagc tgaaccatga atttacaac caggcaagct acgttaccgg tagcatctat   1620
ggcaatgaat atctgaccag ccataccgat ttcgcaattc cggattatgg taatagcccg  1680
tttaagtttg tgaacaacct gggcgtgacc gaagaaggct ggaaagaagc aggtaaagtg  1740
accgttctgc gcgccgctgt gatgacacct tatatgaata aggcagagaa cttcgactac  1800
ttcgccccga aaattaagca ggccatgcag gaaaaactgg aagccatcta tgaagatcgt  1860
aag                                                               1863
```

<210> SEQ ID NO 76
<211> LENGTH: 621
<212> TYPE: PRT
<213> ORGANISM: Artificial sequence
<220> FEATURE:
<223> OTHER INFORMATION: Engineered sequence

<400> SEQUENCE: 76

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30
```

```
Gly Lys Leu Val Asp Glu His Leu Gly Trp Arg Gln Asn Tyr Met Pro
         35                  40                  45

Gln Asp Pro Pro Met Ile Ser Pro Glu Arg Gln Thr Ser Pro Asp Phe
 50                  55                  60

Arg Gly Thr Val Asn Asn Met Lys Asp Val Leu Asp Glu Leu Ser Ser
 65                  70                  75                  80

Arg Leu Arg Ser Gln Ser Val Pro Trp His Asn Ala Gly Arg Tyr Trp
                 85                  90                  95

Gly His Met Asn Ser Glu Thr Leu Met Pro Ala Ile Leu Ala Tyr Asn
                100                 105                 110

Tyr Ala Met Leu Trp Asn Gly Asn Val Ala Tyr Glu Ser Ser Pro
             115                 120                 125

Ala Thr Ser Gln Met Glu Glu Val Gly Leu Glu Phe Ala Thr Leu
130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
                195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445
```

| | | | | | | | | | | | | | | |
|---|---|---|---|---|---|---|---|---|---|---|---|---|---|---|
|Val|Trp|Ala|Ala|His|Lys|Thr|Leu|Pro|Leu|Asn|Val|Thr|Gly|Tyr|Gly|
| |450| | | |455| | | |460| | | | | |

Lys Leu Val Gly Ala Ser Ile Glu Gly Ala Arg Arg Phe Tyr Asn Phe
465             470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Tyr Gly Asn Ser Pro
545             550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
            610                 615                 620

```
<210> SEQ ID NO 77
<211> LENGTH: 1863
<212> TYPE: DNA
<213> ORGANISM: Artificial sequence
<220> FEATURE:
<223> OTHER INFORMATION: Engineered sequence

<400> SEQUENCE: 77
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaactatat gccgcaggat ccgccgatga tcagcgcgga acgtcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctggtaaat ggctggttcc gcagaccaaa     720
cattatagtt ggctgaaagc cgcagatatt atcggcattg gctggatca ggttattccg     780 gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta acaagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
```

```
gtgttcaccg aagaagaaaa cctggtgagt gaacatacct ataacgccta tgccgcattt   1140
ccggaagccg aaagtgttac cattgatccg cataaaatgg ctatatccc gtatagtgca    1200 ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacatc gtaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                1863
```

<210> SEQ ID NO 78
<211> LENGTH: 621
<212> TYPE: PRT
<213> ORGANISM: Artificial sequence
<220> FEATURE:
<223> OTHER INFORMATION: Engineered sequence

<400> SEQUENCE: 78

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Arg Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220
```

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
            245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
                275                 280                 285

Leu Gly Val Val Gly Val Val Gly Ser Thr Glu Glu Gly Ala Val Asp
        290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                    325                 330                 335

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
            435                 440                 445

Val Trp Ala Ala His Arg Thr Leu Pro Leu Asn Val Thr Gly Tyr Gly
        450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
610                 615                 620

<210> SEQ ID NO 79
<211> LENGTH: 1863

<212> TYPE: DNA
<213> ORGANISM: Artificial sequence
<220> FEATURE:
<223> OTHER INFORMATION: Engineered sequence

<400> SEQUENCE: 79

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaactatat gccgcaggat ccgccgatga tcagcccgga acgtcagacc     180
agcccggact tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta caatggt tggggccata ttgttgcaga tggtagcctg       480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacatc gtaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                 1863
```

<210> SEQ ID NO 80
<211> LENGTH: 621
<212> TYPE: PRT
<213> ORGANISM: Artificial sequence
<220> FEATURE:
<223> OTHER INFORMATION: Engineered sequence

```
<400> SEQUENCE: 80

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Pro Glu Arg Gln Thr Ser Pro Asp Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415
```

```
Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Arg Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
    610                 615                 620

<210> SEQ ID NO 81
<211> LENGTH: 1863
<212> TYPE: DNA
<213> ORGANISM: Artificial sequence
<220> FEATURE:
<223> OTHER INFORMATION: Engineered sequence

<400> SEQUENCE: 81
atgagcaaca ccagtttcag cgcaaaagat acctatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg cctggatca ggttattccg      780 gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
```

```
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatcccg tatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 82
<211> LENGTH: 621
<212> TYPE: PRT
<213> ORGANISM: Artificial sequence
<220> FEATURE:
<223> OTHER INFORMATION: Engineered sequence

<400> SEQUENCE: 82

```
Met Ser Asn Thr Ser Phe Ser Ala Lys Asp Thr Tyr Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
```

```
            180                 185                 190
Trp Glu Leu Ser Asn Met Ser Thr Lys Glu Ile Met Asp Leu Val Glu
        195                 200                 205
Ala Asn Gly Asp Lys Ile Asp Glu Ile Lys Ala Lys Ser Ala Arg Gly
        210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
            260                 265                 270
Glu Leu Glu Lys Ile Ile Arg Glu Leu Ala Ser Thr Glu Thr Pro Ile
        275                 280                 285
Leu Gly Val Val Gly Val Gly Ser Thr Glu Glu Gly Ala Val Asp
        290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
        355                 360                 365
Val Ser Glu His Thr Tyr Asn Ala Tyr Ala Ala Phe Pro Glu Ala Glu
        370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
        435                 440                 445
Val Trp Ala Ala His Lys Thr Leu Pro Leu Asn Val Thr Gly Tyr Gly
        450                 455                 460
Lys Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Asn Leu Val Glu Met Asn Glu Leu Asn His Glu Phe
        515                 520                 525
Tyr Asn Gln Ala Ser Tyr Val Thr Gly Ser Ile Tyr Gly Asn Glu Tyr
        530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Glu Gly Trp Lys Glu
                565                 570                 575
Ala Gly Lys Val Thr Val Leu Arg Ala Ala Val Met Thr Pro Tyr Met
            580                 585                 590
Asn Lys Ala Glu Asn Phe Asp Tyr Phe Ala Pro Lys Ile Lys Gln Ala
        595                 600                 605
```

```
Met Gln Glu Lys Leu Glu Ala Ile Tyr Glu Asp Arg Lys
    610                 615                 620
```

<210> SEQ ID NO 83
<211> LENGTH: 1863
<212> TYPE: DNA
<213> ORGANISM: Artificial sequence
<220> FEATURE:
<223> OTHER INFORMATION: Engineered sequence

<400> SEQUENCE: 83

| | | | | | |
|---|---|---|---|---|---|
| atgagcaaca | ccagtttcag | cgcaaaagat | accactctga | gtgcactgtt | tatcggtgac | 60 |
| aaagcagaaa | atggtcagct | gtataaggac | ctgctgggca | aactggttga | tgaacatctg | 120 |
| ggttggcgcc | agaattatat | gccgcaggat | ccgccgatga | tcagcgccga | acagcagacc | 180 |
| agcccggaat | tcgtggtac | cgtgaataat | atgaaggacg | ttctggatga | gctgagcagt | 240 |
| cgcctgcgta | gtcagagcgt | tccgtggcat | aatgccggtc | gttattgggg | ccacatgaat | 300 |
| agcgaaaccc | tgatgccggc | aattctggcc | tataattatg | caatgctgtg | gaatggtaac | 360 |
| aacgtggcct | atgaaagcag | cccggcaacc | agccagatgg | aagaagaagt | tggtctggaa | 420 |
| tttgccaccc | tgatgggcta | taccaatggt | tggggccata | ttgttgcaga | tggtagcctg | 480 |
| gcaaatctgg | aaggcctgtg | gtatgcacgc | aatattaaga | gcctgccgtt | gccatgaaa | 540 |
| gccgttgatc | cgaccattgt | tgccggcaaa | accgattggg | aactgagtaa | tatgagcacc | 600 |
| aaagaaatca | tggacctggt | tgaagccaat | ggtgacaaaa | ttgatgagat | caaggccaaa | 660 |
| agcgcccgcg | gcgtaaaga | tctggataaa | ctgggtaaat | ggctggttcc | gcagaccaaa | 720 |
| cattatagtt | ggctgaaagc | cgcagatatt | atcggcattg | gcctggatca | ggttattccg | 780 |
| gttccggttg | atagcaatta | tcgtatggat | atcaacgagc | tggagaaaat | tatccgcgaa | 840 |
| ctggcaagta | ccgaaaacccc | gattctgggc | gttgtgggcg | ttgtgggtag | taccgaagaa | 900 |
| ggtgccgttg | atggcattaa | tgaaattgca | gaactgcgta | acaagctggt | gaaagaaggt | 960 |
| atctatttct | acttccacat | cgacgccgcc | tatggtggct | atggtcgcgc | aattctgctg | 1020 |
| gatgaagata | taagctgat | cccgtataag | gaccttcaga | gtaaattcgc | cgaatataac | 1080 |
| gtgttcaccg | aagaagaaaa | cctggtgagt | gaacataccct | ataacgccta | tgccgcattt | 1140 |
| ccggaagccg | aaagtgttac | cattgatccg | cataaaatgg | gctatatccc | gtatagtgca | 1200 |
| ggcggcattg | ccattcagga | tattcgcatg | cgtgatgtta | tcagctattt | cgcaacctat | 1260 |
| gtgttcgaaa | agggcgcaga | tattccggca | ctgctgggtg | cttatattct | ggaaggcagt | 1320 |
| aaagcaggcg | caaccgcagc | cagtgtttgg | gcagcacata | aaaccctgcc | gctgaatgtt | 1380 |
| accggttatg | gtaaactggt | tggtgcaagc | attgaaggcg | cccgccgttt | ttataatttt | 1440 |
| ctgagcggcc | tggaattcaa | ggtgggcgat | aaaaccattg | aagttcatcc | gctgaccgat | 1500 |
| ccggatttta | atatggttga | ttacgtgttc | caggagaagg | gcaataataa | tctggtggaa | 1560 |
| atgaacgagc | tgaaccatga | attttacaac | caggcaagct | acgttaccgg | tagcatctat | 1620 |
| ggcaatgaat | atctgaccag | ccataccgat | ttcgcaattc | cggattatgg | taatagcccg | 1680 |
| tttaagtttg | tgaacaacct | gggcgtgacc | gaagaaggcg | ggaaagaagc | aggtaaagtg | 1740 |
| accgttctgc | gcgccgctgt | gatgacacct | tatatgaata | aggcagagaa | cttcgactac | 1800 |
| ttcgccccga | aaattaagca | ggccatgcag | gaaaaactgg | aagccatcta | tgaagatcgt | 1860 |
| aag | | | | | | 1863 |

```
<210> SEQ ID NO 84
<211> LENGTH: 621
<212> TYPE: PRT
<213> ORGANISM: Artificial sequence
<220> FEATURE:
<223> OTHER INFORMATION: Engineered sequence

<400> SEQUENCE: 84

Met Ser Asn Thr Ser Phe Ser Ala Lys Asp Thr Thr Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
```

```
                 370                 375                 380
Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
    610                 615                 620

<210> SEQ ID NO 85
<211> LENGTH: 1863
<212> TYPE: DNA
<213> ORGANISM: Artificial sequence
<220> FEATURE:
<223> OTHER INFORMATION: Engineered sequence

<400> SEQUENCE: 85
atgagcaaca ccagtttcag cgcaaaagat accgatctga gtgcactgtt tatcggtgac      60
aaagcagaaa atggtacgct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tgggccata ttgttgcaga tggtagcctg      480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
```

```
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta caagctggt gaaagaaggt    960 atctatttct acttccacat cgacgccgcc tatggtggct atggtcgcgc aattctgctg    1020
gatgaagata ataagctgat cccgtataag gaccttcaga gtaaattcgc cgaatataac    1080
gtgttcaccg aagaagaaaa cctggtgagt gaacatacct ataacgccta tgccgcattt    1140
ccggaagccg aaagtgttac cattgatccg cataaaatgg gctatatccc gtatagtgca    1200
ggcggcattg ccattcagga tattcgcatg cgtgatgtta tcagctattt cgcaaccctat    1260 gtgttcgaaa agggcgcaga tattccggca ctgctgggtg cttatattct ggaaggcagt    1320
aaagcaggcg caaccgcagc cagtgtttgg gcagcacata aaccctgcc gctgaatgtt    1380 accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta tatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                   1863
```

<210> SEQ ID NO 86
<211> LENGTH: 621
<212> TYPE: PRT
<213> ORGANISM: Artificial sequence
<220> FEATURE:
<223> OTHER INFORMATION: Engineered sequence

<400> SEQUENCE: 86

```
Met Ser Asn Thr Ser Phe Ser Ala Lys Asp Thr Asp Leu Ser Ala Leu
1               5                   10                  15

Phe Ile Gly Asp Lys Ala Glu Asn Gly Thr Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140
```

```
Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
            165                 170                 175

Phe Ala Met Lys Ala Val Asp Pro Thr Ile Val Ala Gly Lys Thr Asp
        180                 185                 190

Trp Glu Leu Ser Asn Met Ser Thr Lys Glu Ile Met Asp Leu Val Glu
    195                 200                 205

Ala Asn Gly Asp Lys Ile Asp Glu Ile Lys Ala Lys Ser Ala Arg Gly
210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
            245                 250                 255

Gln Val Ile Pro Val Pro Val Asp Ser Asn Tyr Arg Met Asp Ile Asn
        260                 265                 270

Glu Leu Glu Lys Ile Ile Arg Glu Leu Ala Ser Thr Glu Thr Pro Ile
    275                 280                 285

Leu Gly Val Val Gly Val Gly Ser Thr Glu Glu Gly Ala Val Asp
290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
            325                 330                 335

Ala Ile Leu Leu Asp Glu Asp Asn Lys Leu Ile Pro Tyr Lys Asp Leu
        340                 345                 350

Gln Ser Lys Phe Ala Glu Tyr Asn Val Phe Thr Glu Glu Asn Leu
    355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
        420                 425                 430

Gly Ala Tyr Ile Leu Glu Gly Ser Lys Ala Gly Ala Thr Ala Ala Ser
    435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
            485                 490                 495

Pro Leu Thr Asp Pro Asp Phe Asn Met Val Asp Tyr Val Phe Gln Glu
        500                 505                 510

Lys Gly Asn Asn Asn Leu Val Glu Met Asn Glu Leu Asn His Glu Phe
    515                 520                 525

Tyr Asn Gln Ala Ser Tyr Val Thr Gly Ser Ile Tyr Gly Asn Glu Tyr
530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
```

| | | 565 | | | | 570 | | | | 575 | |
|---|---|---|---|---|---|---|---|---|---|---|---|
Ala Gly Lys Val Thr Val Leu Arg Ala Ala Val Met Thr Pro Tyr Met
                580                    585                   590

Asn Lys Ala Glu Asn Phe Asp Tyr Phe Ala Pro Lys Ile Lys Gln Ala
    595                    600                   605

Met Gln Glu Lys Leu Glu Ala Ile Tyr Glu Asp Arg Lys
    610                    615                   620

<210> SEQ ID NO 87
<211> LENGTH: 1863
<212> TYPE: DNA
<213> ORGANISM: Artificial sequence
<220> FEATURE:
<223> OTHER INFORMATION: Engineered sequence

<400> SEQUENCE: 87

```
atgagcaaca ccagtttcag cgcaaaagat accgatctga gtgcactgtt tatcggtgac      60
aaagcagaaa atggttttct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg cctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta acaagctggt gaaagaaggt     960
atctatttct acttccacat cgacgccgcc tatggtggct atggtcgcgc aattctgctg    1020
gatgaagata taagctgat cccgtataag gaccttcaga gtaaattcgc gaatataac     1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta tatggttga ttacgtgttc caggagaagg caataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaagaagc aggtaaagtg    1740
```

```
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 88
<211> LENGTH: 621
<212> TYPE: PRT
<213> ORGANISM: Artificial sequence
<220> FEATURE:
<223> OTHER INFORMATION: Engineered sequence

<400> SEQUENCE: 88

```
Met Ser Asn Thr Ser Phe Ser Ala Lys Asp Thr Asp Leu Ser Ala Leu
1               5                   10                  15

Phe Ile Gly Asp Lys Ala Glu Asn Gly Phe Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335
```

Ala Ile Leu Leu Asp Glu Asp Asn Lys Leu Ile Pro Tyr Lys Asp Leu
                340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
                420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
        450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 89
<211> LENGTH: 1863
<212> TYPE: DNA
<213> ORGANISM: Artificial sequence
<220> FEATURE:
<223> OTHER INFORMATION: Engineered sequence

<400> SEQUENCE: 89
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgca ttaattatat gccgcaggat ccgccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480

```
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg gcctggatca ggttattccg    780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg gctatatccc gtatagtgca   1200
ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgttttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                1863
```

<210> SEQ ID NO 90
<211> LENGTH: 621
<212> TYPE: PRT
<213> ORGANISM: Artificial sequence
<220> FEATURE:
<223> OTHER INFORMATION: Engineered sequence

<400> SEQUENCE: 90

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Ile Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

```
Tyr Ala Met Leu Trp Asn Gly Asn Asn Val Ala Tyr Glu Ser Ser Pro
            115                 120                 125
Ala Thr Ser Gln Met Glu Glu Val Gly Leu Glu Phe Ala Thr Leu
    130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
            180                 185                 190
Trp Glu Leu Ser Asn Met Ser Thr Lys Glu Ile Met Asp Leu Val Glu
            195                 200                 205
Ala Asn Gly Asp Lys Ile Asp Glu Ile Lys Ala Lys Ser Ala Arg Gly
    210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
            260                 265                 270
Glu Leu Glu Lys Ile Ile Arg Glu Leu Ala Ser Thr Glu Thr Pro Ile
            275                 280                 285
Leu Gly Val Val Gly Val Val Gly Ser Thr Glu Gly Ala Val Asp
            290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
            355                 360                 365
Val Ser Glu His Thr Tyr Asn Ala Tyr Ala Ala Phe Pro Glu Ala Glu
    370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
            435                 440                 445
Val Trp Ala Ala His Lys Thr Leu Pro Leu Asn Val Thr Gly Tyr Gly
    450                 455                 460
Lys Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
                485                 490                 495
Pro Leu Thr Asp Pro Asp Phe Asn Met Val Asp Tyr Val Phe Gln Glu
            500                 505                 510
Lys Gly Asn Asn Leu Val Glu Met Asn Glu Leu Asn His Glu Phe
            515                 520                 525
```

```
Tyr Asn Gln Ala Ser Tyr Val Thr Gly Ser Ile Tyr Gly Asn Glu Tyr
        530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
    610                 615                 620

<210> SEQ ID NO 91
<211> LENGTH: 1863
<212> TYPE: DNA
<213> ORGANISM: Artificial sequence
<220> FEATURE:
<223> OTHER INFORMATION: Engineered sequence

<400> SEQUENCE: 91
```

| | | |
|---|---|---|
| atgagcaaca ccagtttcag cgcaaaagat accgatctga gtgcactgtt tatcggtgac | 60 |
| aaagcagaaa atggtcagct gtataaggac ctgctgggca aactggttga tgaacatctg | 120 |
| ggttggcgcc tgaattatat gccgcaggat ccgccgatga tcagcgccga acagcagacc | 180 |
| agcccggaat tcgtggtac cgtgaataat atgaaggacg ttctggatga gctgagcagt | 240 |
| cgcctgcgta gtcagagcgt tccgtggcat aatgccggtc gttattgggg ccacatgaat | 300 |
| agcgaaaccc tgatgccggc aattctggcc tataattatg caatgctgtg aatggtaac | 360 |
| aacgtggcct atgaaagcag cccggcaacc agccagatgg aagaagaagt tggtctggaa | 420 |
| tttgccaccc tgatgggcta ccaatggtg tgggccata ttgttgcaga tggtagcctg | 480 |
| gcaaatctgg aaggcctgtg gtatgcacgc aatattaaga gcctgccgtt tgccatgaaa | 540 |
| gccgttgatc cgaccattgt tgccggcaaa accgattggg aactgagtaa tatgagcacc | 600 |
| aaagaaatca tggacctggt tgaagccaat ggtgacaaaa ttgatgagat caaggccaaa | 660 |
| agcgcccgcg cggtaaaga tctggataaa ctgggtaaat ggctggttcc gcagaccaaa | 720 |
| cattatagtt ggctgaaagc cgcagatatt atcggcattg cctggatca ggttattccg | 780 |
| gttccggttg atagcaatta tcgtatggat atcaacgagc tggagaaaat tatccgcgaa | 840 |
| ctggcaagta ccgaaacccc gattctgggc gttgtgggcg ttgtgggtag taccgaagaa | 900 |
| ggtgccgttg atggcattaa tgaaattgca gaactgcgta acaagctggt gaaagaaggt | 960 |
| atctatttct acttccacat cgacgccgcc tatggtggct atggtcgcgc aattctgctg | 1020 |
| gatgaagata taagctgat cccgtataag gaccttcaga gtaaattcgc cgaatataac | 1080 |
| gtgttcaccg aagaagaaaa cctggtgagt gaacatacct ataacgccta tgccgcattt | 1140 |
| ccggaagccg aaagtgttac cattgatccg cataaaatgg ctatatcc gtatagtgca | 1200 |
| ggcggcattg ccattcagga tattcgcatg cgtgatgtta tcagctattt cgcaacctat | 1260 |
| gtgttcgaaa agggcgcaga tattccggca ctgctgggtg cttatattct ggaaggcagt | 1320 |
| aaagcaggcg caaccgcagc cagtgtttgg gcagcacata aaccctgcc gctgaatgtt | 1380 |
| accggttatg gtaaactggt tggtgcaagc attgaaggcg cccgccgttt ttataatttt | 1440 |
| ctgagcggcc tggaattcaa ggtgggcgat aaaccattg aagttcatcc gctgaccgat | 1500 |
| ccggatttta atatggttga ttacgtgttc caggagaagg gcaataataa tctggtggaa | 1560 |

```
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 92
<211> LENGTH: 621
<212> TYPE: PRT
<213> ORGANISM: Artificial sequence
<220> FEATURE:
<223> OTHER INFORMATION: Engineered sequence

<400> SEQUENCE: 92

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Leu Asn Tyr Met Pro
        35                  40                  45

Gln Asp Pro Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
        275                 280                 285

Leu Gly Val Val Gly Val Val Gly Ser Thr Glu Glu Gly Ala Val Asp
    290                 295                 300
```

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
            325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
            485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
            565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
610                 615                 620

<210> SEQ ID NO 93
<211> LENGTH: 1863
<212> TYPE: DNA
<213> ORGANISM: Artificial sequence
<220> FEATURE:
<223> OTHER INFORMATION: Engineered sequence

<400> SEQUENCE: 93
atgagcaaca ccagtttcag cgcaaaagat accgatctga gtgcactgtt tatcggtgac    60
aaagcagaaa atggtcagct gtataaggac ctgctgggca aactggttga tgaacatctg   120
ggttggcgcc agaattatat gccgcaggat ccgccgatga tcagcgccga aaggcagacc   180
agcccggaat tcgtggtac cgtgaataat atgaaggacg ttctggatga gctgagcagt   240

```
cgcctgcgta gtcagagcgt tccgtggcat aatgccggtc gttattgggg ccacatgaat    300
agcgaaaccc tgatgccggc aattctggcc tataattatg caatgctgtg gaatggtaac    360
aacgtggcct atgaaagcag cccggcaacc agccagatgg aagaagaagt tggtctggaa    420
tttgccaccc tgatgggcta ccaatggt tggggccata ttgttgcaga tggtagcctg      480
gcaaatctgg aaggcctgtg gtatgcacgc aatattaaga gcctgccgtt tgccatgaaa    540
gccgttgatc cgaccattgt tgccggcaaa accgattggg aactgagtaa tatgagcacc    600
aaagaaatca tggacctggt tgaagccaat ggtgacaaaa ttgatgagat caaggccaaa    660
agcgcccgcg gcggtaaaga tctggataaa ctgggtaaat ggctggttcc gcagaccaaa    720
cattatagtt ggctgaaagc cgcagatatt atcggcattg cctggatca ggttattccg     780
gttccggttg atagcaatta tcgtatggat atcaacgagc tggagaaaat tatccgcgaa    840
ctggcaagta ccgaaacccc gattctgggc gttgtgggcg ttgtgggtag taccgaagaa    900
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata taagctgat cccgtataag gaccttcaga gtaaattcgc cgaatataac    1080
gtgttcaccg aagaagaaaa cctggtgagt gaacatacct ataacgccta tgccgcattt   1140
ccggaagccg aaagtgttac cattgatccg cataaaatgg ctatatcccc gtatagtgca   1200
ggcggcattg ccattcagga tattcgcatg cgtgatgtta tcagctattt cgcaaccctat  1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtaaactggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                  1863
```

<210> SEQ ID NO 94
<211> LENGTH: 621
<212> TYPE: PRT
<213> ORGANISM: Artificial sequence
<220> FEATURE:
<223> OTHER INFORMATION: Engineered sequence

<400> SEQUENCE: 94

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Arg Gln Thr Ser Pro Glu Phe
    50                  55                  60

Arg Gly Thr Val Asn Asn Met Lys Asp Val Leu Asp Glu Leu Ser Ser
```

-continued

```
            65                  70                  75                  80
Arg Leu Arg Ser Gln Ser Val Pro Trp His Asn Ala Gly Arg Tyr Trp
                85                  90                  95
Gly His Met Asn Ser Glu Thr Leu Met Pro Ala Ile Leu Ala Tyr Asn
               100                 105                 110
Tyr Ala Met Leu Trp Asn Gly Asn Val Ala Tyr Glu Ser Ser Pro
               115                 120                 125
Ala Thr Ser Gln Met Glu Glu Val Gly Leu Glu Phe Ala Thr Leu
   130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
               165                 170                 175
Phe Ala Met Lys Ala Val Asp Pro Thr Ile Val Ala Gly Lys Thr Asp
               180                 185                 190
Trp Glu Leu Ser Asn Met Ser Thr Lys Glu Ile Met Asp Leu Val Glu
           195                 200                 205
Ala Asn Gly Asp Lys Ile Asp Glu Ile Lys Ala Lys Ser Ala Arg Gly
   210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
               245                 250                 255
Gln Val Ile Pro Val Pro Val Asp Ser Asn Tyr Arg Met Asp Ile Asn
               260                 265                 270
Glu Leu Glu Lys Ile Ile Arg Glu Leu Ala Ser Thr Glu Thr Pro Ile
           275                 280                 285
Leu Gly Val Val Gly Val Gly Ser Thr Glu Glu Gly Ala Val Asp
   290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
               325                 330                 335
Ala Ile Leu Leu Asp Glu Asp Asn Lys Leu Ile Pro Tyr Lys Asp Leu
               340                 345                 350
Gln Ser Lys Phe Ala Glu Tyr Asn Val Phe Thr Glu Glu Asn Leu
           355                 360                 365
Val Ser Glu His Thr Tyr Asn Ala Tyr Ala Ala Phe Pro Glu Ala Glu
   370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
               405                 410                 415
Phe Ala Thr Tyr Val Phe Glu Lys Gly Ala Asp Ile Pro Ala Leu Leu
               420                 425                 430
Gly Ala Tyr Ile Leu Glu Gly Ser Lys Ala Gly Ala Thr Ala Ala Ser
           435                 440                 445
Val Trp Ala Ala His Lys Thr Leu Pro Leu Asn Val Thr Gly Tyr Gly
   450                 455                 460
Lys Leu Val Gly Ala Ser Ile Glu Gly Ala Arg Arg Phe Tyr Asn Phe
465                 470                 475                 480
Leu Ser Gly Leu Glu Phe Lys Val Gly Asp Lys Thr Ile Glu Val His
               485                 490                 495
```

```
Pro Leu Thr Asp Pro Asp Phe Asn Met Val Asp Tyr Val Phe Gln Glu
        500                 505                 510
Lys Gly Asn Asn Asn Leu Val Glu Met Asn Glu Leu Asn His Glu Phe
        515                 520                 525
Tyr Asn Gln Ala Ser Tyr Val Thr Gly Ser Ile Tyr Gly Asn Glu Tyr
        530                 535                 540
Leu Thr Ser His Thr Asp Phe Ala Ile Pro Asp Tyr Gly Asn Ser Pro
545                 550                 555                 560
Phe Lys Phe Val Asn Asn Leu Gly Val Thr Glu Gly Trp Lys Glu
                565                 570                 575
Ala Gly Lys Val Thr Val Leu Arg Ala Ala Val Met Thr Pro Tyr Met
                580                 585                 590
Asn Lys Ala Glu Asn Phe Asp Tyr Phe Ala Pro Lys Ile Lys Gln Ala
            595                 600                 605
Met Gln Glu Lys Leu Glu Ala Ile Tyr Glu Asp Arg Lys
    610                 615                 620

<210> SEQ ID NO 95
<211> LENGTH: 1863
<212> TYPE: DNA
<213> ORGANISM: Artificial sequence
<220> FEATURE:
<223> OTHER INFORMATION: Engineered sequence

<400> SEQUENCE: 95
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga agttcagacc     180
agcccggaat tcgtggtgta cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggcta taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcgttaaaga tctggataaa ctgggtaaat ggctggttcc gcagaccaaa     720
cattatagtt ggctgaaagc cgcagatatt atcggcattg cctggatcag gttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc gaatataac    1080
gtgttcaccg aagaagaaaa cctggtgagt gaacatacct ataacgccta tgccgcattt    1140
ccggaagccg aaagtgttac cattgatccg cataaaatgg ctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
```

-continued

```
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 96
<211> LENGTH: 621
<212> TYPE: PRT
<213> ORGANISM: Artificial sequence
<220> FEATURE:
<223> OTHER INFORMATION: Engineered sequence

<400> SEQUENCE: 96

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Val Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
                245                 250                 255

Gln Val Ile Pro Val Pro Val Asp Ser Asn Tyr Arg Met Asp Ile Asn
```

```
        260                 265                 270
Glu Leu Glu Lys Ile Ile Arg Glu Leu Ala Ser Thr Glu Thr Pro Ile
            275                 280                 285

Leu Gly Val Val Gly Val Val Gly Ser Thr Glu Gly Ala Val Asp
        290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
            370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
610                 615                 620

<210> SEQ ID NO 97
<211> LENGTH: 1863
<212> TYPE: DNA
<213> ORGANISM: Artificial sequence
<220> FEATURE:
<223> OTHER INFORMATION: Engineered sequence

<400> SEQUENCE: 97
atgagcaaca ccagtttcag cgcaaaagat accgatctga gtgcactgtt tatcggtgac     60
```

-continued

```
aaagcagaaa atggtcagct gtataaggac ctgctgggca aactggttga tgaacatctg      120
ggttggcgcc agaattatat gccgcaggat ccgccgatga tcagcgccga acatcagacc      180
agcccggaat tcgtggtac cgtgaataat atgaaggacg ttctggatga gctgagcagt       240
cgcctgcgta gtcagagcgt tccgtggcat aatgccggtc gttattgggg ccacatgaat      300
agcgaaaccc tgatgccggc aattctggcc tataattatg caatgctgtg aatggtaac      360 aacgtggcct atgaaagcag cccggcaacc agccagatgg aagaagaagt tggtctggaa      420
tttgccaccc tgatgggcta caccaatggt tggggccata tgttgcaga tggtagcctg      480 gcaaatctgg aaggcctgtg gtatgcacgc aatattaaga gcctgccgtt tgccatgaaa      540
gccgttgatc cgaccattgt tgccggcaaa accgattggg aactgagtaa tatgagcacc      600
aaagaaatca tggacctggt tgaagccaat ggtgacaaaa ttgatgagat caaggccaaa      660
agcgcccgcg gcggtaaaga tctggataaa ctgggtaaat ggctggttcc gcagaccaaa      720
cattatagtt ggctgaaagc cgcagatatt atcggcattg cctggatca ggttattccg       780 gttccggttg atagcaatta tcgtatggat atcaacgagc tggagaaaat tatccgcgaa      840
ctggcaagta ccgaaacccc gattctgggc gttgtgggcg ttgtgggtag taccgaagaa      900
ggtgccgttg atggcattaa tgaaattgca gaactgcgta caagctggt gaagaaggt       960 atctatttct acttccacat cgacgccgcc tatggtggct atggtcgcgc aattctgctg     1020
gatgaagata ataagctgat cccgtataag gaccttcaga gtaaattcgc cgaatataac     1080
gtgttcaccg aagaagaaaa cctggtgagt gaacatacct ataacgccta tgccgcattt     1140
ccggaagccg aaagtgttac cattgatccg cataaaatgg ctatatccc gtatagtgca      1200 ggcggcattg ccattcagga tattcgcatg cgtgatgtta tcagctattt cgcaacctat     1260
gtgttcgaaa agggcgcaga tattccggca ctgctgggtg cttatattct ggaaggcagt     1320
aaagcaggcg caaccgcagc cagtgtttgg gcagcacata aaccctgcc gctgaatgtt      1380 accggttatg gtaaactggt tggtgcaagc attgaaggcg cccgccgttt ttataatttt     1440
ctgagcggcc tggaattcaa ggtgggcgat aaaaccattg aagttcatcc gctgaccgat     1500 ccggattta atatggttga ttacgtgttc caggagaagg gcaataataa tctggtggaa      1560
atgaacgagc tgaaccatga attttacaac caggcaagct acgttaccgg tagcatctat     1620
ggcaatgaat atctgaccag ccataccgat ttcgcaattc cggattatgg taatagcccg     1680
tttaagtttg tgaacaacct gggcgtgacc gaagaaggct ggaaagaagc aggtaaagtg     1740
accgttctgc gcgccgctgt gatgacacct tatatgaata aggcagagaa cttcgactac     1800
ttcgccccga aaattaagca ggccatgcag gaaaaactgg aagccatcta tgaagatcgt     1860
aag                                                                   1863
```

<210> SEQ ID NO 98
<211> LENGTH: 621
<212> TYPE: PRT
<213> ORGANISM: Artificial sequence
<220> FEATURE:
<223> OTHER INFORMATION: Engineered sequence

<400> SEQUENCE: 98

Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

-continued

```
Gly Lys Leu Val Asp Glu His Leu Gly Trp Arg Gln Asn Tyr Met Pro
             35                  40                  45
Gln Asp Pro Pro Met Ile Ser Ala Glu His Gln Thr Ser Pro Glu Phe
 50                  55                  60
Arg Gly Thr Val Asn Asn Met Lys Asp Val Leu Asp Glu Leu Ser Ser
 65                  70                  75                  80
Arg Leu Arg Ser Gln Ser Val Pro Trp His Asn Ala Gly Arg Tyr Trp
                 85                  90                  95
Gly His Met Asn Ser Glu Thr Leu Met Pro Ala Ile Leu Ala Tyr Asn
            100                 105                 110
Tyr Ala Met Leu Trp Asn Gly Asn Asn Val Ala Tyr Glu Ser Ser Pro
            115                 120                 125
Ala Thr Ser Gln Met Glu Glu Glu Val Gly Leu Glu Phe Ala Thr Leu
130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
            180                 185                 190
Trp Glu Leu Ser Asn Met Ser Thr Lys Glu Ile Met Asp Leu Val Glu
            195                 200                 205
Ala Asn Gly Asp Lys Ile Asp Glu Ile Lys Ala Lys Ser Ala Arg Gly
210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
            260                 265                 270
Glu Leu Glu Lys Ile Ile Arg Glu Leu Ala Ser Thr Glu Thr Pro Ile
            275                 280                 285
Leu Gly Val Val Gly Val Val Gly Ser Thr Glu Glu Gly Ala Val Asp
290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
            355                 360                 365
Val Ser Glu His Thr Tyr Asn Ala Tyr Ala Ala Phe Pro Glu Ala Glu
370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
Phe Ala Thr Tyr Val Phe Glu Lys Gly Ala Asp Ile Pro Ala Leu Leu
            420                 425                 430
Gly Ala Tyr Ile Leu Glu Gly Ser Lys Ala Gly Ala Thr Ala Ala Ser
            435                 440                 445
Val Trp Ala Ala His Lys Thr Leu Pro Leu Asn Val Thr Gly Tyr Gly
```

```
                450             455             460
Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
                500                 505                 510

Lys Gly Asn Asn Asn Leu Val Glu Met Asn Glu Leu Asn His Glu Phe
                515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
                580                 585                 590

Asn Lys Ala Glu Asn Phe Asp Tyr Phe Ala Pro Lys Ile Lys Gln Ala
            595                 600                 605

Met Gln Glu Lys Leu Glu Ala Ile Tyr Glu Asp Arg Lys
        610                 615                 620
```

<210> SEQ ID NO 99
<211> LENGTH: 1863
<212> TYPE: DNA
<213> ORGANISM: Artificial sequence
<220> FEATURE:
<223> OTHER INFORMATION: Engineered sequence

<400> SEQUENCE: 99

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt     240
cgcctgcgta gtcagagcgt tccgtggcat aatgccggtc gttattgggg ccacatgaat     300
agcgaaaccc tgatgccggc aattctggcc tataattatg caatgctgtg gaatggtaac     360
aacgtggcct atgaaagcag cccggcaacc agccagatgg aagaagaagt tggtctggaa     420
tttgccaccc tgatgggctt taccaatggt tggggccata ttgttgcaga tggtagcctg     480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg cggtaaaga tctggataaa ctgggtaaat ggctggttcc gcagaccaaa     720
cattatagtt ggctgaaagc cgcagatatt atcggcattg cctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta caagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac    1080
gtgttcaccg aagaagaaaa cctggtgagt gaacataccct ataacgccta tgccgcattt    1140
```

```
ccggaagccg aaagtgttac cattgatccg cataaaatgg gctatatccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtaaactggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga attttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 100
<211> LENGTH: 621
<212> TYPE: PRT
<213> ORGANISM: Artificial sequence
<220> FEATURE:
<223> OTHER INFORMATION: Engineered sequence

<400> SEQUENCE: 100

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Phe Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190

Trp Glu Leu Ser Asn Met Ser Thr Lys Glu Ile Met Asp Leu Val Glu
        195                 200                 205

Ala Asn Gly Asp Lys Ile Asp Glu Ile Lys Ala Lys Ser Ala Arg Gly
    210                 215                 220
```

-continued

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
            245                 250                 255

Gln Val Ile Pro Val Pro Val Asp Ser Asn Tyr Arg Met Asp Ile Asn
        260                 265                 270

Glu Leu Glu Lys Ile Ile Arg Glu Leu Ala Ser Thr Glu Thr Pro Ile
    275                 280                 285

Leu Gly Val Val Gly Val Val Gly Ser Thr Glu Glu Gly Ala Val Asp
    290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
                325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
        355                 360                 365

Val Ser Glu His Thr Tyr Asn Ala Tyr Ala Ala Phe Pro Glu Ala Glu
    370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
                405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
        435                 440                 445

Val Trp Ala Ala His Lys Thr Leu Pro Leu Asn Val Thr Gly Tyr Gly
    450                 455                 460

Lys Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 101
<211> LENGTH: 1863
<212> TYPE: DNA

<213> ORGANISM: Artificial sequence
<220> FEATURE:
<223> OTHER INFORMATION: Engineered sequence

<400> SEQUENCE: 101

```
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg aatggtaac     360
aacgtggcct atgaaagcag cccggcaacc agccagatgg aagaagaagt tggtctggaa     420
tttgccaccc tgatgggcta taccaatggt tgggccata ttgttgcaga tggtagcctg      480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggacctggt tgaagccaat ggtgacaaaa ttgatgagat caaggccaaa     660
agcgcccgcg gcggtaaaga tctggataaa ctgggtaaat ggctggttcc gcagaccaaa     720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900
ggtgccgttg atggcattaa tgaaattgca gaactgcgta acaagctggt gaaagaaggt     960
atctatttct acttccacat cgacgccgcc tatggtggct atggtcgcgc aattctgctg    1020
gatgaagata taagctgat cccgtataag gaccttcaga gtaaattcgc cgaatataac     1080
gtgttcaccg aagaagaaaa cctggtgagt gaacatacct ataacgccta tgccgcattt    1140
ccggaagccc aaagtgttac cattgatccg cataaaatgg ctatatcccc gtatagtgca    1200
ggcggcattg ccattcagga tattcgcatg cgtgatgtta tcagctattt cgcaacctat    1260
gtgttcgaaa agggcgcaga tattccggca ctgctgggtg cttatattct ggaaggcagt    1320
aaagcaggcg caaccgcagc cagtgtttgg gcagcacata aaaccctgcc gctgaatgtt    1380
accggttatg gtttgctggt tggtgcaagc attgaaggcg cccgccgttt ttataatttt    1440
ctgagcggcc tggaattcaa ggtgggcgat aaaaccattg aagttcatcc gctgaccgat    1500
ccggatttta atatggttga ttacgtgttc caggagaagg gcaataataa tctggtggaa    1560
atgaacgagc tgaaccatga atttttacaac caggcaagct acgttaccgg tagcatctat    1620
ggcaatgaat atctgaccag ccataccgat ttcgcaattc cggattatgg taatagcccg    1680
tttaagtttg tgaacaacct gggcgtgacc gaagaaggct ggaaagaagc aggtaaagtg    1740
accgttctgc gcgccgctgt gatgacacct tatatgaata aggcagagaa cttcgactac    1800
ttcgccccga aaattaagca ggccatgcag gaaaaactgg aagccatcta tgaagatcgt    1860
aag                                                                  1863
```

<210> SEQ ID NO 102
<211> LENGTH: 621
<212> TYPE: PRT
<213> ORGANISM: Artificial sequence
<220> FEATURE:
<223> OTHER INFORMATION: Engineered sequence

<400> SEQUENCE: 102

```
Met Ser Asn Thr Ser Phe Ser Ala Lys Asp Thr Asp Leu Ser Ala Leu
1               5                   10                  15
Phe Ile Gly Asp Lys Ala Glu Asn Gly Gln Leu Tyr Lys Asp Leu Leu
            20                  25                  30
Gly Lys Leu Val Asp Glu His Leu Gly Trp Arg Gln Asn Tyr Met Pro
        35                  40                  45
Gln Asp Pro Pro Met Ile Ser Ala Glu Gln Thr Ser Pro Glu Phe
50                  55                  60
Arg Gly Thr Val Asn Asn Met Lys Asp Val Leu Asp Glu Leu Ser Ser
65                  70                  75                  80
Arg Leu Arg Ser Gln Ser Val Pro Trp His Asn Ala Gly Arg Tyr Trp
                85                  90                  95
Gly His Met Asn Ser Glu Thr Leu Met Pro Ala Ile Leu Ala Tyr Asn
            100                 105                 110
Tyr Ala Met Leu Trp Asn Gly Asn Asn Val Ala Tyr Glu Ser Ser Pro
        115                 120                 125
Ala Thr Ser Gln Met Glu Glu Val Gly Leu Glu Phe Ala Thr Leu
130                 135                 140
Met Gly Tyr Thr Asn Gly Trp Gly His Ile Val Ala Asp Gly Ser Leu
145                 150                 155                 160
Ala Asn Leu Glu Gly Leu Trp Tyr Ala Arg Asn Ile Lys Ser Leu Pro
                165                 170                 175
Phe Ala Met Lys Ala Val Asp Pro Thr Ile Val Ala Gly Lys Thr Asp
            180                 185                 190
Trp Glu Leu Ser Asn Met Ser Thr Lys Glu Ile Met Asp Leu Val Glu
        195                 200                 205
Ala Asn Gly Asp Lys Ile Asp Glu Ile Lys Ala Lys Ser Ala Arg Gly
210                 215                 220
Gly Lys Asp Leu Asp Lys Leu Gly Lys Trp Leu Val Pro Gln Thr Lys
225                 230                 235                 240
His Tyr Ser Trp Leu Lys Ala Ala Asp Ile Ile Gly Ile Gly Leu Asp
                245                 250                 255
Gln Val Ile Pro Val Pro Val Asp Ser Asn Tyr Arg Met Asp Ile Asn
            260                 265                 270
Glu Leu Glu Lys Ile Ile Arg Glu Leu Ala Ser Thr Glu Thr Pro Ile
        275                 280                 285
Leu Gly Val Val Gly Val Val Gly Ser Thr Glu Glu Gly Ala Val Asp
290                 295                 300
Gly Ile Asn Glu Ile Ala Glu Leu Arg Asn Lys Leu Val Lys Glu Gly
305                 310                 315                 320
Ile Tyr Phe Tyr Phe His Ile Asp Ala Ala Tyr Gly Gly Tyr Gly Arg
                325                 330                 335
Ala Ile Leu Leu Asp Glu Asp Asn Lys Leu Ile Pro Tyr Lys Asp Leu
            340                 345                 350
Gln Ser Lys Phe Ala Glu Tyr Asn Val Phe Thr Glu Glu Asn Leu
        355                 360                 365
Val Ser Glu His Thr Tyr Asn Ala Tyr Ala Phe Pro Glu Ala Glu
370                 375                 380
Ser Val Thr Ile Asp Pro His Lys Met Gly Tyr Ile Pro Tyr Ser Ala
385                 390                 395                 400
Gly Gly Ile Ala Ile Gln Asp Ile Arg Met Arg Asp Val Ile Ser Tyr
                405                 410                 415
```

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Thr Ala Ala Ser
        435                 440                 445

Val Trp Ala Ala His Lys Thr Leu Pro Leu Asn Val Thr Gly Tyr Gly
    450                 455                 460

Leu Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
                485                 490                 495

Pro Leu Thr Asp Pro Asp Phe Asn Met Val Asp Tyr Val Phe Gln Glu
            500                 505                 510

Lys Gly Asn Asn Asn Leu Val Glu Met Asn Glu Leu Asn His Glu Phe
        515                 520                 525

Tyr Asn Gln Ala Ser Tyr Val Thr Gly Ser Ile Tyr Gly Asn Glu Tyr
    530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
                565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
        595                 600                 605

Met Gln Glu Lys Leu Glu Ala Ile Tyr Glu Asp Arg Lys
    610                 615                 620

<210> SEQ ID NO 103
<211> LENGTH: 1863
<212> TYPE: DNA
<213> ORGANISM: Artificial sequence
<220> FEATURE:
<223> OTHER INFORMATION: Engineered sequence

<400> SEQUENCE: 103
atgagcaaca ccagtttcag cgcaaaagat accgatctga gtgcactgtt tatcggtgac      60
aaagcagaaa atggtcagct gtataaggac ctgctgggca aactggttga tgaacatctg     120
ggttggcgcc agaattatat gccgcaggat ccgccgatga tcagcgccga acagcagacc     180
agcccggaat tcgtggtac cgtgaataat atgaaggacg ttctggatga gctgagcagt      240
cgcctgcgta gtcagagcgt tccgtggcat aatgccggtc gttattgggg ccacatgaat     300
agcgaaaccc tgatgccggc aattctggcc tataattatg caatgctgtg aatggtaac     360 aacgtggcct atgaaagcag cccggcaacc agccagatgg aagaagaagt tggtctggaa     420
tttgccaccc tgatgggcta caatggt tggggccata ttgttgcaga tggtagcctg        480
gcaaatctgg aaggcctgtg gtatgcacgc aatattaaga gcctgccgtt tgccatgaaa     540
gccgttgatc cgaccattgt tgccggcaaa accgattggg aactgagtaa tatgagcacc     600
aaagaaatca tggaccctggt tgaagccaat ggtgacaaaa ttgatgagat caaggccaaa    660
agcgcccgcg gcggtaaaga tctgataaa ctgggtaaat ggctggttcc gcagaccaaa      720
cattatagtt ggctgaaagc cgcagatatt atcggcattg gcctggatca ggttattccg     780
gttccggttg atagcaatta tcgtatggat atcaacgagc tggagaaaat tatccgcgaa     840
ctggcaagta ccgaaacccc gattctgggc gttgtgggcg ttgtgggtag taccgaagaa     900

```
ggtgccgttg atggcattaa tgaaattgca gaactgcgta acaagctggt gaaagaaggt    960
atctatttct acttccacat cgacgccgcc tatggtggct atggtcgcgc aattctgctg   1020
gatgaagata ataagctgat cccgtataag gaccttcaga gtaaattcgc cgaatataac   1080
gtgttcaccg aagaagaaaa cctggtgagt gaacatacct ataacgccta tgccgcattt   1140
ccggaagccg aaagtgttac cattgatccg cataaaatgg ctatatccc gtatagtgca    1200 ggcggcattg ccattcagga tattcgcatg cgtgatgtta tcagctattt cgcaacctat   1260
gtgttcgaaa agggcgcaga tattccggca ctgctgggtg cttatattct ggaaggcagt   1320
aaagcaggcg caaccgcagc cagtgtttgg gcagcacata aaaccctgcc gctgaatgtt   1380
accggttatg gtggtctggt tggtgcaagc attgaaggcg cccgccgttt ttataatttt   1440
ctgagcggcc tggaattcaa ggtgggcgat aaaaccattg aagttcatcc gctgaccgat   1500
ccggatttta atatggttga ttacgtgttc caggagaagg gcaataataa tctggtggaa   1560
atgaacgagc tgaaccatga attttacaac caggcaagct acgttaccgg tagcatctat   1620
ggcaatgaat atctgaccag ccataccgat ttcgcaattc cggattatgg taatagcccg   1680
tttaagtttg tgaacaacct gggcgtgacc gaagaaggct ggaaagaagc aggtaaagtg   1740
accgttctgc gcgccgctgt gatgacacct tatatgaata aggcagagaa cttcgactac   1800
ttcgccccga aaattaagca ggccatgcag gaaaaactgg aagccatcta tgaagatcgt   1860
aag                                                                 1863
```

<210> SEQ ID NO 104
<211> LENGTH: 621
<212> TYPE: PRT
<213> ORGANISM: Artificial sequence
<220> FEATURE:
<223> OTHER INFORMATION: Engineered sequence

<400> SEQUENCE: 104

```
Met Ser Asn Thr Ser Phe Ser Ala Lys Asp Thr Asp Leu Ser Ala Leu
1               5                   10                  15

Phe Ile Gly Asp Lys Ala Glu Asn Gly Gln Leu Tyr Lys Asp Leu Leu
            20                  25                  30

Gly Lys Leu Val Asp Glu His Leu Gly Trp Arg Gln Asn Tyr Met Pro
        35                  40                  45

Gln Asp Pro Pro Met Ile Ser Ala Glu Gln Thr Ser Pro Glu Phe
    50                  55                  60

Arg Gly Thr Val Asn Asn Met Lys Asp Val Leu Asp Glu Leu Ser Ser
65                  70                  75                  80

Arg Leu Arg Ser Gln Ser Val Pro Trp His Asn Ala Gly Arg Tyr Trp
                85                  90                  95

Gly His Met Asn Ser Glu Thr Leu Met Pro Ala Ile Leu Ala Tyr Asn
            100                 105                 110

Tyr Ala Met Leu Trp Asn Gly Asn Asn Val Ala Tyr Glu Ser Ser Pro
        115                 120                 125

Ala Thr Ser Gln Met Glu Glu Val Gly Leu Glu Phe Ala Thr Leu
    130                 135                 140

Met Gly Tyr Thr Asn Gly Trp Gly His Ile Val Ala Asp Gly Ser Leu
145                 150                 155                 160

Ala Asn Leu Glu Gly Leu Trp Tyr Ala Arg Asn Ile Lys Ser Leu Pro
                165                 170                 175

Phe Ala Met Lys Ala Val Asp Pro Thr Ile Val Ala Gly Lys Thr Asp
            180                 185                 190
```

```
Trp Glu Leu Ser Asn Met Ser Thr Lys Glu Ile Met Asp Leu Val Glu
            195                 200                 205

Ala Asn Gly Asp Lys Ile Asp Glu Ile Lys Ala Lys Ser Ala Arg Gly
        210                 215                 220

Gly Lys Asp Leu Asp Lys Leu Gly Lys Trp Leu Val Pro Gln Thr Lys
225                 230                 235                 240

His Tyr Ser Trp Leu Lys Ala Ala Asp Ile Ile Gly Ile Gly Leu Asp
            245                 250                 255

Gln Val Ile Pro Val Pro Val Asp Ser Asn Tyr Arg Met Asp Ile Asn
            260                 265                 270

Glu Leu Glu Lys Ile Ile Arg Glu Leu Ala Ser Thr Glu Thr Pro Ile
            275                 280                 285

Leu Gly Val Val Gly Val Val Gly Ser Thr Glu Glu Gly Ala Val Asp
            290                 295                 300

Gly Ile Asn Glu Ile Ala Glu Leu Arg Asn Lys Leu Val Lys Glu Gly
305                 310                 315                 320

Ile Tyr Phe Tyr Phe His Ile Asp Ala Ala Tyr Gly Gly Tyr Gly Arg
            325                 330                 335

Ala Ile Leu Leu Asp Glu Asp Asn Lys Leu Ile Pro Tyr Lys Asp Leu
            340                 345                 350

Gln Ser Lys Phe Ala Glu Tyr Asn Val Phe Thr Glu Glu Asn Leu
            355                 360                 365

Val Ser Glu His Thr Tyr Asn Ala Tyr Ala Ala Phe Pro Glu Ala Glu
            370                 375                 380

Ser Val Thr Ile Asp Pro His Lys Met Gly Tyr Ile Pro Tyr Ser Ala
385                 390                 395                 400

Gly Gly Ile Ala Ile Gln Asp Ile Arg Met Arg Asp Val Ile Ser Tyr
            405                 410                 415

Phe Ala Thr Tyr Val Phe Glu Lys Gly Ala Asp Ile Pro Ala Leu Leu
            420                 425                 430

Gly Ala Tyr Ile Leu Glu Gly Ser Lys Ala Gly Ala Thr Ala Ala Ser
            435                 440                 445

Val Trp Ala Ala His Lys Thr Leu Pro Leu Asn Val Thr Gly Tyr Gly
            450                 455                 460

Gly Leu Val Gly Ala Ser Ile Glu Gly Ala Arg Arg Phe Tyr Asn Phe
465                 470                 475                 480

Leu Ser Gly Leu Glu Phe Lys Val Gly Asp Lys Thr Ile Glu Val His
            485                 490                 495

Pro Leu Thr Asp Pro Asp Phe Asn Met Val Asp Tyr Val Phe Gln Glu
            500                 505                 510

Lys Gly Asn Asn Leu Val Glu Met Asn Glu Leu Asn His Glu Phe
            515                 520                 525

Tyr Asn Gln Ala Ser Tyr Val Thr Gly Ser Ile Tyr Gly Asn Glu Tyr
            530                 535                 540

Leu Thr Ser His Thr Asp Phe Ala Ile Pro Asp Tyr Gly Asn Ser Pro
545                 550                 555                 560

Phe Lys Phe Val Asn Asn Leu Gly Val Thr Glu Glu Gly Trp Lys Glu
            565                 570                 575

Ala Gly Lys Val Thr Val Leu Arg Ala Ala Val Met Thr Pro Tyr Met
            580                 585                 590

Asn Lys Ala Glu Asn Phe Asp Tyr Phe Ala Pro Lys Ile Lys Gln Ala
            595                 600                 605
```

```
Met Gln Glu Lys Leu Glu Ala Ile Tyr Glu Asp Arg Lys
610                 615                 620
```